United States Patent [19]

Aungst

[11] Patent Number: 5,559,110
[45] Date of Patent: Sep. 24, 1996

[54] PHARMACEUTICAL FORMULATIONS OF CYCLIC UREA TYPE COMPOUNDS

[75] Inventor: Bruce J. Aungst, Wilmington, Del.

[73] Assignee: The DuPont Merck Pharmaceutical Company, Wilmington, Del.

[21] Appl. No.: 208,243

[22] Filed: Mar. 9, 1994

[51] Int. Cl.$^6$ ............ A61K 31/55; A61K 9/66; A61K 9/50; C07D 243/04
[52] U.S. Cl. ............ 514/218; 540/492; 424/455; 424/498
[58] Field of Search ............ 514/218; 540/492; 424/498, 455

[56] References Cited

U.S. PATENT DOCUMENTS

| | | | |
|---|---|---|---|
| 3,288,824 | 11/1966 | Mahler et al. | 514/12 |
| 4,525,339 | 6/1985 | Behl et al. | 424/16 |
| 4,775,659 | 10/1988 | Thakkar et al. | 514/12 |
| 4,827,062 | 5/1989 | Saeki et al. | 514/690 |
| 4,849,425 | 7/1989 | Kondo et al. | 514/274 |

FOREIGN PATENT DOCUMENTS

| | | |
|---|---|---|
| 0302370 | 7/1988 | European Pat. Off. |
| 0371471 | 6/1990 | European Pat. Off. |
| 90/08537 | 8/1990 | WIPO |
| 92/21647 | 12/1992 | WIPO |
| 93/07128 | 4/1993 | WIPO |

OTHER PUBLICATIONS

Cavanak and Sucker, Prog. Allergy, 38:65–72 (1986).
Chiou and Riegelman, J. Pharm. Sci., 60:1376–1380 (1976).
Astl et al., "Chemical Tradename Dictionary," VCH Publishers, 1993. pp. 200, 88, & 156.

Primary Examiner—Richard L. Raymond
Assistant Examiner—Mary C. Cebulak

[57] ABSTRACT

Compositions comprising a cyclic urea type compound in a liquid or solid vehicle comprising a fatty acid ester of glycerol, or a fatty acid ester of polyethylene glycol, or a mixture thereof, wherein said vehicle has an hydrophil-lipophil balance of at least about 10, and, optionally, other excipients are described. The compositions are useful for providing good systemic absorption of the cyclic urea compounds when administered enterally, especially orally. The subject compounds and compositions are useful for treating viral infections, particularly HIV infection, in a mammal.

41 Claims, No Drawings

PHARMACEUTICAL FORMULATIONS OF CYCLIC UREA TYPE COMPOUNDS

FIELD OF THE INVENTION

Novel compositions are provided comprising a cyclic urea type compound in combination with a liquid or solid vehicle, wherein said vehicle comprises fatty acid esters of glycerol or fatty acid esters of polyethylene glycol, or mixtures thereof, and wherein said vehicle has a hydrophil-lipophil balance (HLB) value of at least about 10. The subject compositions are useful in providing good systemic absorption of the cyclic urea compounds when administered orally or by other enteral means. The compositions of the invention may be used for the treatment of vital infections, particularly HIV infection.

BACKGROUND OF THE INVENTION

The optimal method of administering antiviral agents is by oral ingestion or other enteral means. With enteral dosing it is difficult, yet most desirable, to achieve maximum systemic absorption of the agent. The term oral bioavailability, for example, refers to the extent of systemic absorption of the agent when administered orally. It is well known that plasma drug concentrations, pharmacoiogic activity, and toxicity are controlled best when oral bioavailability is maximized. Poor oral bioavailability is usually associated with greater inter-subject and intra-subject variability in plasma drug concentrations, inconsistent pharmacologic activity, and unpredictable toxicity. In addition, since unabsorbed drug is essentially wasted, maximization of oral bioavailability is a means of minimizing the drug dosage requirements, which minimizes cost.

Some of the cyclic urea type antiviral agents of the present invention have exhibited poor oral bioavailability when administered in conventional formulations at relatively low doses. Others have exhibited adequate oral bioavailability at low doses, but had poor oral bioavailability at higher doses using conventional formulations. The administration of higher doses of these agents, and the attainment of drug concentrations in plasma, tissues, or other body fluids that are at or above the viral inhibitory concentrations of these agents is desirable for greatest antiviral efficacy.

Where oral bioavailability of compounds (especially compounds having low aqueous solubility) is a problem, a typical approach is to administer the drug dissolved in a non-aqueous, water miscible solvent, such as a polyethylene glycol (particularly those with low molecular weights), propylene glycol, and/or ethanol. Such solution formulations were useful for attaining suitable oral bioavailability at low doses of the antiviral agents of the present invention. However, as doses were increased in an attempt to produce greater drug concentrations in plasma, bioavailability was reduced, and plasma concentrations did not increase with increasing doses. In short, non-aqueous, water-miscible solution formulations containing polyethylene glycol, propylene glycol, ethanol, or combinations of these ingredients, were not useful for achieving good oral bioavailability with high doses of the subject cyclic urea antiviral agents.

Another generally useful approach to improve oral bioavailability that is known to those skilled in the art of drug formulation, is to disperse the drug in a solid mixture comprised of water-soluble solids such as polyethylene glycol or polyvinylpyrrolidone. These dispersions can be prepared by dissolving or co-melting the drug in the melted water-soluble carrier at high temperature, referred to as the fusion method. Dispersions can also be prepared by dissolving the drug and the water-soluble solid in a suitable solvent for all ingredients, and then evaporating the solvent. This is referred to as the solvent evaporation method. Chiou and Riegelman, *J. Pharm. Sci.*, 60:1376–1380 (1971) have shown that oral bioavailability of griseofulvin was increased in humans when administered in a solid dispersion formulation, compared to a conventional solid formulation containing micronized griseofulvin. The solid dispersions of this example consisted of griseofulvin and polyethylene glycol 6000 in a 1:9 (w:w) ratio, and they were prepared by either the fusion or solvent evaporation methods. In contrast, in the case of antiviral agents of the present invention, low oral bioavailability was observed using solid dispersion formulations containing polyethylene glycol 3350 or a combination of polyethylene glycol 3350 and polyvinylpyrrolidone.

Other compositions have been reported to improve the oral bioavailability of certain specific drugs. Ishimura et al., in European Patent Application 0 371 471 A1 (Jun. 6, 1990), for example, disclosed compositions for improved drug absorption of the drug (±)-2-carbamoyloxymethyl-4-(2,3-dichlorophenyl-6-methyl- 1,4-dihydropyridine-3,5-dicarboxylic acid 3-isopropyl ester 5-methyl ester (or its optical isomer), comprising solid dispersions of the drug in a water-soluble or enteric-soluble polymer, and a non-ionic surfactant. The preferred non-ionic surfactants claimed in EP 371,471 were glycerine fatty acid ester, glycerol monostearate, acetylated glycerine stearate, acetylated glycerine fatty acid ester, sorbitan fatty acid ester, sorbitan monolaurate, sorbitan sesquioleate, sorbitan monooleate, sorbitan trioleate, polyoxyl 40 stearate, or sucrose fatty acid ester.

Adjei et al., in European Patent Application 370 A1 (Feb. 8, 1988), disclose compositions useful for improving the oral absorption of erythromycin. These compositions contained a triglyceride oil and N-methyl pyrrolidone. Similar vehicle formulations were also claimed in PCT application WO 90/08537 (Aug. 9, 1990) to be useful for improving the oral absorption of other pharmaceutical agents.

Behl et al., in U.S. Pat. No. 4,525,339 (Jun. 25, 1985), disclose compositions useful for improving oral activity of beta lactam antibiotics. These compositions contain mono-, di-, and triglycerides of $C_2$–$C_{12}$ chain length fatty acids. The compositions are enteric coated.

Saeki et al., in U.S. Pat. No. 4,827,062 (May 2, 1989), describe a composition for improving the oral absorption of the compound ubidecarenone comprising a glycerol monounsaturated fatty acid ester, a propylene glycol monounsaturated fatty acid ester, or a mixture thereof, and a liquid oil. The preferred fatty acid of the glycerol and propylene glycol esters was oleic acid. However, when tested in combination with cyclic urea compounds of the present invention, vehicles employing glycerol monooleate, oleic acid and propylene glycol fatty acid esters were found to be unsuitable for improving the oral absorption of these compounds.

Cavanak and Sucker, in *Prog. Allergy* 38: 65–72 (1986), describe the development of cyclosporin formulations which afforded good oral absorption. A preferred formulation contained cyclosporin in a mixture of olive oil, ethanol, and ethoxylated persic oil. The ethoxylated persic oil used was a commercial brand referred to as Labrafil™ M 1944 CS, which is known to contain glycerides and polyethylene glycol esters.

As the foregoing indicates, a number of examples exist where particular vehicles have been found useful in increasing the bioavailability of certain specific drugs. However, it is difficult to extrapolate any such findings from one type or class of drug to another. For example, although it is known generally in the art that polyethylene glycol, propylene glycol and ethanol may increase oral bioavailability of compounds, such formulations were not useful for achieving good oral bioavailability with high doses of the subject cyclic urea antiviral agents. Similarly, notwithstanding the apparent success in Saeki et al, U.S. Pat. No. 4,827,062 with vehicles for the drug ubidecarenone comprised of glycerol monounsaturated fatty acid esters and/or propylene glycol monounsaturated fatty acid esters, vehicles employing glycerol monooleate, oleic acid and propylene glycol fatty acid esters were found to be unsuitable for improving oral absorption of the cyclic urea compounds of the present invention. Moreover, solid dispersion formulations containing polyethylene glycol 3350 or a combination of polyethylene glycol 3350 and polyvinylpyrrolidone were tested and found to be unsuitable for improving the oral bioavailability of cyclic urea compounds of the present invention, despite the teachings in the art, including the teachings in Chiou and Riegelman, *J. Pharm. Sci.*, 60:1376–1380 (1971), where griseofulvin bioavailability was increased with similar solid dispersion formulations.

In the present invention, pharmaceutical compositions have been discovered which provide good bioavailability for the cyclic urea antiviral compounds disclosed herein. The subject formulations allow good systemic absorption of the antiviral agents when administered orally or by other enteral means, not only at low doses, but also at high dosage levels. This, in turn, permits better control of plasma drug concentrations, pharmacologic activity and drug toxicity, and minimizes cost by reducing drug loss from poor systemic absorption. These and/or other advantages of the present invention are further described below.

SUMMARY OF THE INVENTION

The present invention provides, inter alia, novel compositions of antiviral agents, such as the cyclic urea compounds of the Formula (I) below, and derivatives thereof. The subject compositions are capable of achieving good systemic absorption when administered orally or by other enteral means.

Specifically, the present invention is directed, among other things, to compositions comprising a compound of Formula (I), in combination with a liquid or solid vehicle comprising a fatty acid ester of glycerol, a fatty acid ester of polyethylene glycol, or a mixture thereof, wherein said vehicle has a hydrophil-lipophil balance (HLB) value of at least about 10, and, optionally, other pharmaceutical excipients. Methods of using the subject novel compositions, methods for their preparation, and pharmaceutical kits and dosage forms containing the novel composition components are also described.

DETAILED DESCRIPTION OF THE INVENTION

The present invention provides an effective method for attaining good systemic absorption of cyclic urea type compounds, and provides compositions containing such compounds. The compositions allow for good systemic absorption of the subject compound when administered orally or by other enteral means.

As used herein, the phrases "cyclic urea compound", "cyclic urea type compound", "cyclic antiviral agent", or "cyclic HIV protease inhibitor" are used interchangeably and include the compounds of Formula (I) described below. The compounds of Formula (I) are also described in PCT International Patent Application Publication No. WO 93/07128 and in copending, commonly assigned U.S. patent application U.S. Ser. No. 08/047,330, the disclosures of each of which are hereby incorporated herein by reference, in their entirety.

As disclosed in PCT International Patent Application Publication No. WO 93/07128 and in copending, commonly assigned U.S. patent application U.S. Ser. No. 08/047,330, cyclic urea type compounds of Formula (I) represent a new class of antiviral agents which function as HIV protease inhibitors and are useful for the treatment of HIV infection. These cyclic HIV protease inhibitors lack the amide bonds found in previous inhibitors, but retain the symmetry of the potent C-2 symmetrical diols.

[1] The cyclic urea type compounds useful in this invention include cyclic compounds of the Formula (I):

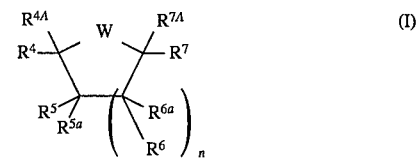

or a pharmaceutically acceptable salt or prodrug form thereof,
wherein:

$R^4$ and $R^7$ are independently selected from the following groups:
hydrogen;
$C_1$–$C_8$ alkyl substituted with 0-3 $R^{11}$;
$C_2$–$C_8$ alkenyl substituted with 0-3 $R^{11}$;
$C_2$–$C_8$ alkynyl substituted with 0-3 $R^{11}$;
a $C_3$–$C_{14}$ carbocyclic ring system substituted with 0-3 $R^{11}$ or 0-3 $R^{12}$;
a 5- to 10-membered heterocyclic ring system containing 1 to 4 heteroatoms independently selected from oxygen, nitrogen or sulfur, said heterocyclic ring system being substituted with 0-2 $R^{12}$;
—$OR^{13}$; —$SR^{13}$; $CO_2R^{13}$;

$R^{4A}$ and $R^{7A}$ are independently selected from the following groups:
hydrogen;
$C_1$–$C_4$ alkyl substituted with 0-6 halogen or 0-3 $C_1$–$C_2$ alkoxy;
pbenzyl substituted with 0-6 halogen or 0-3 $C_1$–$C_2$ alkoxy;
—$OR^{13}$; —$SR^{13}$; $CO_2R^{13}$;

$R^4$ and $R^{4A}$ can alternatively join to form a 5-7 membered carbocyclic ring substituted with 0-2 $R^{12}$;
$R^7$ and $R^{7A}$ can alternatively join to form a 5-7 membered carbocyclic ring substituted with 0-2 $R^{12}$;
n is 0, 1, or 2;
$R^5$ is selected from H; halogen; $C_1$–$C_6$ alkyl substituted with 0-3 $R^{11}$; —$N(R^{20})_2$; —$SR^{20}$; or —$OR^{20}$, —$N_3$;
$R^6$ is independently selected from: hydrogen, halogen, $C_1$–$C_6$ alkyl substituted with 0-3 $R^{11}$, —$N(R^{20})_2$, —$SR^{20}$, or —$OR^{21}$, —$N_3$;
$R^5$ and $R^6$ can alternatively join to form an epoxide or aziridine ring; —$OCH_2SCH_2O$—; —$OC(=O)O$—; —$OCH_2O$—; —$OC(=S)O$—; —$OC(=O)C(=O)O$—; —$OC(CH_3)_2O$—; —$OC((CH_2)_3NH_2)$ $(CH_3)O$—; —$OC(OCH_3)$ $(CH_2CH_2CH_3)O$—; —$OS$ $(=O)O$—; —$NHC(=O)NH$—; —$OC(=O)NH$—; —$NHC(=O)O$—;

—NHCH$_2$O—; —OCH$_2$NH—; —NHC(=S)O—; —OS(=O)NH—; —NHC(=O)C(=O)O—; —OC(=O)C(=O)NH—; —NHC(=O)C(=O)NH—; —NHC(CH$_3$)$_2$O—; —OC(CH$_3$)$_2$NH— or any group that, when administered to a mammalian subject, cleaves to form a free dihydroxyl or diamino or hydroxyl and amino;

R$^{5a}$ is selected from hydrogen, halogen, C$_1$–C$_6$ alkyl, —N(R$^{20}$)$_2$, —SR$^{20}$, or —OR$^{20}$;

R$^{6a}$ is selected from: hydrogen, halogen, C$_1$–C$_6$ alkyl, —N(R$^{20}$)$_2$, —SR$^{20}$ or —OR$^{21}$;

R$^5$ and R$^{5a}$ can alternatively join to form =O, =S, or a ketal ring;

R$^6$ and R$^{6a}$ can alternatively join to form =O, =S, or a ketal ring;

R$^{20}$ and R$^{21}$ are independently selected from:
hydrogen;
C$_1$–C$_6$ alkyl substituted with 0-3 R$^{11}$;
C$_3$–C$_6$ alkoxyalkyl substituted with 0-3 R$^{11}$;
C$_1$–C$_6$ alkylcarbonyl substituted with 0-3 R$^{11}$;
C$_1$–C$_6$ alkoxycarbonyl substituted with 0-3 R$^{11}$;
C$_1$–C$_6$ alkylaminocarbonyl substituted with 0-3 R$^{11}$;
benzoyl substituted with 0-3 R$^{12}$;
phenoxycarbonyl substituted with 0-3 R$^{12}$;
phenylaminocarbonyl substituted with 0-3 R$^{12}$; or any group that, when administered to a mammalian subject, cleaves to form a free hydroxyl, amino or sulfhydryl;

R$^{11}$ is selected from one or more of the following:
H, keto, halogen, cyano, —CH$_2$NR$^{13}$R$^{14}$, —NR$^{13}$R$^{14}$, —CO$_2$R$^{13}$, —OC(=O)R$^{13}$, —OR$^{13}$, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$_{14}$C(=O)OR$^{14}$, —OC(=O) NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, —OP(O)(OR$^{13}$)$_2$, C$_1$–C$_4$ alkyl, C$_2$–C$_4$ alkenyl, C$_3$–C$_6$ cycloalkylmethyl, benzyl, phenethyl, phenoxy, benzyloxy, nitro, C$_7$–C$_{10}$ arylalkyl, hydroxamic acid, hydrazide, boronic acid, sulfonamide, formyl, C$_3$–C$_6$ cycloalkoxy, C$_1$–C$_4$ alkyl substituted with —NR$^{13}$R$^{14}$, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, pyridylcarbonyloxy, C$_1$–C$_4$ alkylcarbonyl, C$_1$–C$_4$ alkylcarbonylamino, —OCH$_2$CO$_2$H, 2-(1-morpholino)ethoxy, azido, or —C(R$^{14}$)=N(OR$^{14}$);

1-3 amino acids linked together via amide bonds, said amino acid being linked via the amine or carboxylate terminus;
C$_3$–C$_{10}$ cycloalkyl substituted with 0-2 R$^{12}$;
C$_1$–C$_4$ alkyl substitued with 0-2 R$^{12}$
aryl(C$_1$–C$_3$ alkyl) substituted with 0-2 R$^{12}$;
C$_2$–C$_6$ alkoxyalkyl, substituted with 0-2 R$^{12}$;
C$_1$–C$_4$ alkylcarbonyloxy substituted with 0-2 R$^{12}$,
C$_6$–C$_{10}$ arylcarbonyloxy substituted with 0-2 R$^{12}$,
a C$_5$–C$_{14}$ carbocyclic residue substituted with 0-3 R$^{12}$;
a 5- to 10-membered heterocyclic ring system containing 1 to 4 heteroatoms independently selected from oxygen, nitrogen or sulfur, said heterocyclic ring system being substituted with 0-3 R$^{12}$;

R$^{11A}$ is selected from one or more of the following:
H, keto, halogen, cyano, —CH$_2$NH$_2$, —NH$_2$, —NHMe, —CO$_2$H, —OC(=O)(C$_1$–C$_3$ alkyl), —OH, C$_2$–C$_6$ alkoxyalkyl, —C(=O)NH$_2$, —OC(=O)NH$_2$, —NHC(=O)NH$_2$, —SO$_2$NH$_2$, C$_1$–C$_4$ alkyl, C$_2$–C$_4$ alkenyl, C$_3$–C$_{10}$ cycloalkyl, C$_3$–C$_6$ cycloalkylmethyl, benzyl, phenethyl, phenoxy, benzyloxy, nitro, C$_7$–C$_{10}$ arylalkyl, hydroxamic acid, hydrazide, boronic acid, C$_3$–C$_6$ cycloalkoxy, C$_1$–C$_4$ alkyl substituted with —NH$_2$, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —OCH$_2$CO$_2$H, 2-(1-morpholino) ethoxy, azido, aryl (C$_1$–C$_3$ alkyl), a C$_5$–C$_{14}$ carbocyclic residue; a 5- to 10-membered heterocyclic ring system containing 1 to 4 heteroatoms independently selected from oxygen, nitrogen or sulfur, said heterocyclic ring system substituted with 0-3 R$^{12A}$.

R$^{12}$ when a substituent on carbon, is selected from one or more of the following:
phenyl, benzyl, phenethyl, phenoxy, benzyloxy, halogen, hydroxy, nitro, cyano, C$_1$–C$_4$ alkyl, C$_3$–C$_6$ cycloalkyl, C$_3$–C$_6$ cycloalkylmethyl, C$_7$–C10 arylalkyl, C$_1$–C$_4$ alkoxy, —CO$_2$H, hydroxamic acid, hydrazide, boronic acid, sulfonamide, formyl, C$_3$–C$_6$ cycloalkoxy, —OR$^{13}$, C$_1$–C$_4$ alkyl substituted with —NR$^{13}$R$^{14}$, —NR$^{13}$R$^{14}$, C$_2$–C$_6$ alkoxyalkyl optionally substituted with —Si(CH$_3$)$_3$, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(O)$_m$R$^{13}$, —SO$_2$NR$^{13}$R$^{14}$, —NHSO$_2$R$^{14}$, —OCH$_2$CO$_2$R$^{13}$, 2-(1-morpholino)ethoxy, —C(R$^{14}$)=N(OR$^{14}$); or a 5- or 6-membered heterocyclic ring containing from 1 to 4 heteroatoms independently selected from oxygen, nitrogen or sulfur;

or R$^{12}$ may be a 3- or 4- carbon chain attached to adjacent carbons on the ring to form a fused 5- or 6- membered ring, said 5- or 6- membered ring being optionally substituted on the aliphatic carbons with halogen, C$_1$–C$_4$ alkyl, C$_1$–C$_4$ alkoxy, hydroxy, or —NR$^{13}$R$^{14}$; or, when R$^{12}$ is attached to a saturated carbon atom, it may be =O or =S; or when R$^{12}$ is attached to sulfur it may be =O.

R$^{12}$ when a substituent on nitrogen, is selected from one or more of the following:
phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl C$_3$–C$_6$ cycloalkylmethyl —CH$_2$NR$^{13}$R$^{14}$, —NR$^{13}$R$^{14}$, C$_2$–C$_6$ alkoxyalkyl, C$_1$–C$_4$ haloalkyl, C$_1$–C$_4$ alkoxycarbonyl, —CO$_2$H, C$_1$–C$_4$ alkylcarbonyloxy, C$_1$–C$_4$ alkylcarbonyl, —C(R$^{14}$)=N(OR$^{14}$);

R$^{12A}$ when a substituent on carbon, is selected from one or more of the following:
phenyl, benzyl, phenethyl, phenoxy, benzyloxy, halogen, hydroxy, nitro, cyano, C$_1$–C$_4$ alkyl, C$_3$–C$_6$ cycloalkyl, C$_3$–C$_6$ cycloalkylmethyl, C$_7$–C$_{10}$ arylalkyl, C$_1$–C$_4$ alkoxy, —CO$_2$H, hydroxamic acid, hydrazide, boronic acid, sulfonamide, formyl, C$_3$–C$_6$ cycloalkoxy, —OR$^{13}$, C$_1$–C$_4$ alkyl substituted with —NH$_2$, —NH$_2$, —NHMe, C$_2$–C$_6$ alkoxyalkyl optionally substituted with —Si(CH$_3$)$_3$, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(O)$_m$Me, —SO$_2$NH$_2$, —NHSO$_2$Me, —OCH$_2$CO$_2$R$^{13}$, 2-(1-morpholino)ethoxy, —C(=NOH)NH$_2$; or a 5- or 6-membered heterocyclic ring containing from 1 to 4 heteroatoms independently selected from oxygen, nitrogen or sulfur;

or R$^{12A}$ may be a 3- or 4- carbon chain attached to adjacent carbons on the ring to form a fused 5- or 6- membered ring, said 5- or 6- membered ring being optionally substituted on the aliphatic carbons with halogen, C$_1$–C$_4$ alkyl, C$_1$–C$_4$ alkoxy, hydroxy, or —NH$_2$; or, when R$^{12A}$ is attached to a saturated carbon atom or sulfur, it may be =O or =S;

R$^{12A}$ when a substituent on nitrogen, is selected from one or more of the following:

phenyl, benzyl, phenethyl, hydroxy, $C_1-C_4$ hydroxyalkyl, $C_1-C_4$ alkoxy, $C_1-C_4$ alkyl, $C_3-C_6$ cycloalkyl, $C_3-C_6$ cycloalkylmethyl, $-CH_2NH_2$, $-NH_2$, $C_2-C_6$ alkoxyalkyl, $C_1-C_4$ haloalkyl, $C_1-C_4$ alkoxycarbonyl, $-CO_2H$, $C_1-C_4$ alkylcarbonyloxy, $C_1-C_4$ alkylcarbonyl, $-C(=NOH)NH_2$;

$R^{13}$ is selected from:
H;
phenyl substituted with 0-3 $R^{11A}$;
benzyl substituted with 0-3 $R^{11A}$;
$C_1-C_6$ alkyl substituted with 0-3 $R^{11A}$;
$C_2-C_4$ alkenyl substituted with 0-3 $R^{11A}$;
$C_1-C_6$ alkylcarbonyl substituted with 0-3 $R^{11A}$;
$C_1-C_6$ alkoxycarbonyl substituted with 0-3 $R^{11A}$;
$C_1-C_6$ alkylaminocarbonyl substituted with 0-3 $R^{11A}$;
$C_3-C_6$ alkoxyalkyl substituted with 0-3 $R^{11A}$;
an amine protecting group when $R^{13}$ is bonded to N;
a hydroxy protecting group when $R^{13}$ is bonded to O;

$R^{14}$ is hydrogen, hydroxy, $CF_3$, $C_1-C_6$ alkyl substituted with 0-3 groups selected from OH, $C_1-C_4$ alkoxy, halogen, $NH_2$, $-NH(C_1-C_4$ alkyl), $C_1-C_6$ alkoxy, $C_2-C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form $-(CH_2)_4-$, $-(CH_2)_5-$, $-CH_2CH_2N(R^{15})CH_2CH_2-$, or $-CH_2CH_2OCH_2CH_2-$;

$R^{15}$ is H or $CH_3$;
m is 0, 1 or 2;
W is selected from:
$-N(R^{22})C(=Z)N(R^{23})-$;
$-OC(=Z)O-$;
$-N(R^{22})C(=Z)O-$;
$-C(R^{25})(R^{26})C(=Z)C(R^{27})(R^{28})-$;
$-N(R^{22})C(=Z)C(R^{27})(R^{28})-$;
$-C(R^{25})(R^{26})C(=Z)O-$;
$-N(R^{22})C(=Z)C(=Z)N(R^{23})-$;
$-C(R^{25})(R^{26})C(F_2)C(R^{27})(R^{28})-$;
$-C(R^{25})(R^{26})N(CH_3)(O)C(R^{27})(R^{28})-$;
$-C(R^{25})(R^{26})N(OR^{29})C(R^{27})(R^{28})-$;
$-C(R^{25})(R^{26})C(=Z)S-$;
$-N(R^{22})S(=Z')N(R^{23})-$;
$-N(R^{22})S(=Z')_2N(R^{23})-$;
$-N(R^{22})P(=O)(R^{24a})N(R^{23})-$;
$-C(R^{25})(R^{26})S(=Z')C(R^{27})(R^{28})-$;
$-C(R^{25})(R^{26})S(=Z')_2C(R^{27})(R^{28})-$;
$-C(R^{25})(R^{26})P(=O)(R^{24a})C(R^{27})(R^{28})-$;
$-C(R^{25})(R^{26})S(=Z')N(R^{23})-$;
$-C(R^{25})(R^{26})S(=Z')_2N(R^{23})-$;
$-C(R^{25})(R^{26})S(=O)_2O-$;
$-C(R^{25})(R^{26})P(=O)(R^{24a})N(R^{23})-$;
$-C(R^{25})(R^{26})P(=O)(R^{24a})O-$;
$-C(R^{25})C(F_2)C(=O)N(R^{23})-$;
$-C(R^{25})C(F_2)S(=O)_2N(R^{23})-$;
$-SC(=Z)-$;
$-C(R^{25})(R^{26})C(R^{34})(R^{34})(R^{35})C(R^{27})(R^{28})-$;
$-N(R^{22})C(R^{34})(R^{35})N(R^{23})-$;
$-N=C(R^{36})N(R^{23})-$;
$-N^+(R^{22})=C(R^{36})N(R^{23})-$;
$-N(R^{22})P(R^{24a})N(R^{23})-$;
$-C(=Z)-$;
$-P(=O)(R^{24a})-$;
$-S(=Z')-$;
$-S(=Z')_2-$;
$-N(R^{22})C(=C(R^{36a})(R^{36b}))N(R^{23})-$;
$-N(R^{22})C(=Z)N(R^{23})C(=Z)-$;
wherein:

Z is O, S, $NR^{24}$;
Z' is O or $NR^{24}$;
$Z^{22}$ is $R^{23}$ are independently selected from the following:
hydrogen;
$C_1-C_8$ alkyl substituted with 0-3 $R^{31}$;
$C_2-C_8$ alkenyl substituted with 0-3 $R^{31}$;
$C_2-C_8$ alkenyl substituted with 0-3 $R^{31}$;
a $C_3-C_{14}$ carbocyclic ring system substituted with 0-5 $R^{31}$ or 0-5 $R^{32}$;
a 5- to 10-membered heterocyclic ring system containing 1 to 4 heteroatoms independently selected from oxygen, nitrogen or sulfur, said heterocyclic ring system being substituted with 0-2 $R^{32}$;
$-OR^{22a}$; $-N(R^{22a})(R^{22b})$;

$R^{22a}$ and $R^{22b}$ are independently selected from the following:
hydrogen;
$C_1-C_8$ alkyl substituted with 0-3 $R^{31}$;
$C_2-C_8$ alkenyl substituted with 0-3 $R^{31}$;
$C_2-C_8$ alkenyl substituted with 0-3 $R^{31}$;
a $C_3-C_{14}$ carbocyclic ring system substituted with 0-5 $R^{31}$ or 0-5 $R^{32}$;
a 5- to 10-membered heterocyclic ring system containing 1 to 4 heteroatoms independently selected from oxygen, nitrogen or sulfur, said heterocyclic ring system being substituted with 0-2 $R^{32}$;

$R^{24}$ is selected from: hydrogen; hydroxy; amino; $C_1-C_4$ alkyl; $C_1-C_4$ alkoxy; mono- or di-$(C_1-C_6$ alkyl)amino; cyano; nitro; benzyloxy; $-NHSO_2$aryl, aryl being optionally substituted with $(C_1-C_6)$alkyl;

$R^{24a}$ is selected from: hydroxy; amino; $C_1-C_4$ alkyl; $C_1-C_4$ alkoxy; mono- or di-$(C_1-C_6$ alkyl)amino; cyano; nitro; benzyloxy; or phenoxy;

$R^{25}$ and $R^{27}$ are independently selected from the following:
hydrogen;
$C_1-C_8$ alkyl substituted with 0-3 $R^{31}$;
$C_2-C_8$ alkenyl substituted with 0-3 $R^{31}$;
$C_2-C_8$ alkenyl substituted with 0-3 $R^{31}$;
a $C_3-C_{14}$ carbocyclic ring system substituted with 0-5 $R^{31}$ or 0-5 $R^{32}$;
a 5- to 10-membered heterocyclic ring system containing 1 to 4 heteroatoms independently selected from oxygen, nitrogen or sulfur, said heterocyclic ring system being substituted with 0-2 $R^{32}$;
$-OR^{13}$; $-SR^{13}$;

$R^{26}$ and $R^{28}$ are independently selected from:
hydrogen;
halogen;
$C_1-C_4$ alkyl substituted with 0-3 halogen or 0-3 $C_1-C_2$ alkoxy;
benzyl substituted with 0-3 halogen or 0-3 $C_1-C_2$ alkoxy;
$-OR^{13}$; $-SR^{13}$;

$R^{29}$ is selected from:
hydrogen;
$C_1-C_4$ alkyl substituted with 0-3 halogen or 0-3 $C_1-C_2$ alkoxy;
benzyl substituted with 0-3 halogen or 0-3 $C_1-C_2$ alkoxy;
alternatively, $R^{22}$, $R^{25}$, or $R^{26}$ independently, can join with $R^4$ or $R^{4A}$ to form a 5- or 6-membered fused heterocyclic ring or carbocyclic ring substituted with 0-2 $R^{12}$, said heterocyclic ring containing 1-3 heteroatoms independently selected from N, S, or O; or
alternatively, $R^{23}$ $R^{27}$ or $R^{28}$ independently, can join with $R^7$ or $R^{7A}$ to form a 5- or 6-membered fused heterocyclic ring or carbocyclic ring substituted with 0-2 $R^{12}$ said heterocyclic ring containing 1-3 heteroatoms independently selected from N, S, or 0; or alternatively, $R^{22}$ $R^{25}$ $R^{26}$ $R^{23}$ $R^{27}$ $R^{28}$ $R^{34}$ or $R^{35}$ can join with $R^5$ or $R^6$ to form a 0- to 7-membered bridge to form a carbocyclic or heterocyclic ring, said bridge being substituted with 0-2 $R^{12}$ and said bridge containing 0-3 heteroatoms independently selected from N, S, or 0 (i.e., a 0-membered bridge is formed when $R^{22}$, $R^{25}$, $R^{26}$, $R^{23}$, $R^{27}$, $R^{28}$, $R^{34}$, or $R^{35}$ are taken together with $R^5$ or $R^6$ to form a direct bond);

alternatively R28 or R23 can join with R7A to form a direct bond; alternatively R26 or R22 can join with R4A to form a direct bond;

$R^{31}$ is selected from one or more of the following:

keto, halogen, cyano, —CH$_2$NR$^{13}$R$^{14}$, —NR$^{13}$R$^{14}$, —CO$_2$R$^{13}$, —C(=O)R$^{11}$, —OC(=O)R$^{13}$, —OR$^{13}$, C$_2$–C$_6$ g alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{13}$C(=S)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, C$_1$–C$_4$ alkyl, C$_2$–C$_4$ alkenyl, C$_3$–C$_{10}$ cycloalkyl, C$_3$–C$_6$ cycloalkylmethyl, benzyl, phenethyl, phenoxy, benzyloxy, nitro, C$_7$–C$_{10}$ arylalkyl, hydroxamic acid, hydrazide, oxime, boronic acid, sulfonamide, formyl, C$_3$–C$_6$ cycloalkoxy, C$_1$–C$_4$ alkyl substituted with —NR$^{13}$R$^{14}$, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —OCH$_2$CO$_2$R$^{13}$, 2-(1-morpholino)ethoxy, azido, —C(R$^{14}$)=N(OR$^{14}$); or 1-3 amino acids, linked together via amide bonds, said amino acid being linked via the amine or carboxylate terminus;

a C$_5$–C$_{14}$ carbocyclic residue substituted with 0-5 R$^{32}$; or a 5- to 10-membered heterocyclic ring system containing 1 to 4 heteroatoms independently selected from oxygen, nitrogen or sulfur, said heterocyclic ring system being substituted with 0-2 R$^{32}$;

$R^{32}$, when a substituent on carbon, is selected from one or more of the following:

phenethyl, phenoxy, C$_3$–C$_{10}$ cycloalkyl, C$_3$–C$_6$ cycloalkylmethyl, C$_7$–C$_{10}$ arylalkyl, hydrazide, oxime, boronic acid, C$_2$–C$_6$ alkoxyalkyl, methylenedioxy, ethylenedioxy, C$_1$–C$_4$ alkylcarbonyloxy, —NHSO$_2$R$^{14}$, benzyloxy halogen, 2-(1-morpholino)ethoxy, —CO$_2$R$^{13}$, hydroxamic acid, —CONR$^{13}$NR$^{13}$R$^{14}$, cyano sulfonamide, —CHO, C$_3$–C$_6$ cycloalkoxy, —NR$^{13}$R$^{14}$, —C(R$^{14}$)=N(OR$^{14}$), —NO$_2$, —OR$^{13}$, —NR$^{40}$R$^{41}$, —SO$_m$R$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —OCO$_2$R$^{13}$, phenyl, —C(=O)NR$^{13}$—(C$_1$–C$_4$ alkyl)—NR$^{13}$R$^{14}$, —C(=O)NR$^{40}$R$^{41}$, C$_1$–C$_4$ haloalkyl, C$_1$–C$_4$ haloalkoxy, C$_2$–C$_4$ haloalkenyl, C$_1$–C$_4$ haloalkynyl, or
—C(=O) NR$^{13}$C(R$^{11}$)$_2$NR$^{13}$R$^{14}$; —C(=O)NR$^{13}$C(R$^{11}$)$_2$NR$^{13}$CO$_2$R$^{13}$; —C(=O)NR$^{13}$—(C$_1$–C$_4$ alkyl) —NR$^{13}$CO$_2$R$^{13}$; —C(=O)N(R$^{13}$)—(C$_1$–C$_4$ alkyl)—R$^{11}$; or
—C(=O)C(R$^{11}$)$_2$NR$^{13}$R$^{14}$; —C(=O)C(R$^{11}$)$_2$NR$^{13}$CO$_2$R$^{13}$; —C(=O)—(C$_1$–C$_4$ alkyl)—NR$^{13}$R$^{14}$; —C(=O)—(C$_1$–C$_4$ alkyl)—NR$^{13}$CO$_2$R$^{13}$; or C$_1$–C$_4$ alkoxy substituted with 0-4 groups selected from: R$^{11}$, C$_3$–C$_6$ cycloalkyl, —CO$_2$R$^{13}$, —C(=O)NR$^{13}$R$^{14}$, —NR$^{13}$R$^{14}$ or OH;

C$_1$–C$_4$ alkyl substituted with 0-4 groups selected from: R$^{11}$, =NR$^{14}$, =NNR$^{13}$C(=O)NR$^{13}$R$^{14}$, =NNR$^{13}$C(=O)OR$^{13}$, or —NR$^{13}$R$^{14}$;

C$_2$–C$_4$ alkenyl substituted with 0-4 R$^{11}$;
C$_2$–C$_4$ alkenyl substituted with 0-4 R$^{11}$;

a 5- or 6-membered heterocyclic ring containing from 1 to 4 heteroatoms independently selected from oxygen, nitrogen or sulfur, substituted with 0-2 R$^{12}$;

or R$^{32}$ may be a 3- or 4- carbon chain attached to adjacent carbons on the ring to form a fused 5- or 6- membered ring, said 5- or 6- membered ring being optionally substituted on the aliphatic carbons with halogen, C$_1$–C$_4$ alkyl, C$_1$–C$_4$ alkoxy, hydroxy, or —NR$^{13}$R$^{14}$; or, when R$^{32}$ is attached to a saturated carbon atom, it may be =O, =S, =NOH; or when R$^{32}$ is attached to sulfur it may be =O.

$R^{32}$ when a substituent on nitrogen, is selected from one or more of the following:

phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$NR$^{13}$R$^{14}$, —NR$^{13}$R$^{14}$, C$_2$–C$_6$ alkoxyalkyl, C$_1$–C$_4$ haloalkyl, C$_1$–C$_4$ alkoxycarbonyl, —CO$_2$H, C$_1$–C$_4$ alkylcarbonyloxy, C$_1$–C$_4$ alkylcarbonyl, —C(R$^{14}$)=N(OR$^{14}$);

$R^{34}$ is selected from:
hydrogen;
OR$^{13}$;
SR$^{13}$;
halogen;
N(R$^{38}$)(R$^{39}$)
C$_1$–C$_6$ alkyl substituted with 0-3 R$^{11}$;
C$_1$–C$_6$ alkoxy substituted with 0-3 R$^{11}$;
C$_1$–C$_6$ thioalkyl substituted with 0-3 R$^{11}$;

$R^{35}$ is selected from:
hydrogen;
OR$^{13}$;
SR$^{13}$;
halogen;
N(R$^{38}$)(R$^{39}$)
C$_1$–C$_6$ alkyl substituted with 0-3 R$^{11}$;
C$_1$–C$_6$ alkoxy substituted with 0-3 R$^{11}$;
C$_1$–C$_6$ thioalkyl substituted with 0-3 R$^{11}$;

$R^{34}$ and $R^{35}$ can be taken together to form a ketal ring, a 3- to 8-membered carbocyclic ring, or a 5- or 6-membered heterocyclic ring containing 1-3 heteroatoms independently selected from the group O, N, or S, said ring substituted with 0-5 R$^{11}$;

$R^{36}$ is selected from:
H
C$_1$–C$_6$ alkyl substituted with 0-3 R$^{11}$;
—COR$^{37}$;
—NR$^{38}$R$^{39}$;
—CN;
—NO$_2$ $R^{37}$ is selected from:
hydrogen;
C$_1$–C$_6$ alkyl substituted with 0-3 R$^{11}$;
hydroxyl;
C$_1$–C$_6$ alkoxy substituted with 0-3 R$^{11}$;
—NR$^{38}$R$^{39}$;

$R^{38}$ and $R^{39}$ are independently selected from:
hydrogen;
C$_1$–C$_6$ alkyl substituted with 0-3 R$^{11}$; or
an amine protecting group;

$R^{40}$ is selected from: H, C$_1$–C$_3$ alkyl;

$R^{41}$ is selected from:
—C(=O)NR$^{13}$R$^{14}$;
—C(=O)NR$^{13}$NR$^{13}$R$^{14}$;
—C(=O)C(R$^{11}$)$_2$NR$^{13}$R$^{14}$;
—C(=O)C(R$^{11}$)$_2$NR$^{13}$NR$^{13}$R$^{14}$;
—C(=O)C(R$^{11}$)$_2$NR$^{13}$CO$_2$R$^{13}$;
—C(=O)H;

—$C(=O)R^{11}$;
—$C(=O)$—$(C_1$–$C_4$ alkyl)—$NR^{13}R^{14}$;
—$C(=O)$—$(C_1$–$C_4$ alkyl)—$NR^{13}CO_2R^{13}$;
—C(1-3 amino acids linked together via amide bonds, and linked to the N atom via the carboxylate terminus;
provided that:
$R^4$, $R^{4A}$, $R^7$ and $R^{7A}$ are not all hydrogen;
when W is —$OC(=Z)O$—, —$SC(=Z)$—, —$C(=Z)$—, —$P(=O)(R^{24a})$—, —$S(=Z')$— or —$S(=Z')_2$—, $R^4$ and $R^7$ are not hydrogen;
when $R^4$, $R^{4A}$ are hydrogen, at least one of the following is not hydrogen: $R^{22}$, $R^{25}$, and $R^{26}$.

[2] Preferred compounds useful in the pharmaceutical compositions of the present invention are compounds of Formula (I) wherein:
$R^4$ and $R^7$ are independently selected from the following groups:
hydrogen;
$C_1$–$C_4$ alkyl substituted with 0-3 $R^{11}$;
$C_3$–$C_4$ alkenyl substituted with 0-3 $R^{11}$;
$C_3$–$C_4$ alkenyl substituted with 0-3 $R^{11}$;
$R^{4A}$ and $R^{7A}$ are hydrogen;
$R^5$ is selected from fluoro or —$OR^{20}$;
$R^6$ is independently selected from: hydrogen, flurry or —$OR^{21}$;
$R^5$ and $R^6$ can alternatively join to form an epoxide or aziridine ring; —$OCH_2SCH_2O$—; —$OS(=O)O$—; —$OC(=O)O$—; —$OCH_2O$—; —$OC(=S)O$—; —$OC(=O)C(=O)O$—; —$OC(CH_3)_2O$—; —$OC(OCH_3)(CH_2CH_2CH_3)O$—; or any group that, when administered to a mammalian subject, cleaves to form a free dihydroxyl;
$R^{5a}$ is selected from hydrogen or fluoro;
$R^{6a}$ is selected from: hydrogen or flurry;
$R^5$ and $R^{5a}$ can alternatively join to form =O, =S, or a ketal ring;
$R^6$ and $R^{6a}$ can alternatively join to form =O, =S, or a ketal ring;
$R^{20}$ and $R^{21}$ are independently selected from:
hydrogen;
$C_1$–$C_6$ alkylcarbonyl;
$C_1$–$C_6$ alkoxycarbonyl;
benzoyl; or any group that, when administered to a mammalian subject, cleaves to form a free hydroxyl;
$R^{11}$ is selected from one or more of the following:
H, keto halogen cyano —$CH_2NR^{13}R^{14}$ —$NR^{13}R^{14}$, —$CO_2^{13}$, —$OC(=O)R^{13}$, —$OR^{13}$, $C_2$–$C_4$ alkoxyalkyl, —$S(O)_mR^{13}$, $C_1$–$C_4$ alkyl, $C_2$–$C_4$ alkenyl, $C_3$–$C_{10}$ cycloalkyl;
a $C_5$–$C_{14}$ saturated or partially unsaturated carbocyclic residue substituted with 0-3 $R^{12}$;
aryl($C_1$–$C_3$ alkyl) substituted with 0-2 $R^{12}$;
aryl substituted with 0-3 $R^{12}$; or
a 5- to 10-membered heterocyclic ring system containing 1 to 4 heteroatoms independently selected from oxygen, nitrogen or sulfur, said heterocyclic ring system being substituted with 0-2 $R^{12}$;
$R^{12}$ when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, 2-(1-morpholino)ethoxy, —$CO_2H$, hydroxamic acid, hydrazide, —$C(R^{14})=N(OR^{14})$, cyano, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$; or
a 5- or 6-membered heterocyclic ring containing from 1 to 4 heteroatoms independently selected from oxygen, nitrogen or sulfur;
or $R^{12}$ may be a 3- or 4- carbon chain attached to adjacent carbons on the ring to form a fused 5- or 6- membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$; or, when $R^{12}$ is attached to a saturated carbon atom, it may be =O or =S; or when $R^{12}$ is attached to sulfur it may be =O.
$R^{12}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl $C_3$–$C_6$ cycloalkylmethyl —$CH_2NR^{13}R^{14}$, —$NR^{13}R^{14}$, $C_2$–$C_6$ alkoxyalkyl $C_1$–$C_4$ haloalkyl, $C_1$–$C_4$ alkoxycarbonyl, $C_1$–$C_4$ alkylcarbonyloxy, $C_1$–$C_4$ alkylcarbonyl, —$CO_2H$;
$R^{13}$ is H, $C_1$–$C_6$ alkyl, $C_3$–$C_6$ alkoxyalkyl, $C_2$–$C4$ alkenyl, phenyl, or benzyl;
$R^{14}$ is OH, H, $CF_3$, $C_1$–$C_4$ alkyl, $C_1$–$C_4$ alkoxy, $NH_2$, $C_2$–$C_4$ alkenyl, phenyl, or benzyl;
$R^{13}$ and $R^{14}$ can alternatively join to form —$(CH_2)_4$—, —$(CH_2)_5$—, —$CH_2CH_2N(R^{15})CH_2CH_2$-, or —$CH_2CH_2$—, or —$CH_2CH_2OCH_2CH_2$—;
$R^{15}$ H or methyl;
m is 0, 1, or 2.
W is selected from:
—$N(R^{22})C(=Z)N(R^{23})$—;
—$N(R^{22})C(=Z)O$—;
—$C(R^{25})(R^{26})C(=Z)C(R^{27})(R^{28})$—;
—$N(R^{22})C(=Z)C(R^{27})(R^{28})$—;
—$C(R^{25})(R^{26})C(=Z)O$—;
—$N(R^{22})C(=O)C(=O)N(R^{23})$—;
—$C(R^{25})(R^{26})C(F_2)C(R^{27})(R^{28})$—;
—$C(R^{25})(R^{26})N(CH_3)(O)C(R^{27})(R^{28})$—;
—$C(R^{25})(R^{26})N(OR^{29})C(R^{27})(R^{28})$—;
—$C(R^{25})(R^{26})C(=Z)S$—;
—$N(R^{22})S(=Z')N(R^{23})$—;
—$N(R^{22})S(=Z')_2N(R^{23})$—;
—$N(R^{22})P(=O)(R^{24a})(N(R^{23}))$—;
—$C(R^{25})(R^{26})S(=Z')C(R^{27})(R^{28})$—;
—$C(R^{25})(R^{26})S(=Z')_2C(R^{27})(R^{28})$—;
—$C(R^{25})(R^{26})P(=O)(R^{24a})C(R^{27})(R^{28})$—;
—$C(R^{25})(R^{26})S(=Z')N(R^{23})$—;
—$C(R^{25})(R^{26})S(=Z')_2N(R^{23})$—;
—$C(R^{25})(R^{26})S(=O)_2O$—;
—$C(R^{25})(R^{26})P(=O)(R^{24a})N(R^{23})$—;
—$C(R^{25})(R^{26})P(=O)(R^{24a})O$—;
—$C(R^{25})C(F_2)C(=O)N(R^{23})$—;
—$C(R^{25})C(F_2)S(=O)_2N(R^{23})$—;
—$C(R^{25})(R^{26})C(R^{34})(R^{35})C(R^{27})(R^{28})$—;
—$N=C(R^{36})N(R^{23})$—;
—$N(R^{22})P(R^{24a})N(R^{23})$—;
—$C(=Z)$—;
—$P(=O)(R^{24a})$—;
—$S(=Z')$—;
—$S(=Z')_2$—;
wherein:
Z is O, S, N-CN, N-OH, N-OCH$_3$;
Z' is oxygen:
$R^{22}$ and $R^{23}$ are independently selected from the following:
hydrogen;

$C_1$–$C_8$ alkyl substituted with 0-3 $R^{31}$;
$C_3$–$C_8$ alkenyl substituted with 0-3 $R^{31}$;
$C_3$–$C_8$ alkenyl substituted with 0-3 $R^{31}$;
$C_3$–$C_6$ cycloalkyl substituted with 0-3 $R^{31}$;
$R^{24a}$ is selected from —OH, $C_1$–$C_4$ alkoxy, mono- or di-($C_1$–$C_6$ alkyl) amino;
$R^{25}$ and $R^{27}$ are independently selected from the following:
hydrogen;
$C_1$–$C_8$ alkyl substituted with 0-3 $R^{31}$;
$C_2$–$C_8$ alkenyl substituted with 0-3 $R^{31}$;
$C_3$–$C_8$ alkenyl substituted with 0-3 $R^{31}$;
$R^{26}$ and $R^{28}$ are hydrogen or halogen;
$R^{29}$ is selected from:
hydrogen;
$C_1$–$C_2$ alkyl substituted with 0-2 $C_1$–$C_2$ alkoxy;
benzyl substituted with 0-2 halogen or $C_1$–$C_2$ alkoxy;
$R^{31}$ is selected from one or more of the following:
keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_4$ alkoxyalkyl, —$S(O)_mR^{13}$, $C_1$–$C_4$ alkyl, $C_2$–$C_4$ alkenyl, $C_3$–$C_{10}$ cycloalkyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, —$C(R^{14})=N(OR^{14})$; or
a $C_5$–$C_{14}$ saturated or partially unsaturated carbocyclic residue substituted with 0-3 $R^{32}$;
aryl substituted with 0-3 $R^{32}$; or
a 5- to 10-membered heterocyclic ring system containing 1 to 4 heteroatoms independently selected from oxygen, nitrogen or sulfur, said heterocyclic ring system being substituted with 0-2 $R^{32}$;
$R^{32}$, when a substituent on carbon, is selected from one or more of the following:
phenethyl, phenoxy, $C_3$–$C_6$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy halogen 2-(1-morpholino) ethoxy, —$CO_2R^{13}$, hydroxamic acid, —$CONR^{13}NR^{13}R^{14}$ cyano, sulfonamide, —CHO, $C_3$–$C_6$ cycloalkoxy, —$NR^{13}R^{14}$, —$C(R^{14})=N(OR^{14})$ —$NO_2$, —$OR^{13}$, —$NR^{40}R^{41}$, —$SO_mR^{13}$ —$SO_mNR^{13}R^{11}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{14}$ ($C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_2$–$C_4$ haloalkynyl, or
—$C(=O)NR^{13}C(R^{11})_2NR^{13}R^{14}$;
—$C(=O)NR^{13}C(R^{11})_2NR^{13}CO_2R^{13}$;
—$C(=O)NR^{13}$—($C_1$–$C_4$ alkyl)—$NR^{13}CO_2R^{13}$; or
—$C(=O)C(R^{11})_2NR^{13}R^{14}$;
—$C(=O)C(R^{11})_2NR^{13}CO_2R^{13}$; —$C(=O)$-($C_1$–$C_4$ alkyl)—$NR^{13}R^{14}$;
—$C(=O)$-($C_1$–$C_4$ alkyl)—$NR^{13}CO_2R^{13}$; or
$C_1$–$C_4$ alkoxy substituted with 0-3 groups selected from: $R^{11}$, $C_3$–$C_6$ cycloalkyl, —$CO_2R^{13}$, —$C(=O)NR^{13}R^{14}$, —$NR^{13}R^{14}$ or OH;
$C_1$–$C_4$ alkyl substituted with 0-3 groups selected from: $R^{11}$, =$NR^{14}$, =$NNR^{13}C(=O)NR^{13}R^{14}$ or —$NR^{13}R^{14}$;
$C_2$–$C_4$ alkenyl substituted with 0-3 $R^{11}$;
$C_2$–$C_4$ alkenyl substituted with 0-3 $R^{11}$;
a 5- or 6-membered heterocyclic ring containing from to 4 heteroatoms independently selected from oxygen, nitrogen or sulfur, substituted with 0-2 $R^{12}$;
or $R^{32}$ may be a 3- or 4- carbon chain attached to adjacent carbons on the ring to form a fused 5- or 6- membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$; or, when $R^{32}$ is attached to a saturated carbon atom, it may be =O or =S; or when $R^{12}$ is attached to sulfur it may be =O.

$R^{32}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl, —$CO_2H$, —$C(R^{14})=N(OR^{14})$;
$R^{34}$ is selected from:
hydrogen;
$C_1$–$C_2$ alkyl substituted with 0-1 $R^{11}$
$C_1$–$C_2$ alkoxy substituted with 0-1 $R^{11}$
$R^{35}$ is selected from:
hydrogen
$C_1$–$C_2$ alkyl substituted with 0-1 $R^{11}$
$C_1$–$C_2$ alkoxy substituted with 0-1 $R^{11}$
$R^{34}$ and $R^{35}$ can be taken together to form a ketal ring, a 3- to 8-membered carbocyclic ring, or a 5- or 6-membered heterocyclic ring containing 1-3 heteroatoms independently selected from the group O, N, or S;
$R^{36}$ is selected from:
$C_1$–$C_2$ alkyl substituted with 0-3 $R^{11}$;
$COR^{37}$;
$NR^{38}R^{39}$;
CN;
$R^{37}$ is selected from:
hydrogen;
$C_1$–$C_2$ alkyl substituted with 0-1 $R^{11}$;
hydroxyl;
$C_1$–$C_2$ alkoxy substituted with 0-1 $R^{11}$;
$NR^{38}R^{39}$;
$R^{38}$ and $R^{39}$ are independently selected from:
hydrogen;
$C_1$–$C_2$ alkyl substituted with 0-3 $R^{11}$; or
an amine protecting group;
$R^{40}$ is selected from: H, $C_1$–$C_3$ alkyl;
$R^{41}$ is selected from:
—$C(=O)NR^{13}R^{14}$;
—$C(=O)NR^{13}NR^{13}R^{14}$;
—$C(=O)C(R^{11})_2NR^{13}R^{14}$;
—$C(=O)C(R^{11})_2NR^{13}NR^{13}R^{14}$;
—$C(=O)C(R^{11})_2NR^{13}CO_2R^{13}$;
—$C(=O)H$;
—$C(=O)R^{11}$;
—$C(=O)$-($C_1$–$C_4$ alkyl)—$NR^{13}R^{14}$;
—$C(=O)$-($C_1$–$C_4$ alkyl)—$NR^{13}CO_2R^{13}$; or 1-3 amino acids linked together via amide bonds, and linked to the N atom via the carboxylate terminus;
provided that:
$R^4$ $R^{44}$, $R^7$ and $R^{74}$ are not all hydrogen;
when W is —$OC(=Z)O$—, —$C(=Z)$—, —$P(=O)(R^{24a})$—, —$S(=Z')$— or —$S(=Z')_2$', $R^4$ and $R^7$ are not hydrogen;
when $R^4$ and $R^{44}$ are hydrogen, at least one of the following is not hydrogen: $R^{22}$, $R^{25}$, and $R^{26}$.

[3] More preferred compounds within the scope of Formula (I) useful in the present invention include compounds of Formula (II):

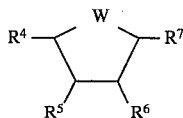

or a pharmaceutically acceptable salt thereof, wherein:

$R^4$ and $R^7$ are independently selected from the following groups:
hydrogen;
$C_1$–$C_4$ alkyl substituted with 0-3 $R^{11}$;
$C_3$–$C_4$ alkenyl substituted with 0-3 $R^{11}$;
$R^5$ is —$OR^{20}$;
$R^6$ is hydrogen or —$OR^{21}$;
$R^{20}$ and $R^{21}$ are independently hydrogen or any group that, when administered to a mammalian subject, cleaves to form a free hydroxyl;
$R^{11}$ is selected from one or more of the following:
H, halogen, —$OR^{13}$,
$C_3$–$C_{10}$ cycloalkyl substituted with 0-2 $R^{12}$;
$C_1$–$C_4$ alkyl substituted with 0-2 $R^{12}$;
aryl($C_1$–$C_3$ alkyl) substituted with 0-2 $R^{12}$;
aryl substituted with 0-3 $R^{12}$; or
a 5- to 10-membered heterocyclic ring system containing 1 to 4 heteroatoms independently selected from oxygen, nitrogen or sulfur, said heterocyclic ring system being substituted with 0-2 $R^{12}$;
$R^{12}$, when a substituent on carbon, is selected from one or more of the following:
benzyloxy, halogen, methyl, $C_1$–$C_4$ alkoxy, $CF_3$, 2-(1-morpholino)ethoxy, —$CO_2H$, hydroxamic acid, hydrazide, —$C(R^{14})$=$N(OR^{14})$, cyano, boronic acid, sulfonamide, formyl, $C_3$–$C_6$ cycloalkoxy, $C_1$–$C_4$ alkyl substituted with —$NR^{13}R^{14}$, —$NR^{13}R^{14}$, hydroxy, hydroxymethyl; or
$R^{12}$, when a substituent on nitrogen, is methyl;
$R^{13}$ is H, $C_1$–$C_4$ alkyl, $C_2$–$C_4$ alkenyl, or benzyl;
$R^{14}$ is OH, H, $CF_3$, $C_1$–$C_4$ alkyl, $C_1$–$C_4$ alkoxy, $NH_2$, $C_2$–$C_4$ alkenyl, or benzyl;
$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2$—;
$R^{15}$ is H or $CH_3$.
W is selected from:
—$N(R^{22})C(=Z)N(R^{23})$—;
—$N(R^{22})C(=Z)O$—;
—$C(R^{25})(R26)C(=Z)C(R^{27})$ (R28)—;
—$N(R^{22})S(=Z')N(R^{23})$—;
—$N(R^{22})S(=Z')_2N(R^{23})$—;
—$C(R^{25})$ $(R^{26})C(R^{34})$ $(R^{35})C(R^{27})$ $(R^{28})$—;
—$N=C(R^{36})N(R^{23})$—; or
—$C(=Z)$—;
Z is O, S, or N-CN;
Z' is O;
$R^{22}$ and $R^{23}$ are independently selected from the following:
hydrogen;
$C_1$–$C_8$ alkyl substituted with 0-3 $R^{31}$;
$C_2$–$C_6$ alkenyl substituted with 0-3 $R^{31}$;
$C_2$–$C_4$ alkenyl substituted with 0-3 $R^{31}$;
$R^{25}$ and $R^{27}$ are independently selected from the following:
hydrogen;
$C_1$–$C_4$ alkyl substituted with 0-3 $R^{31}$;
$C_2$–$C_4$ alkenyl substituted with 0-3 $R^{31}$;
$R^{26}$ and $R^{28}$ are hydrogen or halogen;
$R^{31}$ is selected from one or more of the following:
halogen, —$OR^{13}$, $C_1$–$C_4$ alkyl, $C_3$–$C_{10}$ cycloalkyl, —$C(R^{14})$=$N(OR^{14})$, —$CO_2R^{13}$, —$S(O)_mR^{13}$;
aryl substituted with 0-5 $R^{32}$; or
a 5- to 10-membered heterocyclic ring system containing 1 to 4 heteroatoms independently selected from oxygen, nitrogen or sulfur, said heterocyclic ring system being substituted with 0-2 $R^{32}$;
$R^{32}$, when a substituent on carbon, is selected from one or more of the following:
benzyloxy, halogen, 2-(1-morpholino) ethoxy, —$CO_2R^{13}$, hydroxamic acid, —$CONR^{13}NR^{13}R^{14}$, cyano boronic acid, sulfonamide, —CHO, $C_3$–$C_6$ cycloalkoxy, —$NR^{13}R^{14}$, —$C(R^{14})$=$N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$-($C_1$–$C_4$ alkyl)—$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, —$C(=O)NR^{13}R^{14}$; —$C(=O)C(R^{11})_2NR^{13}R^{14}$; —$C(=O)C(R^{11})_2NR^{13}NR^{14}$; —$C(=O)C(R^{11})_2NR^{13}CO_2R^{13}$; —$C(=O)$-($C_1$–$C_4$ alkyl) —$NR^{13}R^{14}$; —$C(=O)$-($C_1$–$C_4$ alkyl)-$NR^{13}CO_2^{R13}$; or
$C_1$–$C_4$ alkoxy substituted with 0-3 groups selected from: $R^{11}$, $C_3$–$C_6$ cycloalkyl, —$C(=O)NR^{13}R^{14}$, —$NR^{13}R^{14}$ or OH;
$C_1$–$C_4$ alkyl substituted with 0-3 groups selected from: $R^{11}$, =$NR^{14}$, =$NNR^{13}C(=O)NR^{13}R^{14}$ or —$NR^{13}R^{14}$;
$C_2$–$C_4$ alkenyl substituted with 0-3 $R^{11}$;
$C_2$–$C_4$ alkenyl substituted with 0-3 $R^{11}$;
a 5- or 6-membered heterocyclic ring containing from 1 to 4 heteroatoms independently selected from oxygen, nitrogen or sulfur;
$R^{32}$, when a substituent on nitrogen, is methyl;
m is 0, 1, 2;
$R^{34}$ is selected from:
hydrogen;
$C_1$–$C_2$ alkyl;
$C_1$–$C_2$ alkoxy;
$R^{35}$ is selected from:
hydrogen;
$C_1$–$C_2$ alkyl;
$C_1$–$C_2$ alkoxy;
$R^{36}$ is selected from: $C_1$–$C_2$ alkyl; $COR^{37}$; $NR^{38}R^{39}$; CN; $CCl_3$;
$R^{37}$ is selected from:
hydrogen; $C_1$–$C_2$ alkyl substituted with 0-1$R^{11}$; hydroxyl; $C_1$–$C_2$ alkoxy substituted with 0-1$R^{11}$; $NR^{38}R^{39}$;
$R^{38}$ and $R^{39}$ are independently selected from: hydrogen; $C_1$–$C_2$ alkyl substituted with 0-3 $R^{11}$; or an amine protecting group;
$R^{40}$ is selected from: H, $C_1$–$C_3$ alkyl; and
$R^{41}$ is selected from:
—$C(=O)NR^{13}R^{14}$;
—$C(=O)NR^{13}NR^{13}R^{14}$;
—$C(=O)C(R^{11})_2NR^{13}R^{14}$;
—$C(=O)C(R^{11})_2NR^{13}NR^{13}R^{14}$;
—$C(=O)C(R^{11})_2NR^{13}CO_2R^{13}$;
—$C(=O)H$;
—$C(=O)R^{11}$;
—$C(=O)$-($C_1$–$C_4$ alkyl) —$NR^{13}R^{14}$;
—$C(=O)$-($C_1$–$C_4$ alkyl) —$NR^{13}CO_2R^{13}$;
1-3 amino acids linked together via amide bonds, and linked to the N atom via the carboxylate terminus;
provided that:
$R^4$ and $R^7$ are not both hydrogen;

when W is —C(=Z)—, $R^4$ and $R^7$ are not hydrogen; and when $R^4$ is hydrogen, at least one of the following is not hydrogen: $R^{22}$, $R^{25}$, $R^{26}$ and $R^{28}$.

[4] Preferred compounds of Formula (II) useful in the present invention are compounds described above, wherein:

$R^4$ and $R^7$ are selected from benzyl, fluorobenzyl, pyrrolylmethyl, methoxybenzyl, isobutyl, nitrobenzyl or aminobenzyl, thienylmethyl, hydroxybenzyl;

$R^5$ is —OH;

$R^6$ is hydrogen or —OH;

$R^{13}$ is H, $C_1$–$C_4$ alkyl, $C_2$–$C_4$ alkenyl, or benzyl;

$R^{14}$ is OH, H, $CF_3$, $C_1$–$C_4$ alkyl, $C_1$–$C_4$ alkoxy, $NH_2$, $C_2$–$C_4$ alkenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

W is selected from:

—$N(R^{22})C(=O)N(R^{23})$—;

—$N(R^{22})C(=N$-$CN)N(R^{23})$—;

—$N(R^{22})S(=O)_2N(R^{23})$—;

—C(=O)—;

—$N(R^{22})C(=S)N(R^{23})$—; or

—C(=N-CN)—;

$R^{22}$ and $R^{23}$ are independently selected from the following:

hydrogen;

$C_1$–$C_8$ alkyl substituted with 0-2 $R^{31}$;

$C_2$–$C_6$ alkenyl substituted with 0-2 $R^{31}$;

$C_2$–$C_4$ alkenyl substituted with 0-2 $R^{31}$;

$R^{31}$ is selected from one or more of the following:

halogen, —$OR^{13}$, $C_1$–$C_4$ alkyl, $C_3$–$C_{10}$ cycloalkyl, —$C(R^{14})=N(OR^{14})$, —$CO_2R^{13}$, —$S(O)_mR^{13}$;

aryl substituted with 0-5 $R^{32}$; or a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, benzimidazolyl, benzotriazolyl, indazolyl, benzoxazolinyl, benzoxazolyl, said heterocyclic ring being substituted with 0-2 $R^{32}$;

$R^{32}$, when a substituent on carbon, is selected from one or more of the following:

—$CONH_2$, —$CO_2H$, CHO, $CH_2NHOH$, —$CH_2NR^{13}R^{14}$, $NR^{13}R^{14}$, hydroxy, hydroxymethyl, —$C(R^{14})=N(OR^{14})$, halogen, methoxy, methyl, nitro, cyano, allyloxy, —$CO_2CH_3$, —NHCHO, —$NHCOCH_3$, —$OCO_2CH_3$, —CH=$NCH_2CH_2OH$, —$OCONHCH_2C_6H_5$, —OCONHCH_3, oxazolidinyl, —C≡C—$CH_2OH$, —$COCH_3$, hydroxyethyl, $C_1$–$C_3$ alkyl (said alkyl substituted with 0-4 halogen, or OH), tetrazolyl, —$OCH_2CONH_2$, —$CONHNH_2$, —CH=$NNHCONH_2$, —$CONHOCH_3$, —$CH_2CH(OH)CH_2OH$, adamantamido, hydroxyethoxy, dihydroxyethyl, —$C(NH_2)=NH$, —$CONHCH_3$, —$B(OH)_2$, benzyloxy, —$CONHCH_2CH_3$, —$CON(CH_2CH_3)_2$, methylthio, —$SO_2CH_3$, —NH-$CONH_2$, —$NHCONHCH_3$, —$NHCOCH_2N(CH_3)_2$, —$NHCOCH_2NHCH_3$, —$NHCOCH_2NHCO_2CH_2C_6H_5$, —$NHCOCH_2NH_2$, —$NHCOCH(CH_3)NHCO_2CH_2C_6H_5$, —$NHCOCH(CH_2C_6H_5)NHCO_2CH_2C_6H_5$, —$NHCOCH(CH_3)NH_2$, —$NHCOCH(CH_2C_6H_5)NH_2$, —$CO_2CH_2CH_3$, —$CONHCH_2CH_2CH_3$, —$CONHCH(CH_3)_2$, —$CH_2$-imidazole, —$COC(CH_3)_3$, —$CH(OH)CF_3$, —CO-imidazole, —CO-pyrazolyl, oxadiazolidinonyl, —$COCF_3$, —$COCH_2CH_3$, —$COCH_2CH_2CH_3$, pyrazolyl, —$SO_2NH_2$, —$C(CH_2CH_3)=N(OH)$ or —$C(CF_3)=N(OH)$, phenyl, acetoxy, hydroxyamino, —$N(CH_3)$ (CHO), cyclopropylmethoxy, —$CONR^{13}R^{14}$, —CONHOH, (diethylaminoethyl) aminocarbonyl, (N-ethyl, N-methylaminoethyl) aminocarbonyl, (4-methylpiperaz inylethyl) aminocarbonyl, pyrrolidinylethyl) aminocarbonyl, (piperidinylethyl) aminocarbonyl, —$NHCOCH_2NHCH_3$, N-(2-(4-morpholino)-ethyl) aminocarbonyl, N-(2-(N,N-dimethylamino) ethyl) aminocarbonyl;

$R^{32}$, when a substituent on nitrogen, is methyl.

[5] Other preferred compounds useful in the invention within the scope of Formula (I) are compounds of Formula (II) having the formula:

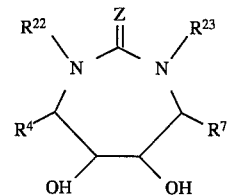

wherein:

Z is O, S, or N-CN;

$R^4$ and $R^7$ are independently selected from: benzyl, fluorobenzyl, pyrrolylmethyl, methoxybenzyl, isobutyl, nitrobenzyl or aminobenzyl, thienylmethyl, hydroxybenzyl;

$R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl) ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, (HONHC(=O))-benzyl, ($CH_3NHC(=O)$)-benzyl, N,N-dimethylaminocarbonylbenzyl, ($HOCH_2CH(OH)CH_2O$)- benzyl, benzyl, hydroxyethoxybenzyl (oxazolidinyl)-benzyl, (hydroxyl) hexyl, hexenyl, (hydroxy) octyl, (hydroxyl) pentyl, (carboxy) pentyl, (carbomethoxy) pentyl, (methylthio) benzyl, (methylsulfonyl) benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl) alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N, N-diisopropylaminocarbonylbenzyl, N, N-di-n-propylaminocarbonylbenzyl, (hydroxypropynyl) benzyl, (imidazolyl—C (=O))-benzyl, (pyrazolyl-C(=O))-benzyl, (pyridylmethylaminocarbonyl) benzyl, (oxadiazolidinonyl) benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C$(=NOH))-benzyl, (trifluorohydroxyethyl) benzyl, ($CF_3C$(=NOH))-benzyl, (N-methylglycyl) aminobenzyl, ((4-morpholino)ethyl)aminocarbonylbenzyl, (N,N-dimethylaminoethyl)aminocarbonylbenzyl, (N,N-diethylaminoethyl) aminocarbonylbenzyl, (4-methylpiperazin-1-ylethyl)aminocarbonylbenzyl, (benzyl—NHC(=O)O)benzyl, ($CH_3NHC$ (=O)O) benzyl, ($NH_2C$(=O)$CH_2O$)benzyl, ($NH_2C$(=NH)) benzyl, ((N-phenylmethoxycarbonyl) glycylamino) benzyl, (imidazolylmethyl) benzyl, (($CH_3)_3C$-C (=O)) benzyl, (N-methyl-N-ethylaminoethyl) aminocarbonylbenzyl, (pyrrolidinylethyl) aminocarbonylbenzyl, (piperidinylethyl) aminocarbonylbenzyl, ($H_2NC$(=NOH)) benzyl, ($H_2NC$ (=NOH)) fluorobenzyl, benzimidazolylmethyl, benzotriazolylmethyl, indazolylmethyl, benzoxazolinylmethyl, benzisoxazolylmethyl, thienylmethyl, furylmethyl.

[6] Still other preferred compounds useful in the invention within the scope of Formula (I) are compounds of Formula (IIa):

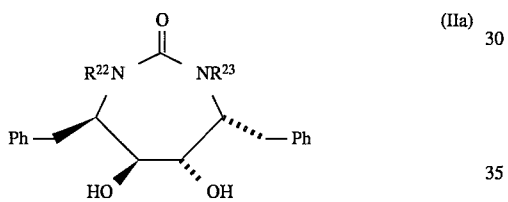

wherein $R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC$(=O))-benzyl, carbomethoxybenzyl, carboethoxybenzyl, tetrazolylbenzyl, and dimethylallyl, aminomethylbenzyl, (O-benzyl-formaldoxime) benzyl, (O-methyl-formaldoxime) benzyl, ($CH_3O_2CO$) -benzyl, ($HOCH_2CH_2N$=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl) ethylbenzyl, ($CH_3C$(=NOH))-benzyl, ($H_2NNHC$(=O))-benzyl, ($H_2NC$(=O)NHN=CH)-benzyl, ($CH_3ONHC$(=O))-benzyl, (HONHC(=O))-benzyl, ($CH_3NHC$(=O))-benzyl, N,N-dimethylaminocarbonylbenzyl, ($HOCH_2CH(OH)CH_2$ O)-benzyl, hydroxyethoxybenzyl (oxazolidinyl)-benzyl, (hydroxyl) hexyl, hexenyl, (hydroxy) octyl, (hydroxyl) pentyl, (carboxy) pentyl, (carbomethoxy) pentyl, (methylthio) benzyl, (methylsulfonyl) benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl) alanylaminobenzyl, phenylalanylaminobenzyl, (N-phenylmethoxycarbonyl) phenylalanylaminobenzyl, ($CH_3CH_2NHC$ (=O)) -benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl—C(=O))-benzyl, (pyrazolyl—C(=O))-benzyl, (pyridylmethylaminocarbonyl) benzyl, (oxadiazolidinonyl) benzyl, trifluoroacetylbenzyl, (pyrazolyl)-benzyl, ($H_2NSO_2$)-benzyl, dihydroxyethylbenzyl, (MeHNC(=O)NH)-benzyl, ($H_2NC$(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C$ (=NOH))-benzyl, (trifluorohydroxyethyl) benzyl, ($CF_3C$(=NOH))-benzyl, (N-methylglycyl) aminobenzyl, ((4-morpholino)-ethyl) aminocarbonylbenzyl, (N,N-dimethylaminoethyl) aminocarbonylbenzyl, (N,N-diethylaminoethyl) aminocarbonylbenzyl, (4-methylpiperazin-1-ylethyl) aminocarbonylbenzyl, (benzyl-NHC (=O)O)benzyl, ($CH_3NHC$(=O)O)benzyl, ($NH_2C$(=O)$CH_2O$)benzyl, ($NH_2C$(=NH))benzyl, ((N-phenylmethoxycarbonyl) glycylamino) benzyl, (imidazolylmethyl) benzyl, (($CH_2)_3C$-C (=O))benzyl, (N-methyl-N-ethylaminoethyl) aminocarbonylbenzyl, (pyrrolidinylethyl) aminocarbonylbenzyl, (piperidinylethyl) aminocarbonylbenzyl, ($H_2NC$(=NOH))benzyl, ($H_2NC$(=NOH))fluorobenzyl, benzimidazolylmethyl, benzotriazolylmethyl, indazolylmethyl, benzoxazolinylmethyl, benzisoxazolylmethyl, thienylmethyl, furylmethyl.

[7] Specifically preferred compounds useful in the invention within the scope of Formula (I) are compounds having the Formula (IIa):

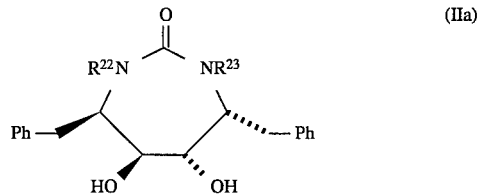

selected from the group consisting of:

the compound of Formula (IIa) wherein $R^{22}$ is allyl and $R^{23}$ is allyl;

the compound of Formula (IIa) wherein $R^{22}$ is propyl and $R^{23}$ is propyl;

the compound of Formula (IIa) wherein $R^{22}$ is cyclopropylmethyl and $R^{23}$ is cyclopropylmethyl;

the compound of Formula (IIa) wherein $R^{22}$ is n-hexyl and $R^{23}$ is n-hexyl;

the compound of Formula (IIa) wherein $R^{22}$ is n-butyl and $R^{23}$ is n-butyl;

the compound of Formula (IIa) wherein $R^{22}$ is $CH_2CH=C(CH_3)_2$ and $R^{23}$ is $CH_2CH=C(CH_3)_2$;

the compound of Formula (IIa) wherein $R^{22}$ is $CH_2CH=C(CH_3)_2$ and $R^{23}$ is H;

the compound of Formula (IIa) wherein $R^{22}$ is i-pentyl and $R^{23}$ is i-pentyl;

the compound of Formula (IIa) wherein $R^{22}$ is 2-methallyl and $R^{23}$ is 2-methallyl;

the compound of Formula (IIa) wherein $R^{22}$ is n-pentyl and $R^{23}$ is n-pentyl;

the compound of Formula (IIa) wherein $R^{22}$ is benzyl and $R^{23}$ is benzyl;

the compound of Formula (IIa) wherein $R^{22}$ is i-hexyl and $R^{23}$ is i-hexyl;

the compound of Formula (IIa) wherein $R^{22}$ is allyl and $R^{23}$ is isoprenyl;

the compound of Formula (IIa) wherein $R^{22}$ is 1-cinnamyl and $R^{23}$ is 1-cinnamyl;

the compound of Formula (IIa) wherein $R^{22}$ is 4-fluorobenzyl and $R^{23}$ is 4-fluorobenzyl;

the compound of Formula (IIa) wherein $R^{22}$ is cyclopropylmethyl and $R^{23}$ is benzyl;

the compound of Formula (IIa) wherein $R^{22}$ is allyl and $R^{23}$ is benzyl;

the compound of Formula (IIa) wherein $R^{22}$ is $CH_2CH=C(CH_3)_2$ and $R^{23}$ is cyclopropylmethyl;

the compound of Formula (IIa) wherein $R^{22}$ is 2-naphthylmethyl and $R^{23}$ is 2-napthylmethyl;

the compound of Formula (IIa) wherein $R^{22}$ is n-butyl and $R^{23}$ is benzyl;

the compound of Formula (IIa) wherein $R^{22}$ is allyl and $R^{23}$ is cyclopropylmethyl;

the compound of Formula (IIa) wherein $R^{22}$ is n-butyl and $R^{23}$ is cyclopropylmethyl;

the compound of Formula (IIa) wherein $R^{22}$ is $CH_2CH=C(CH_3)_2$ and $R^{23}$ is benzyl;

the compound of Formula (IIa) wherein $R^{22}$ is benzyl and $R^{23}$ is ethyl;

the compound of Formula (IIa) wherein $R^{22}$ is benzyl and $R^{23}$ is 4-pyridinylmethyl;

the compound of Formula (IIa) wherein $R^{22}$ is cyclopropylmethyl and $R^{23}$ is 4-pyridinylmethyl;

the compound of Formula (IIa) wherein $R^{22}$ is benzyl and $R^{23}$ is cyclopentylmethyl;

the compound of Formula (IIa) wherein $R^{22}$ is cyclopropylmethyl and $R^{23}$ is cyclopentylmethyl;

the compound of Formula (IIa) wherein $R^{22}$ is benzyl and $R^{23}$ is n-propyl;

the compound of Formula (IIa) wherein $R^{22}$ is cyclopropylmethyl and $R^{23}$ is cinnamyl;

the compound of Formula (IIa) wherein $R^{22}$ is cyclopropylmethyl and $R^{23}$ is 2-naphthylmethyl;

the compound of Formula (IIa) wherein $R^{22}$ is cyclopentylmethyl and $R^{23}$ is 2-naphthylmethyl;

the compound of Formula (IIa) wherein $R^{22}$ is benzyl and $R^{23}$ is 2-naphthylmethyl;

the compound of Formula (IIa) wherein $R^{22}$ is cyclopropylmethyl and $R^{23}$ is 2-pyridinylmethyl;

the compound of Formula (IIa) wherein $R^{22}$ is 3-cyanobenzyl and $R^{23}$ is 3-cyanobenzyl;

the compound of Formula (IIa) wherein $R^{22}$ is allyl and $R^{23}$ is 2-naphthylmethyl;

the compound of Formula (IIa) wherein $R^{22}$ is n-propyl and $R^{23}$ is 2-naphthylmethyl;

the compound of Formula (IIa) wherein $R^{22}$ is n-butyl and $R^{23}$ is 2-naphthylmethyl;

the compound of Formula (IIa) wherein $R^{22}$ is hydrogen and $R^{23}$ is 2-naphthylmethyl;

the compound of Formula (IIa) wherein $R^{22}$ is 4-pyridinylmethyl and $R^{23}$ is 2-naphthylmethyl;

the compound of Formula (IIa) wherein $R^{22}$ is allyl and $R^{23}$ is cyclopentylmethyl;

the compound of Formula (IIa) wherein $R^{22}$ is allyl and $R^{23}$ is 2-quinolinylmethyl;

the compound of Formula (IIa) wherein $R^{22}$ is 3-pyridinylmethyl and $R^{23}$ is cyclopropylmethyl;

the compound of Formula (IIa) wherein $R^{22}$ is 3-pyridinylmethyl and $R^{23}$ is 2-naphthylmethyl;

the compound of Formula (IIa) wherein $R^{22}$ is 3-hydroxybenzyl and $R^{23}$ is 3-hydroxybenzyl;

the compound of Formula (IIa) wherein $R^{22}$ is vinylbenzyl and $R^{23}$ is vinylbenzyl;

the compound of Formula (IIa) wherein $R^{22}$ is 3-allyloxybenzyl and $R^{23}$ is 3-hydroxybenzyl;

the compound of Formula (IIa) wherein $R^{22}$ is 3-pyridinylmethyl and $R^{23}$ is 3-pyridinylmethyl;

the compound of Formula (IIa) wherein $R^{22}$ is 2-naphthylmethyl and $R^{23}$ is 4-fluorobenzyl;

the compound of Formula (IIa) wherein $R^{22}$ is 4-hydroxybenzyl and $R^{23}$ is 4-hydroxybenzyl;

the compound of Formula (IIa) wherein $R^{22}$ is 3-hydroxymethylbenzyl and $R^{23}$ is 3-hydroxymethylbenzyl;

the compound of Formula (IIa) wherein $R^{22}$ is 3-carbomethoxybenzyl and $R^{23}$ is 3-carbomethoxybenzyl;

the compound of Formula (IIa) wherein $R^{22}$ is 4-hydroxymethylbenzyl and $R^{23}$ is 4-hydroxymethylbenzyl;

the compound of Formula (IIa) wherein $R^{22}$ is 3-formylbenzyl and $R^{23}$ is 3-formylbenzyl;

the compound of Formula (IIa) wherein $R^{22}$ is 4-cyanobenzyl and $R^{23}$ is 4-cyanobenzyl;

the compound of Formula (IIa) wherein $R^{22}$ is 4-formylbenzyl and $R^{23}$ is 4-formylbenzyl;

the compound of Formula (IIa) wherein $R^{22}$ is 4-hydroxybenzyl and $R^{23}$ is 2-propyl;

the compound of Formula (IIa) wherein $R^{22}$ is 3-hydroxybenzyl and $R^{23}$ is 2-propyl;

the compound of Formula (IIa) wherein $R^{22}$ is 3-carboxybenzyl and $R^{23}$ is 3-carboxybenzyl;

the compound of Formula (IIa) wherein $R^{22}$ is 3-formaldoximebenzyl and $R^{23}$ is 3-formaldoximebenzyl;

the compound of Formula (IIa) wherein $R^{22}$ is cyclopropylmethyl and $R^{23}$ is 3-hydroxybenzyl;

the compound of Formula (IIa) wherein $R^{22}$ is cyclopropylmethyl and $R^{23}$ is 4-hydroxybenzyl;

the compound of Formula (IIa) wherein $R^{22}$ is cyclobutylmethyl and $R^{23}$ is cyclobutylmethyl;

the compound of Formula (IIa) wherein $R^{22}$ is cyclopentylmethyl and $R^{23}$ is cyclopentylmethyl;

the compound of Formula (IIa) wherein $R^{22}$ is 3 n-butyl and $R^{23}$ is $CH_2CH=C(CH_3)_2$;

the compound of Formula (IIa) wherein $R^{22}$ is n-butyl and $R^{23}$ is cyclopentylmethyl;

the compound of Formula (IIa) wherein $R^{22}$ is benzyl and $R^{23}$ is H;

the compound of Formula (IIa) wherein $R^{22}$ is 3-fluorobenzyl and $R^{23}$ is 3-fluorobenzyl;

the compound of Formula (IIa) wherein $R^{22}$ is 3-methoxybenzyl and $R^{23}$ is 3-methoxybenzyl;

the compound of Formula (IIa) wherein $R^{22}$ is 3,4-difluorobenzyl and $R^{23}$ is 3,4-difluorobenzyl;

the compound of Formula (IIa) wherein $R^{22}$ is 4-methylbenzyl and $R^{23}$ is 4-methylbenzyl;

the compound of Formula (IIa) wherein $R^{22}$ is 4-chlorobenzyl and $R^{23}$ is 4-chlorobenzyl;

the compound of Formula (IIa) wherein $R^{22}$ is cyclopropylmethyl and $R^{23}$ is 4-fluorobenzyl;

the compound of Formula (IIa) wherein $R^{22}$ is 3-chlorobenzyl and $R^{23}$ is 3-chlorobenzyl;

the compound of Formula (IIa) wherein $R^{22}$ is 3-nitrobenzyl and $R^{23}$ is 3-nitrobenzyl;

the compound of Formula (IIa) wherein $R^{22}$ is 3-methylbenzyl and $R^{23}$ is 3-methylbenzyl;

the compound of Formula (IIa) wherein $R^{22}$ is 3-bromobenzyl and $R^{23}$ is 3-bromobenzyl;

the compound of Formula (IIa) wherein $R^{22}$ is 4-fluorobenzyl and $R^{23}$ is H;

the compound of Formula (IIa) wherein $R^{22}$ is cyclopropylmethyl and $R^{23}$ is 3-chlorobenzyl;

the compound of Formula (IIa) wherein $R^{22}$ is 3-aminobenzyl and $R^{23}$ is 3-aminobenzyl;

the compound of formula (IIa) wherein $R^{22}$ is 4-aminobenzyl and $R^{23}$ is 4-aminobenzyl;

the compound of Formula (IIa) wherein $R^{22}$ is 3-nitrobenzyl and $R^{23}$ is H;

the compound of Formula (IIa) wherein $R^{22}$ is 3-(NHCHO) benzyl and $R^{23}$ is 3-(NHCHO)benzyl;

the compound of Formula (IIa) wherein $R^{22}$ is 3-(NHCOCH$_3$)benzyl and $R^{23}$ is 3-(NHCOCH$_3$)benzyl;

the compound of Formula (IIa) wherein $R^{22}$ is 3,4-dihydroxybenzyl and $R^{23}$ is 3,4-dihydroxybenzyl;

the compound of Formula (IIa) wherein $R^{22}$ is 3-formaldoximebenzyl and $R^{23}$ is 3-(N-hydroxy)aminomethylbenzyl;

the compound of Formula (IIa) wherein $R^{22}$ is 3-(N-hydroxy) aminomethylbenzyl and $R^{23}$ is 3-(N-hydroxy) aminomethylbenzyl;

the compound of Formula (IIa) wherein $R^{22}$ is 3-(CH$_3$OC(=O)O-)benzyl and $R^{23}$ is 3-(CH$_3$OC(=O)O-)benzyl;

the compound of Formula (IIa) wherein $R^{22}$ is 3-(1-hydroxyethyl)benzyl and $R^{23}$ is 3-(1-hydroxyethyl)benzyl;

the compound of Formula (IIa) wherein $R^{22}$ is 3-(HOCH$_2$CH$_2$N=CH)benzyl and $R^{23}$ is 3-(HOCH$_2$CH$_2$N=CH)benzyl;

the compound of Formula (IIa) wherein $R^{22}$ is 3-(HOCH$_2$CH$_2$N=CH) benzyl and $R^{23}$ is 3-(2-oxazolidinyl)benzyl;

the compound of Formula (IIa) wherein $R^{22}$ is 3-(C$_6$H$_5$CH$_2$NHC(=O)O)benzyl and $R^{23}$ is 3-(C$_6$H$_5$CH$_2$NHC(=O)O)benzyl;

the compound of Formula (IIa) wherein $R^{22}$ is 3-(CH$_3$NHC(=O)O)benzyl and $R^{23}$ is 3-(CH$_3$NHC(=O)O)benzyl;

the compound of Formula (IIa) wherein $R^{22}$ is 3-(HOCH$_2$CC)benzyl and $R^{23}$ is 3-bromobenzyl;

the compound of Formula (IIa) wherein $R^{22}$ is 3-acetylbenzyl and $R^{23}$ is 3-bromobenzyl;

the compound of Formula (IIa) wherein $R^{22}$ is 3-acetylbenzyl and $R^{23}$ is 3-acetylbenzyl;

the compound of Formula (IIa) wherein $R^{22}$ is 3-(CH$_3$C(=NOH))benzyl and $R^{23}$ is 3-(CH$_3$C(=NOH))benzyl;

the compound of Formula (IIa) wherein $R^{22}$ is 3-(1-hydroxyethyl)benzyl and $R^{23}$ is 3-bromobenzyl;

the compound of Formula (IIa) wherein $R^{22}$ is 3-(chloromethyl) benzyl and $R^{23}$ is 3-(chloromethyl) benzyl;

the compound of Formula (IIa) wherein $R^{22}$ is 3-(5-tetrazolyl)benzyl and $R^{23}$ is cyclopropylmethyl;

the compound of Formula (IIa) wherein $R^{22}$ is 3-cyanobenzyl and $R^{23}$ is 3-formylbenzyl;

the compound of Formula (IIa) wherein $R^{22}$ is 4-acetoxybenzyl and $R^{23}$ is 4-hydroxybenzyl;

the compound of Formula (IIa) wherein $R^{22}$ is 3-aminocarbonylbenzyl and $R^{23}$ is 3-aminocarbonylbenzyl;

the compound of Formula (IIa) wherein $R^{22}$ is 3-(H$_2$NCOCH$_2$O)benzyl and $R^{23}$ is 3-(H$_2$NCOCH$_{2O}$)benzyl;

the compound of Formula (IIa) wherein $R^{22}$ is 3-hydroxybenzyl and $R^{23}$ is H;

the compound of Formula (IIa) wherein $R^{22}$ is 3-methylbenzyl and $R^{23}$ is 3-hydroxybenzyl;

the compound of Formula (IIa) wherein $R^{22}$ is 2-naphthylmethyl and $R^{23}$ is 3-hydroxybenzyl;

the compound of Formula (IIa) wherein $R^{22}$ is 3-(H$_2$NNHC(=O))-benzyl and $R^{23}$ is 3-(H$_2$NNHC(=O))-benzyl;

the compound of Formula (IIa) wherein $R^{22}$ is 4-(H$_2$NNHC(=O))-benzyl and $R^{23}$ is 4-(H$_2$NNHC(=O))-benzyl;

the compound of Formula (IIa) wherein $R^{22}$ is 4-hydroxymethylbenzyl and $R^{23}$ is 3-hydroxybenzyl;

the compound of Formula (IIa) wherein $R^{22}$ is 3-(H$_2$NC(=O)NHN=CH)-benzyl and $R^{23}$ is 3-(H$_2$NC(=O)NHN=CH)-benzyl;

the compound of Formula (IIa) wherein $R^{22}$ is 3-[(N-methoxy) aminocarbonyl]-benzyl and $R^{23}$ is 3-[(N-methoxy) aminocarbonyl]-benzyl;

the compound of Formula (IIa) wherein $R^{22}$ is 4-[(N-methoxy) aminocarbonyl]-benzyl and $R^{23}$ is 4-[(N-methoxy) aminocarbonyl]-benzyl;

the compound of Formula (IIa) wherein $R^{22}$ is 3-(HOCH$_2$CH(OH)CH$_2$O)benzyl and $R^{23}$ is 3-(HOCH$_2$CH(OH)CH$_2$O)benzyl;

the compound of Formula (IIa) wherein $R^{22}$ is 3-(2-hydroxyethoxy)benzyl and $R^{23}$ is 3-(2-hydroxyethoxy) benzyl;

the compound of Formula (IIa) wherein $R^{22}$ is 3-(1,2-dihydroxyethyl)benzyl and $R^{23}$ is 4-(1,2-dihydroxyethyl) benzyl;

the compound of Formula (IIa) wherein $R^{22}$ is 3-aminocarbonylbenzyl and $R^{23}$ is 3-(H$_2$NC(=NH))benzyl;

the compound of Formula (IIa) wherein $R^{22}$ is 4-hydroxybenzyl and $R^{23}$ is 3-formyl-4-hydroxybenzyl;

the compound of Formula (IIa) wherein $R^{22}$ is 3-carbomethoxybenzyl and $R^{23}$ is 3-(N-methylaminocarbonyl)benzyl;

the compound of Formula (IIa) wherein $R^{22}$ is 3-(N-methylaminocarbonyl)benzyl and $R^{23}$ is 3-(N-methylaminocarbonyl)benzyl;

the compound of Formula (IIa) wherein $R^{22}$ is benzyl and $R^{23}$ is 3-hydroxybenzyl;

the compound of Formula (IIa) wherein $R^{22}$ is 2-naphthylmethyl and $R^{23}$ is 4-hydroxymethylbenzyl;

the compound of Formula (IIa) wherein $R^{22}$ is 3-(1,2-dihydroxyethyl)benzyl and $R^{23}$ is 3-(1,2-dihydroxyethyl)benzyl;

the compound of Formula (IIa) wherein $R^{22}$ is 4-(1,2-dihydroxyethyl)benzyl and $R^{23}$ is 4-(1,2-dihydroxyethyl)benzyl;

the compound of Formula (IIa) wherein $R^{22}$ is 3-hydroxymethylbenzyl and $R^{23}$ is 3-(N-methylaminocarbonyl)benzyl;

the compound of Formula (IIa) wherein $R^{22}$ is 4-hydroxymethylbenzyl and $R^{23}$ is hydrogen;

the compound of Formula (IIa) wherein $R^{22}$ is 3-(boronic acid)benzyl and $R^{23}$ is 3-(boronic acid)benzyl;

the compound of Formula (IIa) wherein $R^{22}$ is 3-nitrobenzyl and $R^{23}$ is 3-benzyloxybenzyl;

the compound of Formula (IIa) wherein $R^{22}$ is 3-aminobenzyl and $R^{23}$ is 3-hydroxybenzyl;

the compound of Formula (IIa) wherein $R^{22}$ is 3-(N-ethylaminocarbonyl)benzyl and $R^{23}$ is 3-(N-ethylaminocarbonyl)benzyl;

the compound of Formula (IIa) wherein $R^{22}$ is 3-carbomethoxybenzyl and $R^{23}$ is 3-(N,N-diethylaminocarbonyl)benzyl;

the compound of Formula (IIa) wherein $R^{22}$ is 3-carbomethoxybenzyl and $R^{23}$ is 3-(N-ethylaminocarbonyl)benzyl;

the compound of Formula (IIa) wherein $R^{22}$ is 6-hydroxy-1-hexyl and $R^{23}$ is hydrogen;

the compound of Formula (IIa) wherein $R^{22}$ is 6-hydroxy-1-hexyl and $R^{23}$ is 6-hydroxy-1-hexyl;

the compound of Formula (IIa) wherein $R^{22}$ is cyclopropylmethyl and $R^{23}$ is 6-hydroxy-1-hexyl;

the compound of Formula (IIa) wherein $R^{22}$ is 5-carboxy-1-pentyl and $R^{23}$ is 5-carboxy-1-pentyl;

the compound of Formula (IIa) wherein $R^{22}$ is 3-iodobenzyl and $R^{23}$ is 3-iodobenzyl;

the compound of Formula (IIa) wherein $R^{22}$ is benzyl and $R^{23}$ is 2-(hydroxymethyl)-cyclopropylmethyl;

the compound of Formula (IIa) wherein $R^{22}$ is 3-(thiomethyl)benzyl and $R^{23}$ is 3-(thiomethyl)benzyl;

the compound of Formula (IIa) wherein $R^{22}$ is 3-(methylsulfonyl)benzyl and $R^{23}$ is 3-(methylsulfonyl)benzyl;

the compound of Formula (IIa) wherein $R^{22}$ is 6-hexenyl and $R^{23}$ is 6-hexenyl;

the compound of Formula (IIa) wherein $R^{22}$ is 6-bromo-5-hydroxy-1-hexyl and $R^{23}$ is 6-bromo-5-hydroxy-1-hexyl;

the compound of Formula (IIa) wherein $R^{22}$ is 5-hydroxy-1-pentyl and $R^{23}$ is 5-hydroxy-1-pentyl;

the compound of Formula (IIa) wherein $R^{22}$ is 3-aminobenzyl and $R^{23}$ is 4-hydroxymethylbenzyl;

the compound of Formula (IIa) wherein $R^{22}$ is 3-($H_2NC(=O)NH$)benzyl and $R^{23}$ is 3-($H_2NC(=O)NH$)benzyl;

the compound of Formula (IIa) wherein $R^{22}$ is 3-(N-methylamino)benzyl and $R^{23}$ is 3-(N-methylamino)benzyl;

the compound of Formula (IIa) wherein $R^{22}$ is cyclopropylmethyl and $R^{23}$ is 3-aminobenzyl;

the compound of Formula (IIa) wherein $R^{22}$ is cyclopropylmethyl and $R^{23}$ is 3-nitrobenzyl;

the compound of Formula (IIa) wherein $R^{22}$ is 3-(N,N-dimethylamino)benzyl and $R^{23}$ is 3-(N,N-dimethylamino)benzyl;

the compound of Formula (IIa) wherein $R^{22}$ is 3-nitrobenzyl and $R^{23}$ is 4-hydroxymethylbenzyl;

the compound of Formula (IIa) wherein $R^{22}$ is 3-aminobenzyl and $R^{23}$ is 3-($CH_3NHC(=O)NH$)benzyl;

the compound of Formula (IIa) wherein $R^{22}$ is 3-($CH_3NHC(=O)NH$)benzyl and $R^{23}$ is 3-($CH_3NHC(=O)NH$)benzyl;

the compound of Formula (IIa) wherein $R^{22}$ is 3-(N-methylamino)benzyl and $R^{23}$ is 4-hydroxymethylbenzyl;

the compound of Formula (IIa) wherein $R^{22}$ is 3-((N,N-dimethylaminoglycyl)amino)benzyl and $R^{23}$ is 3-((N,N-dimethylaminoglycyl)amino)benzyl;

the compound of Formula (IIa) wherein $R^{22}$ is 3-((N-methylaminoglycyl)amino)benzyl and $R^{23}$ is 3-((N-methylaminoglycyl)amino)benzyl;

the compound of Formula (IIa) wherein $R^{22}$ is 3—((N,N-dimethylaminoglycyl)amino)benzyl and $R^{23}$ is 4-hydroxymethylbenzyl;

the compound of Formula (IIa) wherein $R^{22}$ is 3-((N-phenylmel and $R^{23}$ is cyclopropylmethyl;

the compound of Formula (IIa) wherein $R^{22}$ is 5-hydroxy-1-pentyl and $R^{23}$ is 5-methoxy-1-pentyl;

the compound of Formula (IIa) wherein $R^{22}$ is 5-hydroxy-1-pentyl and $R^{23}$ is 3-cyanobenzyl;

the compound of Formula (IIa) wherein $R^{22}$ is 5-hydroxy-1-pentyl and $R^{23}$ is 3-carboethoxybenzyl; thoxycarbonylaminoglycyl)amino)benzyl and $R^{23}$ is 3-((N-phenylmethoxycarbonylamino-glycyl)amino)benzyl;

the compound of Formula (IIa) wherein $R^{22}$ is 3-(glycylamino)benzyl and $R^{23}$ is 3-(glycylamino)benzyl;

the compound of Formula (IIa) wherein $R^{22}$ is 3-(glycylamino)benzyl and $R^{23}$ is 4-hydroxymethylbenzyl;

the compound of Formula (IIa) wherein $R^{22}$ is 3-((N-phenylmethoxycarbonylamino-L-alanyl)amino)benzyl and $R^{23}$ is 3-((N-phenylmethoxycarbonylamino-L-alanyl)amino)benzyl;

the compound of Formula (IIa) wherein $R^{22}$ is 3-((N-phenylmethoxycarbonylamino-L-phenylalanyl)amino)benzyl and $R^{23}$ is 3-((N-phenylmethoxycarbonylamino-L-phenylalanyl)amino)benzyl;

the compound of Formula (IIa) wherein $R^{22}$ is 3-(L-alanyl)amino)benzyl and $R^{23}$ is 3-(L-alanyl)amino)benzyl;

the compound of Formula (IIa) wherein $R^{22}$ is 3-(L-phenylalanyl)amino)benzyl and $R^{23}$ is 3-(L-phenylalanyl)amino)benzyl;

the compound of Formula (IIa) wherein $R^{22}$ is 5-hydroxy-1-pentyl and $R^{23}$ is hydrogen;

the compound of Formula (IIa) wherein $R^{22}$ is 5-hydroxy-1-pentyl and $R^{23}$ is 2-naphthylmethyl;

the compound of Formula (IIa) wherein $R^{22}$ is 5-hydroxy-1-pentyl and $R^{23}$ is benzyl;

the compound of Formula (IIa) wherein $R^{22}$ is 5-hydroxy-1-pentyl and $R^{23}$ is 4-hydroxymethylbenzyl;

the compound of Formula (IIa) wherein $R^{22}$ is 6-hydroxy-1-hexyl and $R^{23}$ is 2-naphthylmethyl;

the compound of Formula (IIa) wherein $R^{22}$ is 5-hydroxy-1-pentyl and $R^{23}$ is 3-hydroxybenzyl;

the compound of Formula (IIa) wherein $R^{22}$ is 5-hydroxy-1-pentyl and $R^{23}$ is (5-methylsulfonyl)-1-pentyl;

the compound of Formula (IIa) wherein $R^{22}$ is 5-hydroxy-1-pentyl and $R^{23}$ is 5-($CH_3S(O)$)-1-pentyl;

the compound of Formula (IIa) wherein $R^{22}$ is 5-hydroxy-1-penty the compound of Formula (IIa) wherein $R^{22}$ is 4-hydroxy-1-hexyl and $R^{23}$ is 4-hydroxy-1-hexyl;

the compound of Formula (IIa) wherein $R^{22}$ is 4-hydroxy-1-hexyl and $R^{23}$ is 2-naphthylmethyl;

the compound of Formula (IIa) wherein $R^{22}$ is 4-oxime-1-hexyl and $R^{23}$ is 4-oxime-1-hexyl;

the compound of Formula (IIa) wherein $R^{22}$ is 5-hydroxy-1-pentyl and $R^{23}$ is 3-hydroxymethylbenzyl;

the compound of Formula (IIa) wherein $R^{22}$ is 6-amino-1-hexyl and $R^{23}$ is 4-hydroxymethylbenzyl;

the compound of Formula (IIa) wherein $R^{22}$ is 3-(N,N-diethylaminocarbonyl)benzyl and $R^{23}$ is 3-(N,N-diethylaminocarbonyl) benzyl;

the compound of Formula (IIa) wherein $R^{22}$ is 3-carbomethoxybenzyl and $R^{23}$ is 3-(N,N-diethylaminocarbonyl)benzyl;

the compound of Formula (IIa) wherein $R^{22}$ is 3-carbomethoxybenzyl and $R^{23}$ is 3-(N-ethylaminocarbonyl)benzyl;

the compound of Formula (IIa) wherein $R^{22}$ is 3-hydroxymethylbenzyl and $R^{23}$ is hydrogen;

the compound of Formula (IIa) wherein $R^{22}$ is 3-hydroxymethylbenzyl and $R^{23}$ is 3-(N,N-diethylaminocarbonyl)benzyl;

the compound of Formula (IIa) wherein $R^{22}$ is 3-hydroxymethylbenzyl and $R^{23}$ is 3-(N-ethylaminocarbonyl)benzyl;

the compound of Formula (IIa) wherein $R^{22}$ is 3-(N-propylaminocarbonyl)benzyl and $R^{23}$ is 3-(N-propylaminocarbonyl)benzyl;

the compound of Formula (IIa) wherein $R^{22}$ is 3-($HO_2C$)benzyl and $R^{23}$ is 3-(N-isopropylaminocarbonyl)benzyl;

the compound of Formula (IIa) wherein $R^{22}$ is 3-($HO_2C$)benzyl and $R^{23}$ is 3-(N-propylaminocarbonyl)benzyl;

the compound of Formula (IIa) wherein $R^{22}$ is 3-($HO_2C$)benzyl and $R^{23}$ is benzyl;

the compound of Formula (IIa) wherein $R^{22}$ is 3-($HO_2C$)benzyl and $R^{23}$ is cyclopropylmethyl;

the compound of Formula (IIa) wherein $R^{22}$ is 4-hydroxymethylbenzyl and $R^{23}$ is 3-($HO_2C$)benzyl;

the compound of Formula (IIa) wherein $R^{22}$ is 3-hydroxymethylbenzyl and $R^{23}$ is 3-pyridinylmethyl;

the compound of Formula (IIa) wherein $R^{22}$ is 4-hydroxymethylbenzyl and $R^{23}$ is 3-aminocarbonylbenzyl;

the compound of Formula (IIa) wherein $R^{22}$ is 3-aminobenzyl and $R^{23}$ is 2-naphthylmethyl;

the compound of Formula (IIa) wherein $R^{22}$ is cyclopropylmethyl and $R^{23}$ is 3-aminocarbonylbenzyl;

the compound of Formula (IIa) wherein $R^{22}$ is 3-aminocarbonylbenzyl and $R^{23}$ is hydrogen;

the compound of Formula (IIa) wherein $R^{22}$ is 3-hydroxymethylbenzyl and $R^{23}$ is 3-(N-ethylaminocarbonyl)benzyl;

the compound of Formula (IIa) wherein $R^{22}$ is 3-hydroxymethylbenzyl and $R^{23}$ is 3-(N-methylamino)benzyl;

the compound of Formula (IIa) wherein $R^{22}$ is 3-(N-methylamino)benzyl and $R^{23}$ is 2-naphthylmethyl;

the compound of Formula (IIa) wherein $R^{22}$ is 4-formylbenzyl and $R^{23}$ is 4-hydroxymethylbenzyl;

the compound of Formula (IIa) wherein $R^{22}$ is 3-(1-hydroxy-1-ethyl)benzyl and $R^{23}$ is 3-(1-hydroxyethyl)benzyl;

the compound of Formula (IIa) wherein $R^{22}$ is 3-pyridinylmethyl and $R^{23}$ is 4-hydroxymethylbenzyl;

the compound of Formula (IIa) wherein $R^{22}$ is 3-(N-imidazolylmethyl)benzyl and $R^{23}$ is 3-(N-imidazolylmethyl)benzyl;

the compound of Formula (IIa) wherein $R^{22}$ is 3-(2,2-dimethyl-1-propionyl)benzyl and $R^{23}$ is 3-(2,2-dimethyl-1-propionyl)benzyl;

the compound of Formula (IIa) wherein $R^{22}$ is 3-(2,2,2-trifluoro-1-hydroxyethyl)benzyl and $R^{23}$ is 3-(2,2,2-trifluoro-1-hydroxyethyl)benzyl;

the compound of Formula (IIa) wherein $R^{22}$ is 3-(2-imidazolyl-C(=O))benzyl and $R^{23}$ is 3-(2-imidazolyl-C(=O))benzyl;

the compound of Formula (IIa) wherein $R^{22}$ is 3-(3-hydroxy-1-propyn-1-yl)benzyl and $R^{23}$ is 3-(3-hydroxy-1-propyn-1-yl)benzyl;

the compound of Formula (IIa) wherein $R^{22}$ is 3-(2,2,2-trifluoroacetyl)benzyl and $R^{23}$ is 3-(2,2,2-trifluoroacetyl)benzyl;

the compound of Formula (IIa) wherein $R^{22}$ is 3-propionylbenzyl and $R^{23}$ is 3-propionylbenzyl;

the compound of Formula (IIa) wherein $R^{22}$ is 3-(4-pyrazolyl)benzyl and $R^{23}$ is 3-(4-pyrazolyl)benzyl;

the compound of Formula (IIa) wherein $R^{22}$ is 3-($CH_3CH_2C$(=N-OH))benzyl and $R^{23}$ is 3-($CH_3CH_2C$(=N-OH))benzyl;

the compound of Formula (IIa) wherein $R^{22}$ is 3-sulfonamidobenzyl and $R^{23}$ is 3-sulfonamidobenzyl;

the compound of Formula (IIa) wherein $R^{22}$ is 3-($CF_3CH_2C$(=N-OH))benzyl and $R^{23}$ is 3-($CF_3CH_2C$(=N-OH))benzyl;

the compound of Formula (IIa) wherein $R^{22}$ is 4-fluoromethylbenzyl and $R^{23}$ is 4-fluoromethylbenzyl;

the compound of Formula (IIa) wherein $R^{22}$ is 4—(1-hydroxyethyl)benzyl and $R^{23}$ is 4—(1-hydroxyethyl)benzyl; and the compound of Formula (IIa) wherein $R^{22}$ is 3-(5-methyl-1,2,3-oxadiazolyl)benzyl and $R^{23}$ is 3-(5-methyl-1,2,3-oxadiazolyl)benzyl.

the compound of formula (IIa) wherein $R^{22}$ is 3-($H_2NC$(=NOH)benzyl and $R^{23}$ is 3-($H_2NC$(=NOH)benzyl;

the compound of formula (IIa) wherein $R^{22}$ is 3-($H_2NC$(=NOH)-4-fluorobenzyl and $R^{23}$ is 3-($H_2NC$(=NOH)-4-fluorobenzyl;

the compound of formula (IIa) wherein $R^{22}$ is 5-benzotriazolylmethyl and $R^{23}$ is 5-benzotriazolylmethyl;

the compound of formula (IIa) wherein $R^{22}$ is 5-benzimidazolylmethyl and $R^{23}$ is 5-benzimidazolylmethyl;

the compound of formula (IIa) wherein $R^{22}$ is 5-benzimidazolylmethyl and $R^{23}$ is 5-benzimidazolylmethyl;

the compound of formula (IIa) wherein $R^{22}$ is 5-benzotriazolylmethyl and $R^{23}$ is 4-hydroxymethylbenzyl;

the compound of formula (IIa) wherein $R^{22}$ is 5-benzotriazolylmethyl and $R^{23}$ is 3-(3-pyrazolyl)benzyl;

the compound of formula (IIa) wherein $R^{22}$ is 5-indazolylmethyl and $R^{23}$ is 5-indazolylmethyl;

the compound of formula (IIa) wherein $R^{22}$ is 3-chloro-5-indazolylmethyl and $R^{23}$ is 3-chloro-5-indazolylmethyl;

the compound of formula (IIa) wherein $R^{22}$ is 3-methylamino-5-indazolylmethyl and $R^{23}$ is 3-methylamino-5-indazolylmethyl;

the compound of formula (IIa) wherein $R^{22}$ is 3-ethylamino-5-indazolylmethyl and $R^{23}$ is 3-ethylamino-5-indazolylmethyl;

the compound of formula (IIa) wherein $R^{22}$ is 6-indazolylmethyl and $R^{23}$ is 6-indazolylmethyl;

the compound of formula (IIa) wherein $R^{22}$ is 3-amino-5-benzisoxazolylmethyl and $R^{23}$ is 3-amino-5-benzisoxazolylmethyl;

[8] Specifically preferred compounds useful in the present invention within the scope of Formula (I) are compounds of Formula (IIaa):

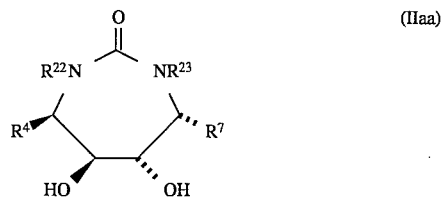

(IIaa)

or a pharmaceutically acceptable salt or prodrug form thereof wherein:

$R^4$ and $R^7$ are independently selected from: benzyl, fluorobenzyl, pyrrolylmethyl, methoxybenzyl, isobutyl, nitrobenzyl aminobenzyl, $R^{22}$ and $R^{23}$ are independently selected from:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC$(=O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, ($CH_3O_2CO$)-benzyl, ($HOCH_2CH_2N$=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl) ethylbenzyl, ($CH_3C$(=NOH))-benzyl, ($H_2NNHC$(=O))-benzyl, (H$_2$NC(=O)NHN=CH) -benzyl, (CH$_3$ONHC(=O))-benzyl, (HONHC(=O))-benzyl, (CH$_3$NHC (=O)) -benzyl, N, N-dimethylaminocarbonylbenzyl, (HOCH$_2$CH (OH) CH$_2$O)-benzyl, hydroxyethoxybenzyl (oxazolidinyl)-benzyl, (hydroxyl) hexyl, hexenyl, (hydroxy) octyl, (hydroxyl) pentyl, (carboxy) pentyl, (carbomethoxy) pentyl, (methylthio) benzyl, (methylsulfonyl) benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl) alanylaminobenzyl, phenylalanylaminobenzyl, (N-phenylmethoxycarbonyl) phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl) benzyl, (imidazolyl-C(=O))-benzyl, (pyrazolyl-C(=O)) -benzyl, (pyridylmethylaminocarbonyl) benzyl, (oxadiazolidinonyl)benzyl, trifluoroacetylbenzyl, (pyrazolyl)benzyl, (H$_2$NS$_2$O)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH)) -benzyl, (trifluorohydroxyethyl) benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C-C(=O))benzyl, (N-methyl-N-ethylaminoethyl) aminocarbonylbenzyl, (pyrrolidinylethyl) aminocarbonylbenzyl, or (piperidinylethyl) aminocarbonylbenzyl, (H$_2$NC(=NOH)) benzyl, (H$_2$NC(=NOH))fluorobenzyl, benzimidazolylmethyl, benzotriazolylmethyl, indazolylmethyl, benzoxazolinylmethyl, benzisoxazolylmethyl, thienylmethyl, furylmethyl.

[9] Specifically preferred compounds useful in the present invention within the scope of Formula (I) are compounds of Formula (IIaa):

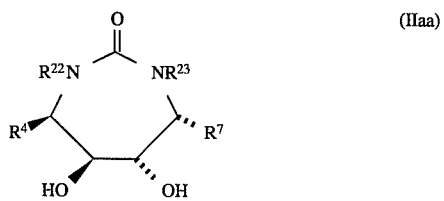

(IIaa)

selected from the group consisting of:

the compound of Formula (IIaa) wherein $R^4$ and $R^7$ are isobutyl, $R^{22}$ and $R^{23}$ are cyclopropylmethyl;

the compound of Formula (IIaa) wherein $R^4$ and $R^7$ are isobutyl, $R^{22}$ and $R^{23}$ are allyl;

the compound of Formula (IIaa) wherein $R^4$ is 4-nitrobenzyl, $R^7$ is 2-nitrobenzyl, $R^{22}$ and $R^{23}$ are cyclopropylmethyl;

the compound of Formula (IIaa) wherein $R^4$ and $R^7$ are 4-nitrobenzyl, $R^{22}$ and $R^{23}$ are cyclopropylmethyl;

the compound of Formula (IIaa) wherein $R^4$ is 4-nitrobenzyl, $R^7$ is 2-nitrobenzyl, $R^{22}$ and $R^{23}$ are n-butyl;

the compound of Formula (IIaa) wherein $R^4$ is 4-aminobenzyl, $R^7$ is 2-aminobenzyl, $R^{22}$ and $R^{23}$ are cyclopropylmethyl;

the compound of Formula (IIaa) wherein $R^4$ and $R^7$ are 4-fluorobenzyl, $R^{22}$ and $R^{23}$ are 3-hydroxybenzyl;

the compound of Formula (IIaa) wherein $R^4$ and $R^7$ are 4-fluorobenzyl, $R^{22}$ and $R^{23}$ are cyclopropylmethyl;

the compound of Formula (IIaa) wherein $R^4$ and $R^7$ are 4-fluorobenzyl, $R^{22}$ and $R^{23}$ are 4-hydroxymethylbenzyl;

the compound of Formula (IIaa) wherein $R^4$ and $R^7$ are 4-fluorobenzyl, $R^{22}$ and $R^{23}$ are 3-aminocarbonylbenzyl;

the compound of Formula (IIaa) wherein $R^4$ and $R^7$ are 4-fluorobenzyl, $R^{22}$ and $R^{23}$ are 3-acetylbenzyl;

the compound of Formula (IIaa) wherein $R^4$ and $R^7$ are 4-fluorobenzyl, $R^{22}$ and $R^{23}$ are 3-butyrylbenzyl;

the compound of Formula (IIaa) wherein $R^4$ and $R^7$ are 4-fluorobenzyl, $R^{22}$ and $R^{23}$ are 3-hydroxymethylbenzyl;

the compound of Formula (IIaa) wherein $R^4$ and $R^7$ are 4-fluorobenzyl, $R^{22}$ and $R^{23}$ are 3-(CH$_3$C(=N-OH) benzyl; and the compound of Formula (IIaa) wherein $R^4$ and $R^7$ are 3-methoxybenzyl, $R^{22}$ and $R^{23}$ are benzyl;

the compound of formula (IIaa) wherein $R^4$ and $R^7$ are 4-fluorobenzyl, $R^{22}$ and $R^{23}$ are 3-(H$_2$NC(=NOH)benzyl;

the compound of formula (IIaa) wherein $R^4$ and $R^7$ are 4-fluorobenzyl, $R^{22}$ and $R^{23}$ are 3-(H$_2$NC(=NOH)-4 -fluorobenzyl;

the compound of formula (IIaa) wherein $R^4$ and $R^7$ are 3-methoxybenzyl, $R^{22}$ and $R^{23}$ are cyclopropylmethyl;

the compound of formula (IIaa) wherein $R^4$ and $R^7$ are 3-methoxybenzyl, $R^{22}$ and $R^{23}$ are 4 -hydroxymethylbenzyl;

the compound of formula (IIaa) wherein $R^4$ and $R^7$ are 3-methoxybenzyl, $R^{22}$ and $R^{23}$ are 3-methoxybenzyl;

the compound of formula (IIaa) wherein $R^4$ and $R^7$ are 3-hydroxybenzyl, $R^{22}$ and $R^{23}$ are 3-hydroxybenzyl.

the compound of formula (IIaa) wherein $R^4$ and $R^7$ are 4-methoxybenzyl, $R^{22}$ and $R^{23}$ are cyclopropylmethyl;

the compound of formula (IIaa) wherein $R^4$ and $R^7$ are 4-methoxybenzyl, $R^{22}$ and $R^{23}$ are benzyl;

the compound of formula (IIaa) wherein $R^4$ and $R^7$ are 4-methoxybenzyl, $R^{22}$ and $R^{23}$ are 2-naphthylmethyl;

the compound of formula (IIaa) wherein $R^4$ and $R^7$ are 4-methoxybenzyl, $R^{22}$ and $R^{23}$ are 4 -hydroxymethylbenzyl;

the compound of formula (IIaa) wherein $R^4$ and $R^7$ are 4-hydroxybenzyl, $R^{22}$ and $R^{23}$ are benzyl;

the compound of formula (IIaa) wherein $R^4$ and $R^7$ are 4-methoxybenzyl, $R^{22}$ and $R^{23}$ are allyl;

the compound of formula (IIaa) wherein $R^4$ and $R^7$ are 4-(2-hydroxyethoxy)benzyl, $R^{22}$ and $R^{23}$ are benzyl;

the compound of formula (IIaa) wherein $R^4$ and $R^7$ are 4-(2-morpholinylethoxy)benzyl, $R^{22}$ and $R^{23}$ are benzyl;

the compound of formula (IIaa) wherein $R^4$ and $R^7$ are 3-(H$_2$NC(=O) CH$_2$O)benzyl, $R^{22}$ and $R^{23}$ are n-butyl;

the compound of formula (IIaa) wherein $R^4$ and $R^7$ are 3,4-difluorobenzyl, $R^{22}$ and $R^{23}$ are 3 -hydroxymethylbenzyl;

the compound of formula (IIaa) wherein $R^4$ and $R^7$ are 3,4-difluorobenzyl, $R^{22}$ and $R^{23}$ are 4 -hydroxymethylbenzyl;

the compound of formula (IIaa) wherein $R^4$ and $R^7$ are 3,4-difluorobenzyl, $R^{22}$ and $R^{23}$ are 3 -(H$_2$NC (=O))benzyl;

the compound of formula (IIaa) wherein $R^4$ and $R^7$ are 3,4-difluorobenzyl, $R^{22}$ and $R^{23}$ are 3 -(H$_2$NC(=NOH))benzyl;

the compound of formula (IIaa) wherein $R^4$ and $R^7$ are 2-naphthylmethyl, $R^{22}$ and $R^{23}$ are benzyl;

the compound of formula (IIaa) wherein $R^4$ and $R^7$ are 2-naphthylmethyl, $R^{22}$ and $R^{23}$ are cyclopropylmethyl;

the compound of formula (IIaa) wherein $R^4$ and $R^7$ are 2-thienylmethyl, $R^{22}$ and $R^{23}$ are cyclopropylmethyl;

the compound of formula (IIaa) wherein $R^4$ and $R^7$ are 2-thienylmethyl, $R^{22}$ and $R^{23}$ are 3 -(H$_2$NC (=NOH)) benzyl;

the compound of formula (IIaa) wherein $R^4$ and $R^7$ are 4-methylthiobenzyl, $R^{22}$ and $R^{23}$ are benzyl;

the compound of formula (IIaa) wherein $R^4$ and $R^7$ are isopropyl, $R^{22}$ and $R^{23}$ are n-hexyl;

[10] Also specifically preferred compounds useful in the present invention within the scope of Formula (I) are compounds of Formula (IIb):

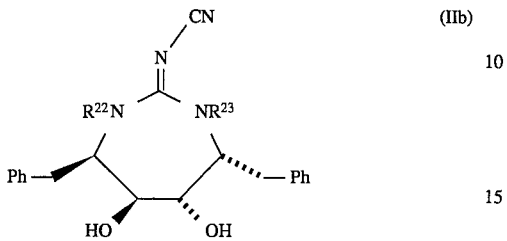
(IIb)

or a pharmaceutically acceptable salt or prodrug form thereof wherein:

$R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, $(CH_3O_2CO)$-benzyl, $(HOCH_2CH_2N=CH)$-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl) ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N,N-dimethylaminocarbonylbenzyl, $(HOCH_2CH(OH)CH_2O)$-benzyl, hydroxyethoxybenzyl(oxazolidinyl)-benzyl, (hydroxyl) hexyl, hexenyl, (hydroxy) octyl, (hydroxyl) pentyl, (carboxy) pentyl, (carbomethoxy) pentyl, (methylthio) benzyl, (methylsulfonyl) benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl) alanylaminobenzyl, phenylalanylaminobenzyl, (N-phenylmethoxycarbonyl) phenylalanylaminobenzyl, $(CH_3CH_2NHC(=O))$-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl) benzyl, (imidazolyl-C(=O))-benzyl, (pyrazolyl-C(=O)) -benzyl, (pyridylmethylaminocarbonyl)benzyl, (oxadiazolidinonyl)benzyl, trifluoroacetylbenzyl, (pyrazolyl)benzyl, $(H_2NSO_2)$-benzyl, dihydroxyethylbenzyl, (MeHNC(=O)NH)-benzyl, $(H_2NC(=O)NH)$-benzyl, $(HC(=O)NH)$-benzyl, methanesulfonylpentyl, methoxypentyl, N-formyl-N-methylaminobenzyl, acetylaminobenzyl, propionylbenzyl, butyrylbenzyl, $(CH_3CH_2C(=NOH))$-benzyl, (trifluorohydroxyethyl) benzyl, $(CF_3C(=NOH))$-benzyl, (N-methylglycyl)aminobenzyl, ((4-morpholino)-ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, $(CH_3NHC(=O)O)$benzyl, $(NH_2C(=O)$ $CH_2O)$benzyl, $(NH_2C(=NH))$benzyl, ((N-phenylmethoxycarbonyl) glycylamino) benzyl, (imidazolylmethyl)benzyl, $((CH_3)_3C-C(=O))$benzyl, (N-methyl-N-ethylaminoethyl) aminocarbonylbenzyl, (pyrrolidinylethyl) aminocarbonylbenzyl, and (piperidinylethyl) aminocarbonylbenzyl, $(H_2NC(=NOH))$benzyl, $(H_2NC(=NOH))$fluorobenzyl, benzimidazolylmethyl, benzotriazolylmethyl, indazolylmethyl, benzoxazolinylmethyl, benzisoxazolylmethyl, thienylmethyl, furylmethyl.

[11] Specifically preferred compounds of the invention within the scope of Formula (I) are compounds of Formula (IIb):

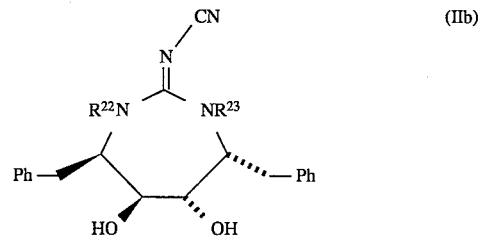
(IIb)

or a salt thereof, selected from the group consisting of:

the compound of Formula (IIb) wherein $R^{22}$ is 4-hydroxybenzyl and $R^{23}$ is 4-hydroxybenzyl;

the compound of Formula (IIb) wherein $R^{22}$ is cyclopentylmethyl and $R^{23}$ is cyclopentylmethyl;

the compound of Formula (IIb) wherein $R^{22}$ is n-butyl and $R^{23}$ is n-butyl;

the compound of Formula (IIb) wherein $R^{22}$ is 3-hydroxybenzyl and $R^{23}$ is 3-hydroxybenzyl;

the compound of Formula (IIb) wherein $R^{22}$ is 3-aminobenzyl and $R^{23}$ is 3-aminobenzyl;

the compound of Formula (IIb) wherein $R^{22}$ is cyclohexylmethyl and $R^{23}$ is cyclohexylmethyl;

the compound of Formula (IIb) wherein $R^{22}$ is cyclobutylmethyl and $R^{23}$ is cyclobutylmethyl;

the compound of Formula (IIb) wherein $R^{22}$ is 3-hydroxymethylbenzyl and $R^{23}$ is 3-hydroxymethylbenzyl;

the compound of Formula (IIb) wherein $R^{22}$ is 3-formylbenzyl and $R^{23}$ is 3-formylbenzyl; and the compound of Formula (IIb) wherein $R^{22}$ is -formaldoximebenzyl and $R^{23}$ is 3-formaldoximebenzyl.

[12] Specifically preferred compounds useful in the present invention within the scope of Formula (I) are compounds of Formula (Ibb):

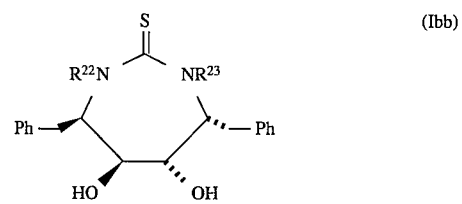
(Ibb)

or a pharmaceutically acceptable salt or prodrug form thereof wherein:

$R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime) benzyl, (O-methyl-formaldoxime) benzyl, $(CH_3O_2CO)$-benzyl, $(HOCH_2CH_2N=CH)$-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl) ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N,N-dimethyl-aminocarbonylbenzyl, $(HOCH_2CH(OH)CH_2O)$-benzyl, hydroxyethoxybenzyl (oxazolidinyl)-benzyl, (hydroxyl) hexyl, hexenyl, (hydroxy) octyl, (hydroxyl) pentyl, (carboxy) pentyl, (carbomethoxy) pentyl, (methylthio) benzyl, (methylsulfonyl) benzyl, N,N-dimethyl-aminomethylbenzyl, N-methylaminomethylbenzyl, glycylaminobenzyl, N,N-dimethylglycylaminobenzyl, alanylaminobenzyl, (N-phenylmethoxy-carbonyl)alanylaminobenzyl, phenylalanylaminobenzyl, (N-phenylmethoxycarbonyl) phenylalanylaminobenzyl, $(CH_3CH_2NHC(=O))$-benzyl, N,N-diethylaminocarbonylbenzyl, N-ethylaminocarbonylbenzyl, N-propylaminocarbonylbenzyl, N,N-diisopropyl-aminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl) benzyl, (oxadiazolidinonyl) benzyl, trifluoroacetylbenzyl, (pyrazolyl) benzyl, $(H_2NSO_2)$-benzyl, dihydroxyethylbenzyl, (MeHNC(=O)NH)-benzyl, $(H_2NC(=O)NH)$-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, $(CH_3CH_2C(=NOH))$-benzyl, (trifluorohydroxyethyl) benzyl, $(CF_3C(=NOH))$-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, $(CH_3NHC(=O)O)$benzyl, $(NH_2C(=O)CH_2O)$benzyl, $(NH_2C(=NH))$benzyl, (N-phenylmethoxycarbonyl)glycylamino)benzyl, (imidazolylmethyl)benzyl, $((CH_3)_3C-C(=O))$benzyl, (N-methyl-N-ethylaminoethyl)aminocarbonylbenzyl, (pyrrolidinylethyl) aminocarbonylbenzyl, and (piperidinylethyl) aminocarbonylbenzyl, $(H_2NC(=NOH))$benzyl, $(H_2NC(=NOH))$fluorobenzyl, benzimidazolylmethyl, benzotriazolylmethyl, indazolylmethyl, benzoxazolinylmethyl, benzisoxazolylmethyl, thienylmethyl, furylmethyl.

[13] Specifically preferred compounds of the invention within the scope of Formula (I) are compounds of Formula (Ibb):

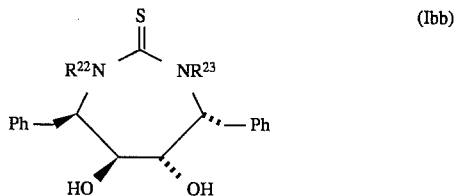

or a salt thereof, selected from the group consisting of:

the compound of Formula (Ibb) wherein $R^{22}$ is benzyl and $R^{23}$ is hydrogen;

the compound of Formula (Ibb) wherein $R^{22}$ is cyclopropylmethyl and $R^{23}$ is cyclopropylmethyl;

the compound of Formula (Ibb) wherein $R^{22}$ is benzyl and $R^{23}$ is benzyl; and the compound of Formula (Ibb) wherein $R^{22}$ is 3-hydroxybenzyl and $R^{23}$ is 3-hydroxybenzyl.

the compound of formula (Ibb) wherein $R^{22}$ is 3-hydroxymethylbenzyl and $R^{23}$ is 3-hydroxymethylbenzyl;

the compound of formula (Ibb) wherein $R^{22}$ is 4-hydroxybenzyl and $R^{23}$ is 4-hydroxybenzyl;

the compound of formula (Ibb) wherein $R^{22}$ is 3-methoxybenzyl and $R^{23}$ is 3-methoxybenzyl;

the compound of formula (Ibb) wherein $R^{22}$ is 3-$(H_2NC(=NOH))$benzyl and $R^{23}$ is 4-hydroxymethylbenzyl;

the compound of formula (Ibb) wherein $R^{22}$ is 3-$(H_2NC(=NOH))$benzyl and $R^{23}$ is 3-$(H_2NC(=NOH))$benzyl;

the compound of formula (Ibb) wherein $R^{22}$ is 3-$(H_2NC(=NOH))$-4-fluorobenzyl and $R^{23}$ is 3-$(H_2NC(=NOH))$-4-fluorobenzyl.

[14] Specifically preferred compounds of the invention within the scope of Formula (I) are compounds of Formula (Ic):

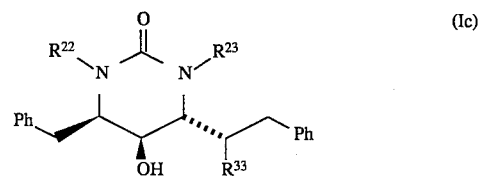

or a pharmaceutically acceptable salt or prodrug form thereof wherein:

$R^{33}$ is OH, halogen, H, $N_3$ or can alternatively be taken together with $R^{23}$ to form a direct bond; and wherein $R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=$ O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethyl-aminocarbonylbenzyl, ($HOCH_2CH(OH)CH_2O$)-benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethyl-aminomethylbenzyl, N-methylaminomethylbenzyl, glycylaminobenzyl, N,N-dimethylglycylaminobenzyl, alanylaminobenzyl, (N-phenylmethoxy-carbonyl) alanylaminobenzyl, phenylalanylaminobenzyl, (N-phenylmethoxycarbonyl) phenylalanylaminobenzyl, ($CH_3CH_2NHC(=O)$) -benzyl, N,N-diethylaminocarbonylbenzyl, N-ethylaminocarbonylbenzyl, N-propylaminocarbonylbenzyl, N,N-diisopropyl-aminocarbonylbenzyl, N,N-di-n-propylaminocarbonylbenzyl, (hydroxypropynyl)benzyl, (imidazolyl-C(=O))-benzyl, (pyrazolyl-C(=O)) -benzyl, (pyridylmethylaminocarbonyl)benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)-benzyl, (trifluorohydroxyethyl) benzyl, ($CF_3C(=NOH)$)-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl (benzyl—NHC(=O)O) benzyl, ($CH_3NHC(=O)O$)benzyl, ($NH_2C(=O)CH_2O$)benzyl, ($NH_2C(=NH)$)benzyl, ((N-phenylmethoxycarbonyl)glycylamino)benzyl, (imidazolylmethyl)benzyl, (($CH_3)_3C-C(=O)$)benzyl, (N-methyl-N-ethylaminoethyl) aminocarbonylbenzyl, (pyrrolidinylethyl) aminocarbonylbenzyl, and (piperidinylethyl) aminocarbonylbenzyl, ($H_2NC(=NOH)$)benzyl, ($H_2NC(=NOH)$)fluorobenzyl, benzimidazolylmethyl, benzotriazolylmethyl, indazolylmethyl, benzoxazolinylmethyl, benzisoxazolylmethyl, thienylmethyl, furylmethyl.

[15] Specifically preferred compounds of the invention within the scope of Formula (I) are compounds of Formula (Ic):

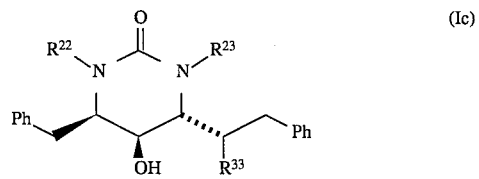

(Ic)

selected from the group consisting of:

the compound of Formula (Ic) wherein $R^{22}$ is 3-hydroxybenzyl, $R^{23}$ is 3-hydroxybenzyl and $R^{33}$ is hydrogen;

the compound of Formula (Ic) wherein $R^{22}$ is 3-acetylbenzyl, $R^{23}$ is 3-acetylbenzyl and $R^{33}$ is hydrogen; and the compound of Formula (Ic)˙ wherein $R^{22}$ is 3-hydroxymethylbenzyl, $R^{23}$ is 3-hydroxymethylbenzyl and $R^{33}$ is hydrogen;

the compound of formula (Ic) wherein $R^{22}$ is 3 -($H_2NC(=O)$)benzyl, $R^{23}$ is 3-($H_2NC(=O)$)benzyl and $R^{33}$ is hydrogen.

the compound of formula (Ic) wherein $R^{22}$ is 3 -($H_2NC(=NOH)$) benzyl, $R^{23}$ is 3-($H_2NC(=NOH)$)benzyl and $R^{33}$ is hydrogen.

the compound of formula (Ic) wherein $R^{22}$ is 3 -($H_2NC(=O)$)-4-fluorobenzyl, $R^{23}$ is 3-($H_2NC(=O)$)-4 -fluorobenzyl and $R^{33}$ is hydrogen.

the compound of formula (Ic) wherein $R^{22}$ is 3 -($H_2NC(=NOH)$)-4-fluorobenzyl, $R^{23}$ is 3-($H_2NC(=NOH)$)-4 -fluorobenzyl and $R^{33}$ is hydrogen.

[16] Specifically preferred compounds of the invention within the scope of Formula (I) are compounds of Formula:

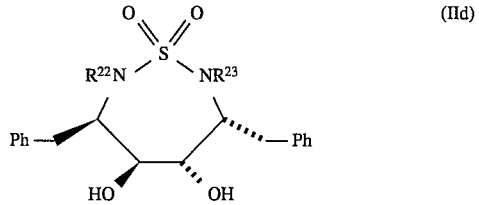

(IId)

or a pharmaceutically acceptable salt or prodrug form thereof wherein:

$R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, (CH30NHC(=O))-benzyl, ($HONHC(=O)$)-benzyl, ($CH_3NHC(=O)$)-benzyl, N,N-dimethyl-aminocarbonylbenzyl, ($HOCH_2CH(OH)CH_2O$)-benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethyl-aminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropyl-aminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2$C(=NOH))-benzyl, (trifluorohydroxyethyl)benzyl, ($CF_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3$NHC(=O)O)benzyl, ($NH_2$C(=O)$CH_2$O)benzyl, ($NH_2$C(=NH))benzyl, ((N-phenylmethoxycarbonyl)glycylamino)benzyl, (imidazolylmethyl)benzyl, (($CH_3$)$_3$C-C(=O))benzyl, (N-methyl-N-ethylaminoethyl)aminocarbonylbenzyl, (pyrrolidinylethyl)aminocarbonylbenzyl, and (piperidinylethyl)aminocarbonylbenzyl, ($H_2$NC(=NOH))benzyl, ($H_2$NC(=NOH))fluorobenzyl, benzimidazolylmethyl, benzotriazolylmethyl, indazolylmethyl, benzoxazolinylmethyl, benzisoxazolylmethyl, thienylmethyl, furylmethyl.

[17] Specifically preferred compounds of the invention within the scope of Formula (I) are compounds of Formula (IId):

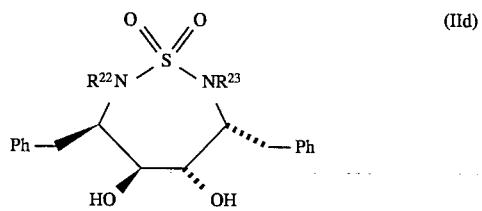

or a salt thereof,
selected from the group consisting of:

the compound of Formula (IId) wherein $R^{22}$ is 4-hydroxymethylbenzyl and $R^{23}$ is 4-hydroxymethylbenzyl;

the compound of Formula (IId) wherein $R^{22}$ is 3-hydroxybenzyl and $R^{23}$ is 3-hydroxybenzyl;

the compound of Formula (IId) wherein $R^{22}$ is cyclopropylmethyl and $R^{23}$ is cyclopropylmethyl;

the compound of Formula (IId) wherein $R^{22}$ is 2-naphthylmethyl and $R^{23}$ is 2-naphthylmethyl;

the compound of Formula (IId) wherein $R^{22}$ is 4-hydroxybenzyl and $R^{23}$ is 4-hydroxybenzyl;

the compound of Formula (IId) wherein $R^{22}$ is 3-aminobenzyl and $R^{23}$ is 3-aminobenzyl;

the compound of Formula (IId) wherein $R^{22}$ is 3-hydroxymethylbenzyl and $R^{23}$ is 3-hydroxymethylbenzyl;

the compound of Formula (IId) wherein $R^{22}$ is 3-(Me2NCH$_2$C(=O)NH)-benzyl and $R^{23}$ is 3-(Me$_2$NCH$_2$C(=O)NH)-benzyl;

the compound of Formula (IId) wherein $R^{22}$ is 3-formaldoximebenzyl and $R^{23}$ is 3-formaldoximebenzyl;

the compound of Formula (IId) wherein $R^{22}$ is 3-(CH$_3$C(=N-OH))-benzyl and $R^{23}$ is 3-(CH$_3$C(=N-OH))-benzyl.

the compound of formula (IId) wherein $R^{22}$ is 3-(2-amino-4-thienyl)benzyl and $R^{23}$ is 3-(2-amino-4-thienyl)-benzyl;

the compound of formula (IId) wherein $R^{22}$ is 5-hydroxypentyl and $R^{23}$ is 5-hydroxypentyl;

the compound of formula (IId) wherein $R^{22}$ is 6-hydroxypentyl and $R^{23}$ is 6-hydroxypentyl;

the compound of formula (IId) wherein $R^{22}$ is 5-hydroxypentyl and $R^{23}$ is 2-naphthylmethyl;

the compound of formula (IId) wherein $R^{22}$ is 5-hydroxypentyl and $R^{23}$ is 4-hydroxymethylbenzyl; and the compound of formula (IId) wherein $R^{22}$ is 5-hydroxypentyl and $R^{23}$ is 3-hydroxymethylbenzyl;

As used herein with regard to the subject cyclic urea compounds of Formula (I) described above, "pharmaceutically acceptable salts and prodrugs" refer to derivatives of the disclosed compounds that, respectively, are modified by making acid or base salts, or are modified by modifying functional groups present in the compounds in such a way that the modifications are cleaved, either in routine manipulation or in vivo, to the parent compounds. Examples include, but are not limited to: mineral or organic acid salts of basic residues such as amines; alkali or organic salts of acidic residues such as carboxylic acids; esters of carboxylates; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* Mack Publishing Company, Easton, Pa., a standard reference text in this field.

The cyclic HIV protease inhibitors of Formula (I) useful in the compositions of the present invention may be prepared by the methods set forth in PCT International Patent Application Publication No. WO 93/07128 and in copending, commonly assigned U.S. patent application U.S. Ser. No. 08/047,330, filed Apr. 15, 1993.

As noted above, the compositions of the present invention contain, in addition to a cyclic urea type compound such as a compound of Formula (I) described above, a liquid or solid vehicle comprised of fatty acid esters of glycerol, fatty acid esters of polyethylene glycol, or mixtures thereof.

The vehicle, that is, the mixture of components in which the compounds of Formula (I) are dissolved or dispersed, should be relatively hydrophilic, having a hydrophil-lipophil balance (HLB) value of at least about 10. The vehicle may include other excipients, in addition to the fatty acid esters of glycerol and fatty acid esters of polyethylene glycol. For example, polyethylene glycol 400 was usually included in the vehicle at about 15% concentration. The desired HLB value is for the fatty acid esters of glycerol and fatty acid esters of polyethylene glycol component of the vehicle. The hydrophil-lipophil balance (also referred to as the HLB value) is a numerical index which is used to characterize amphiphilic substances, with lower values denoting more lipophilic (hydrophobic) substances and higher values denoting more hydrophilic (lipophobic) substances. As those skilled in the art will recognize, the number of carbon atoms in any fatty acid substituents, the length of any polyethylene glycol substituents, the relative proportions of ingredients, the degree of substitution, etc., of each vehicle component will all combine to influence the HLB value.

The HLB values of various compounds are well known to those skilled in the formulations art, and appear in numerous published charts and tables. HLB values may also be calculated in accordance with the following formula:

HLB=Σ(hydrophilic group numbers)–m(group number per —CH$_2$— group)+7

In the above formula, the hydrophilic and —CH$_2$— group numbers may be empirically determined, as those skilled in the art will recognize, or, alternatively, reference may be made to various published charts and tables which list various hydrophilic group numbers (such as for ester, hydroxyl, etc., groups), and various group numbers per —CH$_2$— group.

HLB values and group number values may be found, in numerous publications, such as, for example, in Dreher et al., U.S. Pat. No. 3,643,738, Becher, Paul, *Principles of Emulsion Technology*, Reinhold Publishing Group, New York, N.Y. (1955), Davies, J. T. and Rideal, E. K., *Interfacial Phenomena*, 2d ed., Academic Press, New York, N.Y. (1963), the disclosures of each of which are hereby incorporated herein by reference in their entirety. In Becher, Paul, *Principles of Emulsion Technology*, Reinhold Publishing Group, New York, N.Y. (1955), see, in particular, pp. 104–109. In Davies, J. T. and Rideal, E. K., *Interfacial Phenomena*, 2d ed., Academic Press, New York, N.Y. (1963), see, in particular, pp. 371–383. Since HLB values are algebraically additive, where a blend of vehicle components are used, the HLB numbers of the individual components may be simply added together in accordance with their proportion in the ultimate vehicle blend to easily determine the HLB value of the vehicle blend as those skilled in the art will recognize.

As noted above, the HLB value of the vehicle of the present invention should be at least about 10, preferably at least about 11, more preferably at least about 12, even more preferably at least about 13, still even more preferably at least about 14. HLB values may generally extend to about 50, limited in accordance with the present invention, as those skilled in the art will recognize, by practicality. Preferably, however, the HLB value is equal to or less than about 30, more preferably equal to or less than about 25 and most preferably equal to or less than about 20. In the most preferable embodiments of the present invention, the HLB value of the vehicle is between about 10 and about 20, preferably between about 12 and about 18, more preferably between about 13 and about 17, and most preferably at about 14. In short, the vehicles of the invention are preferably relatively hydrophilic and water-dispersible.

As noted above, the vehicles of the present invention may be comprised of one or more fatty acid esters of glycerol, or one or more fatty acid esters of polyethylene glycol, or mixtures thereof. Any of the various types of fatty acid esters of glycerol or polyethylene glycol may be employed alone or in combination, to form the vehicle, provided that the vehicle has an HLB value that is at least about 10. Various fatty acid esters of glycerol and polyethylene glycol are well known, and suitable fatty acid esters will be readily apparent to those skilled in the art, once armed with the present disclosure.

Exemplary suitable glycerol fatty acid esters which either alone, or alternatively in combination with other vehicle components, may provide a vehicle with an HLB value of at least about 10, include mono-, di-, and triesters of glycerol or glycerol derivatives, wherein the fatty acid substituent is caprylate, caprate, laurate, myristate, palmitate, stearate, oleate, linoleate, linolenate, ricinoleate, arachidate, behenate, or hydroxylated products of these fatty acids. Of the foregoing listed glycerol fatty acid esters, the following are preferred: glycerol monoesters wherein the fatty acid substituent is caprate, laurate, oleate, or hydroxylated products of these fatty acids.

Exemplary suitable polyethylene glycol fatty acid esters which either alone, or alternatively in combination with other vehicle components, may provide a vehicle with an HLB value of at least about 10, include PEG stearate (such as PEG-40 stearate and PEG-8 stearate), PEG hydrogenated castor oil (such as PEG-60 hydrogenated castor oil), PEG laurate (such as PEG-8 laurate and PEG-4 laurate), PEG apricot kernel oil esters (also referred to as PEG ethoxylated persic oil esters)(such as PEG-6 apricot kernel oil esters), PEG caprylate (such as PEG-8 caprylate), PEG caprate (such as PEG-8 caprate), PEG myristate, PEG palmitate, and PEG oleate. As used herein, PEG-n refers to compounds of the structure X(OCH$_2$CH$_2$)$_n$OH, where X is hydrogen or another named substituent, and n is the average number of oxyethylene units. Compounds for which X is not H have also been referred to as PEG esters. Of the foregoing listed polyethylene glycol fatty acid esters, the following are preferred: PEG-32 laurate, PEG-60 hydrogenated castor oil, PEG-40 stearate, PEG-40 hydrogenated castor oil, and PEG-32 dilaurate.

A number of vehicle formulations which are sold commercially may be advantageously used as vehicles in the compositions of the present invention. Examples of such formulations are those sold under the trademarks Gelucire™ 44/14, Gelucire™ 35/10, Labrasol™, Labrafil™ M 1944 CS, and Cremophor™ RH 60 and Cremophor™ RH 40.

Labrafil™ M 1944 CS, one useful vehicle formulation, comprises PEG-6 apricot kernel oil esters (also referred to as PEG-6 ethoxylated persic oil esters), is sold by Gattefosse Corporation, located in Elmsford and Hawthorne, N.Y. and Westwood, N.J. It is known to contain both glycerides and polyethylene glycol esters.

Labrasol™, another useful vehicle ingredient, is a commercial brand of glycerides and polyethylene glycol esters. More specifically, it is a mixture of glycerol and PEG esters of caprylic and capric acids. Labrasol™ is also sold by Gattefosse Corporation.

Gelucire™ 44/14 and Gelucire™ 35/10 are commercial formulations of glyceride and PEG esters, also sold by Gattefosse Corporation, and are quite useful as vehicles in the compositions of the present invention. Products sold under the mark Gelucire™ are mixtures of products resulting from the transesterification between a triglyceride such as, but not limited to food grade vegetable oil, and a polyethyleneglycol (PEG) with an average molecular weight of 300 to 1500 amu. Transesterification is carried out by heating the triglyceride and PEG in the presence of a catalyst. The fatty acid content found in the product mixture can vary from 5–50% of acids chosen from the list consisting of caprylic acid (C8), capric acid (C10) lauric acid (C12) myritic acid (C14), palmitic acid (C16) and stearic acid (C18). The typical distribution of products resulting from the alcoholysis of food grade vegatable oil with PEG 1500 (amu) is shown below:

| | |
|---|---|
| monoglycerides | 4% |
| diglycerides | 8% |
| triglycerides | 7% |
| mono esters of PEG 1500 (amu) | 30% |
| diesters of PEG 1500 (amu) | 43% |
| Free PEG 1500 (amu) | 8% |

Such products may be prepared using, for example, the procedures described in Mahler et al., U.S. Pat. No. 3,288,824, the disclosures of which are hereby incorporated herein by reference, in their entirety.

Gelucire™ 44/14 and Gelucire™ 35/10 are particular Gelucire™ brands which have, respectively, a melting point of 44° C. and HLB value of 14 (hence, the terminology 44/14), and a melting point of 35° C. and HLB value of 10 (hence the terminology 35/10). Other Gelucire™ products having a variety of melting points and HLB values are also available. By way of example, the chemical analysis of Gelucire™ 44/14 from a Gattefosse Analysis Sheet published on Jan. 21, 1993, is set forth in Table A below.

TABLE A

PRODUCT NAME: GELUCIRE ™ 44/14
CHEMICAL DEFINITION:

Saturated polyglycolysed glycerides; specific mixture of mono, di and triglycerides, and polyethylene glycol mono and diesters.

PHYSICAL CHARACTERISTICS:

| | |
|---|---|
| APPEARANCE: | Waxy solid |
| ODOUR: | Faint |
| COLOUR (Gardner Scale): | 3.5 |
| DROP POINT (METTLER) (°C.): | 45.6 |

CHEMICAL CHARACTERISTICS:

| | |
|---|---|
| ACID VALUE (mgKOH/g): | 1.60 |
| SAPONIFICATION VALUE (mgKOH/g): | 85 |
| IODINE VALUE (gI2/100 g): | 0.2 |
| HYDROXYL VALUE (mgKOH/g): | 43 |
| PEROXIDE VALUE (meq 02/kg): | <0.5 |
| ALKALINE IMPURITIES (ppm NaOH): | 12 |
| WATER CONTENT (%): | <0.50 |
| FREE GLYCEROL CONTENT (%): | 0.3 |
| SULPHATED ASHES CONTENT (%): | <0.10 |

FATTY ACIDS COMPOSITION (%):

| | |
|---|---|
| Caprylic acid (C8) | 6.9 |
| Capric acid (C10) | 5.5 |
| Lauric acid (C12) | 47.6 |
| Myristic acid (C14) | 18.1 |
| Palmitic acid (C16) | 9.7 |
| Stearic acid (C18) | 11.8 |
| HEAVY METALS (ppm Pb) | <10.0 |

Cremophor RH 60 is another useful vehicle component. Cremophor RH 60 is a composition of fatty acid esters of glycerol polyethyleneglycol and fatty acid esters of polyethyleneglycol. It is sold commercially by BASF Aktiengesellschaft, Ludwigshafen, Germany. It may be prepared by reacting 60 moles of ethylene oxide with 1 mole of hydrogenated castor oil. It is commonly referred to as PEG-60 hydrogenated castor oil. The following Table B provides a chemical analysis of four Cremphor™ RH products, including RH 60, published by BASF (Cremophor™ RH Grades, Technical Leaflet, 1988).

TABLE B

| | |
|---|---|
| Products | Cremophor ™ RH |
| Nature | The Cremophor RH grades are non-ionic solubilizing and emulsifying agents produced by allowing hydrogenated castor oil with ethylene oxide. Cremophor RH 40 is produced by reacting 40–45 moles of ethylene oxide, and Cremophor RH 60 moles of ethylene oxide, with 1 mole of glyceride. The castor oil used as starting materials is of DAB 9 quality. |
| Composition | The main components of the Cremophor RH grades are fatty acid esters of glycerol polyethylene glycol and fatty acid esters of polyethylene glycol. They represent the hydrophobic part of the products. The hydrophilic part consists of polyethylene glycols and ethoxylated glycerol. |
| CTFA name | PEG-40 Hydrogenated Castor Oil<br>PEG-60 Hydrogenated Caster Oil |
| Trivial name | Glycerol-polyethylene glycol oxystearate |

| Properties | Cremophor RH 40 | Cremophor RH 410 | Cremophor RH 455 | Cremophor RH 60 |
|---|---|---|---|---|
| Physical form | viscous liquid or soft paste | viscous liquid | viscous liquid | viscous liquid or soft paste |
| Composition | 100% RH 40 | 90% RH 40; 10% water | 90% RH 40; 5% 1,2-propylene glycol; 5% water | 100% RH 60 |

Cremophor RH 410 and Cremophor RH 455 are viscous, slightly turbid liquids at room temperature. They can, therefore, be pumped at this temperature without difficulty.
An outstanding feature of all Cremophor RH grades is that their aqueous solutions have very little odour or taste.
The HLB values of Cremophor RH 40 and Cremophor RH 60 are 14 to 16 and 15 to 17, respectively.

| Data: | Cremophor RH 40 | Cremophor RH 410 | Cremophor RH 455 | Cremophor RH 60 |
|---|---|---|---|---|
| Spanoficiation value | 50–60 | 45–55 | 45–55 | 40–50 |
| Hydroxyl value | 60–75 | — | — | 50–70 |
| Acid value | $\leq 1$ | $\leq 1$ | $\leq 1$ | $\leq 1$ |
| Iodine value | $\leq 1$ | $\leq 1$ | $\leq 1$ | $\leq 1$ |
| Water content, Fischer's method | $\leq 2\%$ | 9.5–10.5% | 4.5–5.5% | $\leq 2\%$ |
| pH value of aqueous solution | 6–7 | 6–7 | 6–7 | 6–7 |
| Colour strength | max. G 5 | max. G 5 | max. G 5 | max. G 5 |
| Viscosity, Höppler, 25° C., Mpa.s | — | $\leq 1800$ | $\leq 1800$ | — |

| | |
|---|---|
| Solubility: | The Cremophor RH grades from clear solutions in water, ethanol, 2-propanol, and n-propanol. When Cremophor RH 60 is dissolved in completely anhydrous alcohols, it may be necessary to add 0.5–1% of water to obtain a clear solution.<br>With rising temperature, the solubility in water decreases, and at a certain temperature, the solution begins to become turbid. |

As those skilled in the art will recognize, within the parameters of the present invention, many combinations of glycerol fatty acid esters and/or polyethylene glycol fatty acid esters are possible which will provide vehicles having beneficial uses similar to the specific vehicles described above, and all such combinations are intended to be within the scope of the present invention.

The vehicles of the present invention may also contain, in addition to the fatty acid esters of glycerol and/or fatty acid esters of polyethylene glycol, various other ingredients such as polyethylene glycol (particularly low molecular weight PEG, such as below an average molecular weight of about 1500), propylene glycol, ethanol, and the like, so long as the HLB value of the final vehicle remains at least about 10. Other suitable vehicle ingredients will be readily apparent to those skilled in the art in view of the present disclosure. Such additional vehicle ingredients may be added, for example, to increase the solubility of the cyclic urea antiviral agent in the vehicle, which may, in turn, have the benefit of requiring smaller or fewer dosage units to administer a certain dose by increasing bioavailability. Other commonly used pharmaceutical excipients which may also be added to these compositions include antioxidants, preservatives or stabilizing agents, such as butylated hydroxytoluene, butylated hydroxyanisole sodium bisulfide, sodium sulfite, citric acid, ascorbic acid, or EDTA, coloring agents and flavoring agents (to improve patient acceptance, especially for liquid dosage forms), and ingredients used to stabilize gelatin capsules, such as glycerine, gelatin, or water.

Although amounts may vary widely, as those skilled in the art will recognize, by way of general guidance, the amount of these additional vehicle components is preferably less than about 50%, based on the total weight of the vehicle. More preferrably, the amount of the additional vehicle compound is less than about 40%, even more preferably less than about 30%, and most preferably less than about 20%, based on the total weight of the vehicle. Preferably, the fatty acid esters of glycerol and fatty acid esters of polyethylene glycol are present in the vehicle in an amount by weight, based on the total weight of the vehicle, of at least about 50%, more preferably at least about 60%, even more preferably, at least about 70%, and most preferably at least about 80%. The specific amounts of each vehicle component will be well within the ambit of those skilled in the art, once armed with the subject disclosures.

The vehicle may be solid or liquid.

The vehicles of the invention provide an effective means for attaining good systemic absorption of cyclic urea type compounds, such as those of Formula (I) herein, upon enteral administration, particularly oral administration. The term bioavailability, as used herein, denotes the ability of the cyclic urea compounds to be systemically absorbed by a patient upon enteral administration. Oral bioavailability thus refers to systemic absorption of the compounds when administered orally. The compositions of the invention provide for good oral bioavailability, in that generally at least about 30% of the dose is systemically absorbed. Preferably at least about 50% of the dose of subject cyclic urea compounds is systemically absorbed, more preferably at least about 70%, and most preferably at least about 90–95%. Moreover, in accordance with the invention, the good bioavailability may be such that it may remain essentially constant as dose is increased, so that plasma or tissue concentrations of the cyclic urea compounds also increase with increasing dose. Thus, the subject compositions may allow for good systemic absorption not only at low doses, but also at high dosage levels.

Although not intending to be bound by any theory of operation, the cyclic urea compounds of the invention have been found to have low aqueous solubility, and this property may be partly responsible for their generally poor oral bioavailability prior to the present invention. When many of these antiviral agents were dosed to animals with the antiviral agent in its solid state as in an aqueous suspension, for example, bioavailability was generally low.

The cyclic urea compounds of the invention are added to the vehicles of the invention to prepare the compositions of the invention. The cyclic urea compounds may be dispersed or dissolved in the vehicle, as desired, although preferably the compounds are dissolved. If the compounds are dispersed in the vehicle, the dispersions may be either homogenous or heterogeneous, but are preferably homogenous.

The concentrations of the cyclic urea antiviral agents in the compositions of the present invention may vary widely, as the skilled artisan will recognize. Typically, however, the cyclic urea compound is present in the composition in an amount of between about 0.5% to about 50% by weight, based on the total weight of the composition. Preferably, the cyclic urea compound is present in an amount of between about 2% and about 3% by weight, and most preferably between about 5% and about by weight.

Preferably, the concentrations of the cyclic urea compound are at or below the solubility concentration of the compound in the vehicle. This solubility concentration may be the solubility in the vehicle at an elevated temperature. One method of preparing these compositions is to heat the vehicle to 50°–150° C. and to dissolve the drug in the heated vehicle. Some of these compositions may be solid at room temperature. Heating the vehicle causes them to melt, and enables incorporation and homogenous dispersion of the antiviral agent in the composition. It is preferred that the antiviral agent is completely dissolved in the vehicle, which may be prepared at elevated temperatures. The compositions may be filled into capsules in the liquid or molten state at elevated temperatures, or may be filled as a solid.

In the preferred compositions of the invention, the cyclic urea compound is at a concentration that is at or below the solubility limit in the vehicle at room temperature or when heated to 50°–150° C. When vehicles were prepared wherein the drug concentration exceeded the solubility limit (e.g. a suspension), oral bioavailability was reduced compared to that of a solution vehicle. Therefore, it is preferrable that the vehicles have good solubility of the antiviral drugs. Drug solubility in the vehicle determines the maximum drug concentration in the dosage form that can be prepared without loss of bioavailability. Maximum drug concentrations are desired so that the dosing units (in terms of volume or mass of vehicle, or number of capsules) are minimized. It should also be understood that the term drug solubility in solution can refer to vehicles which are solid at room temperature, but which would generally be prepared by dissolving the drug in the melted vehicle at some elevated temperature.

Although, as one skilled in the art will recognize, the amount of each composition component may vary widely, a preferable range of components in the compositions of the invention is, by weight: between about 40% and about 95% fatty acid esters of glycerol, fatty acid esters of polyethylene glycol, or mixtures thereof; between about 5% and about 50% additional vehicle components; and between about 0.5% and about 50% cyclic urea type compound. A further preferable range of composition components is, by weight: between about 50% and about 90% fatty acid esters of glycerol, fatty acid esters of polyethylene glycol, or mixtures thereof; between about 10% and about 40% additional vehicle components; and between about 5% and about 25% cyclic urea type compound.

The compositions of the present invention may be advantageously used to treat viral infections, such as HIV infections, in a patient. The patient may be any type of mammal, but is preferably a primate, and most preferably a human. The compounds of the invention may act to inhibit HIV replication by acting as a protease inhibitor. To carry out the methods of the invention, a patient is generally administered a therapeutically effective amount of a composition of the invention. By therapeutically effective amount, it is meant a composition containing an amount of the cyclic urea compound effective to treat the viral infection in the patient. In the case of an HIV infection, such an amount may be the amount that is effective to inhibit the replication of HIV.

The compositions of the invention may be administered to the patient by any conventional means available for the use in conjunction with pharmaceuticals, and can be advantageously administered enterally, most preferably orally. Other suitable enteral modes of administration include rectal administration. They may be administered, particularly where oral administration is desired, for example, in solid dosage forms, such as capsules, tablets, and powders, or in liquid dosage forms, such as elixirs, syrups, and suspensions. The terms oral agent, oral inhibitor, oral compound, or the like, as used herein, denote compounds which may be orally administered. The compositions of the invention may be administered alone, or with other therapeutic agents, as desired.

The dosage administered will, of course, vary depending on their use, and known factors such as the pharmacodynamic characteristics of the particular agent, its mode and route of administration, age, health, and weight of the recipient, nature and extent of symptoms, type of concurrent treatment, frequency of treatment, and the effect desired. Typically, dosage is initiated at lower levels and increased until the desired therapeutic effect is achieved. To treat HIV infection, for example, a daily oral dosage of active ingredient may be about 0,001 to 1000 mg/kg of body weight. Ordinarily, a dose of 0.1 to 500 mg/kg per day in divided doses one to four times a day or in sustained release form will be effective to obtain the desired results. Suitable dosage levels will be well within the ambit of those skilled in the art, once armed with the present disclosure.

Useful pharmaceutical dosage forms for administration of the compositions of this invention are illustrated below. By pharmaceutical dosage form, it is meant the physical form in which the compounds of the invention are administered to the patient. Typically, dosage forms suitable for administration contain about 1 milligram to 500 milligrams of active ingredient per unit. In the present pharmaceutical compositions, the active ingredient will ordinarily be present in an amount of about 0.5–50% by weight based on the total weight of the composition.

By way of dosage form example, gelatin capsules (either hard gelatin or soft gelatin) may be prepared which contain the compositions of the invention in the hollow interior thereof. Compressed tablets may also be prepared using the compositions in the invention. Both tablets and capsules may be manufactured as sustained release products to provide for continuous release of medication over a period of hours. Compressed tablets may be sugar coated or film coated to mask any unpleasant taste and protect the tablet from the atmosphere, or enteric coated for selective disintegration in the gastrointestinal tract. Examples of these dosage forms are described in more detail below.

Capsules

A large number of unit capsules are prepared for oral administration by filling standard two-piece hard gelatin capsules each with 400 milligrams of a melted composition of the invention containing 50 milligrams of the cyclic urea compound warmed to 50° C.

Soft Gelatin Capsules

A liquid composition of the invention containing 50 milligrams of the cyclic urea compound is prepared for oral administration and injected by means of a positive displacement pump into gelatin to form soft gelatin capsules. The capsules are washed and dried.

Tablets

A large number of tablets are prepared for oral administration by conventional procedures so that the dosage unit is 100 milligrams of active ingredient, of the cyclic urea compound in a solid vehicle in accordance with the present invention. Appropriate coatings may be applied to increase palatability or delay absorption.

Suitable pharmaceutical carriers, pharmaceutical dosage form and methods of preparing the pharmaceutical dosage forms are described in *Remington'S Pharmaceutical Sciences*, Gennaro, A. R., ed., Mack Publishing Company, Easton, Pa., and *The United States Pharmacopeia—The National Formulary*, Mack Publishing Company, Easton, Pa., standard reference texts in this field. The disclosures of the latest versions, at the time of filing this application, of each of these reference texts is hereby incorporated by reference herein, in their entirety.

This invention also includes combination products comprising pharmaceutical compositions comprising a cyclic HIV protease inhibitor compounds of Formula (I) in physical combination or in a single dosage unit with any other agent, to pharmaceutical kits containing these combination products, and to methods of using these combination products for the inhibition of HIV and treatment of HIV infection.

The invention is further described in the following examples. These examples are not intended to limit to scope of the appended claims.

EXAMPLES

Example 1

General Procedures

Vehicles were evaluated for their capacity to solubilize a cyclic urea compound. Several methods were used. In Method A, vehicles were heated to 70°–80° C. and weighed amounts of the cyclic urea compound were added incrementally until the compound no longer dissolved. This is a visual estimation of solubility. In Method B, vehicles were prepared as in Method A, then cooled to room temperature, and then reheated to 50° C. Suspensions were filtered at 50° C. and compound concentrations in the liltrate filtrate were measured using a high performance liquid chromatographic (HPLC) method, providing the results shown under Method B.

Specifically, the vehicles of Table 1 were prepared and evaluated for solubility of a cyclic urea antiviral agent. The agent for Example 1 was [4R—(4a, 5a, 6β, 7β)]-hexahydro-5,6-bis(hydroxy)-1,3-bis([(4 -hydroxymethyl)phenyl]methyl)-4,7-bis(phenylmethyl)-2 H-1,3-diazepin-2-one. This compound corresponds to Ex. No. 5U in the above-cited PCT Application WO 93/07128, and is sometimes hereinafter referred to as Ex. No. 5U. In Table 1, all percentages are by weight.

TABLE 1

| | | Solubility (mg/g) of Ex. No. 5U | |
|---|---|---|---|
| Vehicle | Composition (HLB value) | Method A Visual @ 70–80° | Method B Assayed @ 50° |
| A | PEG-8 | 187–203 | 181 |
| B | 75% PEG-8:25% propylene glycol | 219–230 | 192 |
| C | Oleic acid | <5 | |
| D | Glycerol oleate (3.8) | <5 | |
| E | Caprylic/capric triglyceride | <5 | 0.1 |
| F | Propylene glycol laurate (4) | <10 | 11 |
| G | 45% Olive oil:45% Labrafil M 1944 CS | <10 | |

TABLE 1-continued

| Vehicle | Composition (HLB value) | Solubility (mg/g) of Ex. No. 5U | |
|---|---|---|---|
| | | Method A Visual @ 70–80° | Method B Assayed @ 50° |
| | (4):10% ethanol | | |
| H | Gelucire 35/10 (10) | <36 | 19 |
| I | Gelucire 44/14 (14) | <74 | 30 |
| J | 86% Gelucire 44/14:14% PEG-8 | 75–90 | 70 |
| K | 50% Gelucire 44/14:50% PEG-8 | 130–145 | 101 |
| L | 86% Gelucire 44/14:14% PEG-32 | <75 | 32 |
| M | 86% Gelucire 44/14:14% PEG-150 | <74 | 29 |
| N | 86% Gelucire 44/14:14% propylene glycol | 115–130 | 73 |
| O | 75% Gelucire 44/14: 25% propylene glycol | 145–156 | 148 |
| P | PEG-4 laurate (9.3) | <90 | 70 |
| Q | PEG-8 laurate (13.0) | <90 | 50 |
| R | 86% PEG-8 laurate: 14% PEG-8 | 90–130 | 75 |
| S | PEG-8 stearate (11.1) | <90 | 58 |
| T | 86% PEG-8 stearate: 14% PEG-8 | 90–130 | 64 |
| U | PEG-40 stearate (16.9) | 90–130 | 74 |
| V | 86% PEG-40 stearate:14% PEG-8 | 90–130 | 97 |
| W | PEG-60 hydrogenated castor oil (15–17) | 65–91 | 73 |
| X | Labrasol (14) | 120–150 | 102 |

Many of the vehicles of Table 1 are amphiphilic. That is, part of their structure is hydrophilic and part is lipophilic. The HLB value expresses the balance of hydrophilicity and lipophilicity, with the HLB value increasing with increasing hydrophilicity. HLB values were given for some of the vehicles of Table 1, in parentheses. The solubility of the compound [4R-(4α, 5α, 6β, 7β)]-hexahydro-5,6-bis (hydroxy)-1,3-bis ([( 4-hydroxymethyl)phenyl]methyl)-4,7-bis(phenylmethyl)- 2H-1,3-diazepin-2-one in these vehicles was related to the vehicle hydrophilicity. Those vehicles containing glycerides and PEG esters with higher HLB values are preferred because of their greater capability for dissolving cyclic urea compounds.

The vehicles of Table 1 also show that the addition of polyethylene glycol or propylene glycol to vehicles comprised of glycerides and PEG esters resulted in increased solubility of the compound [4R-(4α, 5α, 6β, 7β]-hexahydro-5,6-bis(hydroxy)-1,3-bis([( 4-hydroxymethyl)phenyl]methyl)-4,7-bis(phenylmethyl)- 2H-1,3-diazepin-2-one (Ex. No. 5U).

EXAMPLE 2

Various formulations of cyclic urea antiviral agents were prepared. Vehicle ingredients were weighed and mixed on a hotplate at 70°–80° C. The compound [4 R-(4α, 5α, 6β, 7β)]-hexahydro-5,6-bis(hydroxy)- 1,3-bis[[(4-hydroxymethyl)phenyl]methyl)-4,7-bis(phenylmethyl)- 2H-1,3-diazepin-2-one (Ex. No. 5U) was added at concentrations near the maximum concentration dissolving in the vehicle at 70°–80° C. The molten vehicle was filled into hard gelatin capsules, and then allowed to cool. Some vehicles were liquid at room temperature and others were solid at room temperature. The compositions are set forth in Table 2A. In Table 2A, all percentages are by weight.

TABLE 2A

| Composition | Constituents |
|---|---|
| A | 90% PEG-8:10% Ex. No. 5U |
| B | 60% PEG-8:20% propylene glycol:20% Ex. No. 5U |
| C | 21.2% PEG-75:41.7% PEG-8:21.2% propylene glycol:0.9% sodium lauryl sulfate:15% Ex. No. 5U |
| D | 79.5% Gelucire 44/14:13% PEG-8:7.5% Ex. No. 5U |
| E | 60.3% Gelucire 44/14:22.5% propylene glycol:7.2% PEG-75:10% Ex. No. 5U |
| F | 52.5% Gelucire 44/14:35% PEG-8:12.5% Ex. No. 5U |
| G | 87.5% Labrasol:12.5% Ex. No. 5U |
| H | 70% Labrasol:17.5% PEG-150:12.5% Ex. No. 5U |
| I | 79.5% PEG-60 hydrogenated castor oil 13% PEG-8:7.5% Ex. No. 5U |

The compositions of Table 2A were then evaluated for their effect on oral bioavailability of the cyclic urea compound. Capsules were orally dosed to beagle dogs. Blood samples were taken at various times and plasma was separated. Plasma samples were analyzed for the concentration of the compound [4R-(4α, 5α, 6β, 7β)]-hyxahydro-5,6-bis(hydroxy)-1,3-bis[[(4-hydroxymethyl)phenyl]methyl)-4,7-bis(phenylmethyl)-2H-1,3-diazepin-2-one (Ex. No. 5U) using an extraction and HPLC method. Dogs were also dosed intravenously (iv) for comparison. The area under each plasma concentration vs. time curve (AUC) was calculated, and the percentage oral bioavailability (referred to subsequently as F) was calculated using the following formula:

$$F=(AUC^{oral} \times Dose^{iv}/AUC^{iv} \times Dose^{oral}) \times 100$$

As another indicator of absorbability, the maximum observed plasma concentrations were recorded, and these values are referred to as Cmax. Results are provided in Table 2B.

TABLE 2B

| Composition | Dose (mg) | F (%) (mean ± S.E.) | Cmax (μg/ml) |
|---|---|---|---|
| A | 100–140 | 49.6 ± 19.7 | 2.41 |
| B | 350 | 5.2 ± 1.8 | 1.18 |
| C | 350 | 4.7 ± 1.1 | 1.06 |
| D | 85–100 | 73.6 ± 17.3 | 3.60 |
| D | 350 | 49.5 ± 4.2 | 9.43 |
| E | 350 | 15.7 ± 4.2 | 2.27 |
| F | 350 | 7.0 ± 2.1 | 1.69 |
| G | 350 | 21.7 ± 1.5 | 2.56 |
| H | 350 | 21.7 | 2.33 |
| I | 350 | 36.5 ± 6.1 | 4.09 |

A conventional approach to formulating compounds with poor aqueous solubility is to use non-aqueous solvents, particularly PEG and propylene glycol. As shown in Table 2B, a glycol formulation (Composition A) provided adequate oral bioavailability at low doses. But when a higher dose was administered with a glycol-based formulation (Composition B), bioavailability was greatly reduced. Cmax was lower at the 350 mg dose than that observed at the lower dose. Therefore, it is apparent that with glycol-based formulations it was not possible to acheive increasing plasma concentrations of cyclic urea antiviral agents with increasing doses. The addition of sodium lauryl sulfate to the glycol-based formulation (Composition C) did not afford any improvement.

In contrast, compositions containing the cyclic urea antiviral agent in a vehicle consisting of glycerides and PEG esters (Composition D) provided good oral bioavailability of the agent at low and high doses. Plasma concentrations of Ex. No. 5U increased with increasing dose, as shown by Cmax values.

The improved oral bioavailability with Composition D is also clearly apparent in the plasma concentration vs. time profiles, which are provided in Table 2C. In Table 2C, plasma concentrations (mean±S.E.) were measured in dogs dosed orally at 350 mg Ex. No. 5U with a glycol-based composition (Composition B) or a composition containing glycerides and PEG esters (Composition D).

TABLE 2C

| Hours | Plasma Conc. of Ex. No. 5U | |
|---|---|---|
| | Composition B | Composition D |
| 0.25 | 0.86 ± 0.35 | No sample |
| 0.5 | 0.86 ± 0.31 | 1.42 ± 0.49 |
| 1 | 0.62 ± 0.22 | 6.43 ± 0.52 |
| 1.5 | 0.28 ± 0.10 | 9.07 ± 1.41 |
| 2 | 0.20 ± 0.06 | 6.14 ± 0.58 |
| 3 | 0.11 ± 0.04 | 2.39 ± 0.26 |
| 4 | 0.05 ± 0.02 | 1.17 ± 0.14 |
| 6 | 0.04 ± 0.02 | 0.35 ± 0.06 |
| 8 | 0.05 ± 0.04 | 0.14 ± 0.005 |
| 10 | No sample | 0.14 ± 0.003 |
| 12 | No sample | 0.08 ± 0.002 |
| 14 | No sample | 0.04 ± 0.002 |
| 16 | No sample | 0.02 ± 0.0005 |
| 24 | Negligible | 0.004 ± 0.004 |

EXAMPLE 3

The oral bioavailability of the antiviral agent which corresponds to Ex. No. 9Q from PCT Application WO 93/07128 (hereinafter sometimes referred to Ex. No. 9Q) was also examined. Compositions A and B were prepared by dissolving Ex. No. 9Q in a vehicle at 70°–80° C. For Composition A, 10 mg/ml of Ex. No. 9Q was dissolved in a vehicle consisting of PEG-8. For Composition B, 10 mg/ml of Ex. No. 9Q was dissolved in a vehicle consisting of a mixture 86% Gelucire 44/14 and 14% PEG-8. Composition A was allowed to cool to room temperature. Composition B was allowed to cool down to 40°–50°, and was then maintained in its molten state at that temperature. Rats were orally administered a 10 mg/kg dose of Ex. No. 9Q, as either Composition A or Composition B, and blood samples were collected at various times. Plasma was analyzed for the concentration of Ex. No. 9Q by measuring the extent of HIV protease inhibitory activity in the plasma, relative to plasma standards spiked with known concentrations of Ex. No. 9Q, as in Example 2. Results are provided in Table 3. Table 3 shows the plasma concentration vs. time profiles for Ex. No. 9Q in Rat #1, which was dosed with a glycol-based formulation (Composition A) and in Rats #2 and 3 which were dosed with a formulation comprised primarily of glycerides and PEG esters (Composition B).

TABLE 3

| | Composition A (Plasma Conc. of Ex. No. 9Q) | Composition B | |
|---|---|---|---|
| Hours | Rat #1 | Rat #2 | Rat #3 |
| 0.5 | 0.050 | 0.157 | 0.219 |
| 1 | 0.054 | 0.383 | 0.296 |
| 2 | 0.055 | 0.495 | 0.322 |
| 3 | 0.027 | 0.219 | 0.288 |
| 5 | 0.006 | 0.175 | 0.179 |

The oral absorption of Ex. No. 9Q was clearly greatly increased when administered in the composition containing glycerides and PEG esters, compared to the commonly used PEG vehicle.

EXAMPLE 4

The cyclic urea antiviral agents of this invention are generally poorly water-soluble. Poor water solubility could be related to low oral bioavailability and dose-related bioavailability. One effect of the formulation ingredients may be to alter water solubility. Water solubility in the presence of dilute concentrations of the formulation ingredients could then be related to oral bioavailability. Dilute formulation ingredients could mimic the dilution of an administered dosage form upon reaching the aqueous environment within the gastrointestinal tract. Aqueous solubility studies of cyclic urea antiviral agents were performed in the presence of dilute concentrations of possible formulation ingredients in this Example 4.

Specifically, aqueous solutions were prepared containing 4% (w/v) of the formulation ingredients listed. Excess solid compound [4R-(4α, 5α, 6β, 7β)]-hexahydro-5,6-bis (hydroxy)-1,3-bis ([(4-hydroxymethyl)phenyl]methyl)- 4,7-bis (phenylmethyl)-2H-1,3-diazepin-2-one (Ex. No. 5U) was added and the samples were mixed 24 hours. Samples were filtered, and Ex. No. 5U solubility was determined by measuring filtrate drug concentrations using HPLC.

TABLE 4

| Formulation ingredient | Ingredient HLB value | Ex. No. 5U solubility (μg/ml) |
|---|---|---|
| None | | 5 |
| PEG-8 | | 12 |
| Glycerol dilaurate | 4 | 11 |
| PEG-4 laurate | 9.3 | 81 |
| PEG-8 stearate | 11.1 | 44 |
| PEG-8 laurate | 13 | 283 |
| Gelucire 44/14 | 14 | 758 |
| Labrasol | 14 | 410 |
| PEG-60 hydrogenated castor oil | 15–17 | 715 |
| PEG-40 stearate | 16.9 | 718 |
| * | * | * |

*A solution containing glycerol oleate (HLB value 3.8) was also prepared, but this separated into two phases.

Water dispersibility of the formulation ingredients is preferred. Formulation ingredients with low HLB values (less than about 10%) were either not water dispersible or afforded no increase in aqueous solubility of Ex. No. 5U. Formulation ingredients consisting of PEG esters or mixtures of glycerides and PEG esters, particularly those with HLB values of 13 or greater, increased Ex. No. 5U aqueous solubility.

The disclosures of all of the references cited herein are hereby incorporated herein by reference, in their entirety.

Various modifications of the invention, in addition to those shown and described herein, will be apparent to those skilled in the art, from the foregoing description. Such modifications are intended to fall within the scope of the appended claims.

What is claimed is:

1. A pharmaceutical composition comprising:
(a) a therapeutically effective amount of compound of the Formula (I):

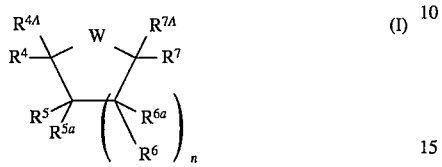

or a pharmaceutically acceptable salt or prodrug form thereof, wherein:

$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or 0–3 $R^{12}$;
a 5- to 10-membered heterocyclic ring system containing 1 to 4 heteroatoms independently selected from oxygen, nitrogen or sulfur, said heterocyclic ring system being substituted with 0–2 $R^{12}$; or
—$OR^{13}$; —$SR^{13}$; $CO_2R^{13}$;

$R^{4A}$ and $R^{7A}$ are independently selected from the following groups:
hydrogen;
$C_1$–$C_4$ alkyl substituted with 0–6 halogen or 0–3 $C_1$–$C_2$ alkoxy;
benzyl substituted with 0–6 halogen or 0–3 $C_1$–$C_2$ alkoxy; or —$OR^{13}$; —$SR^{13}$; $CO_2R^{13}$;

$R^4$ and $R^{4A}$ can alternatively join to form a 5–7 membered carbocyclic ring substituted with 0–2 $R^{12}$;

$R^7$ and $R^{7A}$ can alternatively join to form a 5–7 membered carbocyclic ring substituted with 0–2 $R^{12}$;

n is 1;

$R^5$ is selected from H; halogen; $C_1$–$C_6$ alkyl substituted with 0–3 $R^{11}$; —$N(R^{20})_2$; —$SR^{20}$; or —$OR^{20}$, —$N_3$;

$R^6$ is independently selected from: hydrogen, halogen, $C_1$–$C_6$ alkyl substituted with 0–3 $R^{11}$, —$N(R^{20})_2$, —$SR^{20}$, or —$OR^{21}$, —$N_3$;

$R^5$ and $R^6$ can alternatively join to form an epoxide or aziridine ring; —$OCH_2SCH_2O$—; —$OS(=O)O$—; —$OC(=O)O$—; —$OCH_2O$—; —$OC(=S)O$—; —$OC(=O)C(=O)O$—; —$OC(CH_3)_2O$—; —$OC((CH_2)_3NH_2)(CH_3)O$—; —$OC(OCH_3)(CH_2CH_2CH_3)O$—; —$OS(=O)O$—; —$NHC(=O)NH$—; —$OC(=O)NH$—; —$NHC(=O)O$—; —$NHCH_2O$—; —$OCH_2NH$—; —$NHC(=S)O$—; —$OS(=O)NH$—; —$NHC(=O)C(=O)O$—; —$OC(=O)C(=O)NH$—; —$NHC(=O)C(=O)NH$—; —$OC(CH_3)_2O$—; —$NHC(CH_3)_2O$—; —$OC(CH_3)_2NH$— or any group that, when administered to a mammalian subject, cleaves to form a free dihydroxyl or diamino or hydroxyl and amino;

$R^{5a}$ is selected from hydrogen, halogen, $C_1$–$C_6$ alkyl, —$N(R^{20})_2$, —$SR^{20}$, or —$OR^{20}$;

$R^{6a}$ is selected from: hydrogen, halogen, $C_1$–$C_6$ alkyl, —$N(R^{20})_2$, —$SR^{20}$ or —$OR^{21}$;

$R^5$ and $R^{5a}$ can alternatively join to form =O, =S, or a ketal ring;

$R^6$ and $R^{6a}$ can alternatively join to form =O, =S, or a ketal ring;

$R^{20}$ and $R^{21}$ are independently selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
$C_1$–$C_6$ alkylaminocarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$; or
any group that, when administered to a mammalian subject, cleaves to form a free hydroxyl, amino or sulfhydryl;

$R^{11}$ is selected from one or more of the following:
H, keto, halogen, cyano, —$CH_2NR^{13}R^{14}$, —$NR^{13}R^{14}$, —$CO_2R^{13}$, —$OC(=O)R^{13}$, —$O^{13}$, $C_2$–$C_6$ alkoxyalkyl, —$S(O)_mR^{13}$, —$NHC/(=NNH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, —$OP(O)(OR^{13})_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})=N(OR^{14})$;

1–3 amino acids linked together via amide bonds, said amino acid being linked via the amine or carboxylate terminus;

$C_3$–$C_{10}$ cycloalkyl substituted with 0–2 $R^{12}$;
$C_1$–$C_4$ alkyl substitued with 0–2 $R^{12}$
aryl($C_1$–$C_3$ alkyl) substituted with 0–2 $R^{12}$;
$C_2$–$C_6$ alkoxyalkyl, substituted with 0–2 $R^{12}$;
$C_1$–$C_4$ alkylcarbonyloxy substituted with 0–2 $R^{12}$,
$C_6$–$C_{10}$ arylcarbonyloxy substituted with 0–2 $R^{12}$,
a $C_5$–$C_{14}$ carbocyclic residue substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:
H, keto, halogen, cyano, —$CH_2NH_2$, —$NH_2$, —$NHMe$, —$CO_2H$, —$OC(=O)$ ($C_1$–$C_3$ alkyl), —$OH$, $C_2$–$C_6$ alkoxyalkyl, —$C(=O)NH_2$, —$OC(=O)NH_2$, —$NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, aryl($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ aralkyl, $C_1$–$C_4$ alkoxy, —$CO_2H$, hydroxamic acid, hydrazide, oronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl optionally substituted with —$Si(CH_3)_3$,, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkoxycarbonyl, $C_1$–$C_4$ alkylcarbonylamino, —$S(O)_mR^{13}$, —$SO_2NR^{13}R^{14}$, —$NHSO_2R^{14}$, —$OCH_2CO_2R^{13}$, 2-(1-morpholino)ethoxy, or —$C(R^{14})$=$N(OR^{14})$; or a 5-or 6-membered heterocyclic ring containing from 1 to 4 heteroatoms independently selected from oxygen, nitrogen or sulfur;

or $R^{12}$ may be a 3-or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, or —$C(R^{14})$=$N(OR^{14})$;

$R^{12A}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ aralkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, $C_1$–$C_4$ alkyl substituted with —$NH_2$, —$NH_2$, —$NHMe$, $C_2$–$C_6$ alkoxyalkyl optionally substituted with —$Si(CH_3)_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mMe$, —$SO_2NH_2$, —$NHSO_2Me$, —$OCH_2CO_2R^{13}$, 2-(1-morpholino)ethoxy, 13 $C($=$NOH)NH_2$; or a 5-or 6-membered heterocyclic ring containing from 1 to 4 heteroatoms independently selected from oxygen, nitrogen or sulfur;

or $R^{12A}$ may be a 3-or 4-carbon chain attached to adjacent carbons on the ring to form a fused 5-or 6-membered ring, said 5-or 6-membered ring being optionally substituted on the aliphatic carbons with halogen, $C_1$–$C_4$ alkyl, $C_1$–$C_4$ alkoxy, hydroxy, or —$NH_2$; or, when $R^{12A}$ is attached to a saturated carbon atom or sulfur, it may be =O or =S;

$R^{12A}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NH_2$, —$NH_2$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C($=$NOH)NH_2$;

$R^{13}$ is selected from:

H;

phenyl substituted with 0–3 $R^{11A}$;

benzyl substituted with 0–3 $R^{11A}$;

$C_1$–$C_6$ alkyl substituted with 0–3 $R^{11A}$;

$C_2$–$C_4$ alkenyl substituted with 0–3 $R^{11A}$;

$C_1$–$C_6$ alkylcarbonyl substituted with 0–3 $R^{11A}$;

$C_1$–$C_6$ alkoxycarbonyl substituted with 0–3 $R^{11A}$;

$C_1$–$C_6$ alkylaminocarbonyl substituted with 0–3 $R^{11A}$;

$C_3$–$C_6$ alkoxyalkyl substituted with 0–3 $R^{11A}$;

an amine protecting group when $R^{13}$ is bonded to N; or a hydroxy protecting group when $R^{13}$ is bonded to O;

$R^{14}$ is hydrogen, hydroxy, $CF_3$; $C_1$–$C_6$ alkyl substituted with 0–3 groups selected from OH, $C_1$–$C_4$ alkoxy, halogen, $NH_2$, $C_1$–$C_6$ alkoxy; $NH_2$; —$NH(C_1$–$C_4$ alkyl), $C_2$–$C_6$ alkenyl; phenyl, benzyl, an amine protecting group when $R^{14}$ is bonded to N, or a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

W is

—$N(R^{22})C($=$Z)N(R^{23})$—;

wherein:

Z is O;

$R^{22}$ and $R^{23}$ are independently selected from the following:

hydrogen;

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C_{14}$ carbocyclic ring system substituted with 0–5 $R^{31}$ or $R^{32}$;

a 5- to 10-membered heterocyclic ring system containing 1 to 4 heteroatoms independently selected from oxygen, nitrogen or sulfur, said heterocyclic ring system being substituted with 0–5 $R^{32}$; a 5-to 10-membered heterocyclic ring system containing 1 to 4 heteroatoms independently selected from oxygen, nitrogen or sulfur, said heterocyclic ring system being substituted with 0–5 $r^{32}$)

—$OR_{22a}$; or —$N(R^{22a})(R^{22b})$;

$R^{22a}$ and $R^{22b}$ are independently selected from the following:

hydrogen;

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C^{14}$ carbocyclic ring system substituted with 0–5 $R^{31}$ or $R^{32}$;

a 5- to 10-membered heterocyclic ring system containing 1 to 4 heteroatoms independently selected from oxygen, nitrogen or sulfur, said heterocyclic ring system being substituted with 0–5 $R^{32}$;

alternatively, $R^{22}$ can join with $R^4$ or $R^{44}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R_{23}$ can join with $R^7$ or $R^{7A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$ can join with $R^5$ or $R^6$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$ or $R^{23}$ are taken together with $R^5$ or $R^6$ to form a direct bond); or alternatively R23 can join with R7A to form a direct bond; or alternatively R22 can join with R4A to form a direct bond;

$R^{31}$ is selected from one or more of the following:

keto, halogen, cyano, $-CH_2NR^{13}R^{14}$, $-NR^{13}R^{14}$, $-CO_2R^{13}$, $-C(=O)R^{11}$, $-OC(=O)R^{13}$, $-OR^{13}$, $C_2-C_6$ alkoxyalkyl, $-S(O)_mR^{13}$, $-NHC(=NH)NHR^{13}$, $-C(=NH)NHR^{13}$, $-C(=O)NR^{13}R^{14}$, $-NR^{14}C(=O)R^{13}$, $=NOR^{14}$, $-NR^{14}C(=O)OR^{14}$, $-OC(=O)NR^{13}R^{14}$, $-NR^{13}C(=O)NR^{13}R^{14}$, $-NR^{13}C(=S)NR^{13}R^{14}$, $-NR^{14}SO_2NR^{13}R^{14}$, $-NR^{14}SO_2R^{13}$, $-SO_2NR^{13}R^{14}$, $C_1-C_4$ alkyl, $C_2-C_4$ alkenyl, $C_3-C_{10}$ cycloalkyl, $C_3-C_6$ cycloalkylmethyl, benzyl, phenethyl, phenoxy, benzyloxy, nitro, $C_7-C_{10}$ arylalkyl, hydroxamic acid, hydrazide, oxime, boronic acid, sulfonamide, formyl, $C_3-C_6$ cycloalkoxy, $C_1-C_4$ alkyl substituted with $-NR^{13}R^{14}$, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonylamino, $-OCH_2CO_2R^{13}$, 2-(1-morpholino)ethoxy, azido, $-C(R^{14})=N(OR^{14})$; or 1–3 amino acids, linked together via amide bonds, said amino acid being linked via the amine or carboxylate terminus;

a $C_5-C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenethyl, phenoxy, $C_3-C_{10}$ cycloalkyl, $C_3-C_6$ cycloalkylmethyl, $C_7-C_{10}$ arylalkyl, hydrazide, oxime, boronic acid, $C_2-C_6$ alkoxyalkyl, methylenedioxy, ethylenedioxy, $C_1-C_4$ alkylcarbonyloxy, $-NHSO_2R^{14}$, benzyloxy, halogen, 2-(1-morpholino)ethoxy, $-CO_2R^{13}$, hydroxamic acid, $-CONR^{13}NR^{13}R^{14}$, cyano, boronic acid, sulfonamide, $-CHO$, $C_3-C_6$ cycloalkoxy, $-NR^{13}R^{14}$, $-C(R^{14})=N(OR^{14})$, $NO_2$, $-OR^{13}$, $-N^{40}R^{41}$, $-SO_mR^{13}$, $-SO_mNR^{13}R^{13}$, $-C(=O)NR^{13}R^{14}$, $-OC(=O)NR^{13}R^{14}$, $-C(=O)R^{11}$, $-OC(=O)R^{11}$, $-CO_2R^{13}$, phenyl, $-C(=O)NR^{13}-(C_1-C_4$ alkyl$)-NR^{13}R^{14}$, $-C(=O)NR^{40}R^{41}$, $C_1-C_4$ haloalkyl, $C_1-C_4$ haloalkoxy, $C_2-C_4$ haloalkenyl, $C_1-C_4$ haloalkynyl, or $-C(=O)NR^{13}C(R^{11})_2NR^{13}R^{14}$;
$-C(=O)NR^{13}C(R^{11})_2NR^{13}NR^{14}$;
$-C(=O)NR^{13}C(R^{11})_2NR^{13}CO_2R^{13}$;
$-C(=O)NR^{13}-(C_1-C_4$ alkyl$)-NR^{13}CO_2R^{13}$;

$-C(=O)N(R^{13})-(C_1-C_4$ alkyl$)-R^{11}$; or
$-C(=O)C(R^{11})_2NR^{13}R^{14}$;
$-C(=O)C(R^{11})_2NR^{13}NR^{14}$;
$-C(=O)C(R^{11})_2NR^{13}CO_2R^{13}$;   $-C(=O)-(C_1-C_4$ alkyl$)-NR^{13}R^{14}$;
$-C(=O)-(C_1-C_4$ alkyl$)-NR^{13}CO_2R^{13}$; or $C_1-C_4$ alkoxy substituted with 0–4 groups selected from: $R^{11}$, $C_3-C_6$ cycloalkyl, $-CO_2R^{13}$, $-C(=O)NR^{13}R^{14}$, $-NR^{13}R^{14}$ or OH;

$C_1-C_4$ alkyl substituted with 0–4 groups selected from: $R^{11}$, $=NR^{14}$, $=NNR^{13}C(=O)NR^{13}R^{14}$ or $-NR^{13}R^{14}$, $=NNR^{13}C(=O)OR^{13}$;

$C_2-C_4$ alkenyl substituted with 0–4 $R^{11}$;

$C_2-C_4$ alkynyl substituted with 0–4 $R^{11}$;

a 5- or 6-membered heterocyclic ring containing from 1 to 4 heteroatoms independently selected from oxygen, nitrogen or sulfur, substituted with 0–2 $R^{12}$;

or $R^{32}$ may be a 3- or 4-carbon chain attached to adjacent carbons on the ring to form a fused 5- or 6-membered ring, said 5- or 6-membered ring being optionally substituted on the aliphatic carbons with halogen, $C_1-C_4$ alkyl, $C_1-C_4$ alkoxy, hydroxy, or $-NR^{13}R^{14}$; or, when $R^{32}$ is attached to a saturated carbon atom, it may be $=O$ or $=S$, $=NOH$; or when $R^{32}$ is attached to sulfur it may be $=O$;

$R^{32}$, when a substituent on nitrogen, is selected from one or more of the following:

phenyl, benzyl, phenethyl, hydroxy, $C_1-C_4$ hydroxyalkyl, $C_1-C_4$ alkoxy, $C_1-C_4$ alkyl, $C_3-C_6$ cycloalkyl, $C_3-C_6$ cycloalkylmethyl, $-CH_2NR^{13}R^{14}$, $-NR^{13}R^{14}$, $C_2-C_6$ alkoxyalkyl, $C_1-C_4$ haloalkyl, $C_1-C_4$ alkoxycarbonyl, $-CO_2H$, $C_1-C_4$ alkylcarbonyloxy, $C_1-C_4$ alkylcarbonyl, or $-C(R^{14})=N(OR^{14})$;

$R^{40}$ is selected from : H or $C_1-C_3$ alkyl;

$R^{41}$ is selected from:
$-C(=O)NR^{13}R^{14}$;
$-C(=O)NR^{13}NR^{13}R^{14}$;
$-C(=O)C(R^{11})_2NR^{13}R^{14}$;
$-C(=O)C(R^{11})_2NR^{13}NR^{13}R^{14}$;
$-C(=O)C(R^{11})_2NR^{13}CO_2R^{13}$;
$-C(=O)H$;
$-C(=O)R^{11}$;
$-C(=O)-(C_1-C_4$ alkyl$)-NR^{13}R^{14}$;
$-C(=O)-(C_1-C_4$ alkyl$)-NR^{13}CO_2R^{13}$;
1–3 amino acids linked together via amide bonds, and linked to the N atom via the carboxylate terminus;

provided that:

$R^4$, $R^{4A}$, $R^7$ and $R^{7A}$ are not all hydrogen;

when $R^4$, $R^{4A}$ are hydrogen, $R^{22}$ is not hydrogen; and (b) a vehicle comprising a fatty acid ester of glycerol, a fatty acid ester of polyethylene glycol, or mixture thereof, wherein said vehicle has a hydrophil-lipophil balance of at least about 10.

2. A composition of claim 1 wherein said vehicle comprises a fatty acid ester of glycerol.

3. A composition of claim 2 wherein said fatty acid ester of glycerol is selected from one or more of the group consisting of mono-, di-, and triesters of glycerol or glycerol derivatives, wherein the fatty acid substituent is caprylate, caprate, laurate, myristate, palmitate, stearate, oleate, linoleate, linolenate, ricinoleate, arachidate, behenate, or hydroxylated products of these fatty acids.

4. A composition of claim 3 wherein said fatty acid ester of glycerol is selected from one or more of the group consisting of glycerol monoesters wherein the fatty acid substituent is caprate, laurate, oleate, or hydroxylated products of these fatty acids.

5. A composition of claim 1 wherein said vehicle comprises a fatty acid ester of polyethylene glycol.

6. A composition of claim 5 wherein said fatty acid ester of polyethylene glycol is selected from one or more of the group consisting of PEG stearate, PEG hydrogenated castor oil, PEG laurate, PEG apricot kernel oil esters, PEG caprylate, PEG caprate, PEG myristate, PEG palmitate, and PEG oleate.

7. A composition of claim 6 wherein said fatty acid ester of polyethylene glycol is selected from one or more of the group consisting of PEG-40 stearate, PEG-60 hydrogenated castor oil, PEG-32 laurate, PEG-40 hydrogenated castor oil, PEG-32 dilaurate, PEG-6 ethoxylated persic oil esters, PEG-8 caprylate, and PEG-8 caprate.

8. A composition of claim 1 wherein said vehicle comprises a mixture of a fatty acid ester of glycerol and a fatty acid ester of polyethylene glycol.

9. A composition of claim 8 wherein said mixture of fatty acid ester of glycerol and fatty acid ester of polyethylene glycol is a mixture having the characteristics set forth in Table A.

10. A composition of claim 8 wherein said mixture of fatty acid ester of glycerol and fatty acid ester of polyethylene glycol is a mixture having the characteristics set forth in Table B.

11. A composition of claim 1 wherein said hydrophil-lipophil balance is at least about 12.

12. A composition of claim 11 wherein said hydrophil-lipophil balance is between about 12 and about 18.

13. A composition of claim 12 wherein said hydrophil-lipophil balance is about 14.

14. A composition of claim 1 wherein said vehicle is a solid vehicle.

15. A composition of claim 1 wherein said vehicle is a liquid vehicle.

16. A composition of claim 1 wherein said Formula (I) compound is dispersed in said vehicle.

17. A composition of claim 16 wherein said dispersion is a homogeneous dispersion.

18. A composition of claim 1 wherein said Formula (I) compound is dissolved in said vehicle.

19. A composition of claim 1 wherein said composition is for oral administration.

20. A composition of claim 19 wherein said composition has an oral bioavailability of said compound of Formula (I) of at least about 30%.

21. A composition of claim 20 wherein said composition has an oral bioavailability of said compound of Formula (I) of at least about 50%.

22. A composition of claim 1 wherein said composition comprises between about 0.5% and about 50% of said compound of Formula (I) and between about 40% and about 95% of said fatty acid esters of glycerol, fatty acid esters of polyethylene glycol, or a mixture thereof.

23. A composition of claim 22 wherein said composition comprises between about 5% and about 20% of said compound of Formula (I) and between about 50% and about 90% of said fatty acid esters of glycerol, fatty acid esters of polyethylene glycol, or a mixture thereof.

24. A composition of claim 1 wherein said vehicle comprises additional vehicle components.

25. A composition of claim 24 wherein said additional vehicle components are selected from the group consisting of polyethylene glycol, propylene glycol, ethanol, or mixtures thereof.

26. A composition of claim 25 wherein said composition comprises between about 0.5% and about 50% of said compound of Formula (I) and between about 40% and about 95% of said fatty acid esters of glycerol, fatty acid esters of polyethylene glycol, or a mixture thereof, and between about 5% and about 50% of said additional vehicle components.

27. A composition of claim 26 wherein said composition comprises between about 0.5% and about 50% of said compound of Formula (I) and between about 40% and about 95% of said fatty acid esters of glycerol, fatty acid esters of polyethylene glycol, or a mixture thereof, and between about 10% and about 35% of said additional vehicle components.

28. A composition of claim 1 wherein, in said compound of Formula (I):

$R^4$ and $R^7$ are independently selected from the following groups:
hydrogen;
$C_1$–$C_4$ alkyl substituted with 0–3 $R^{11}$;
$C_3$–$C_4$ alkenyl substituted with 0–3 $R^{11}$; or
$C_3$–$C_4$ alkynyl substituted with 0–3 $R^{11}$;

$R^{4A}$ and $R^{7A}$ are hydrogen;

n is 1;

$R^5$ is selected from fluoro or —$OR^{20}$;

$R^6$ is independently selected from: hydrogen, fluoro or —$OR^{21}$;

$R^5$ and $R^6$ can alternatively join to form an epoxide or aziridine ring; —$OCH_2SCH_2O$—; —$OS(=O)O$—; —$OC(=O)O$—; —$OCH_2O$—; —$OC(=S)O$—; —$OC(=O)C(=O)O$—; —$OC(CH_3)_2O$—; —$OC(OCH_3)(CH_2CH_2CH_3)O$—; or any group that, when administered to a mammalian subject, cleaves to form a free dihydroxyl;

$R^{5a}$ is selected from hydrogen or fluoro;

$R^{6a}$ is selected from: hydrogen or fluoro;

$R^5$ and $R^{5a}$ can alternatively join to form =O, =S, or a ketal ring;

$R^6$ and $R^{6a}$ can alternatively join to form =O, =S, or a ketal ring;

$R^{20}$ and $R^{21}$ are independently selected from:
hydrogen;
$C_1$–$C_6$ alkylcarbonyl;
$C_1$–$C_6$ alkoxycarbonyl; benzoyl; or
any group that, when administered to a mammalian subject, cleaves to form a free hydroxyl;

$R^{11}$ is selected from one or more of the following:
H, keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_4$ alkoxyalkyl, —$S(O)_mR^{13}$, $C_1$–$C_4$ alkyl, $C_2$–$C_4$ alkenyl, or $C_3$–$C_{10}$ cycloalkyl;

a $C_5$–$C_{14}$ saturated or partially unsaturated carbocyclic residue substituted with 0–3 $R^{12}$;

aryl($C_1$–$C_3$ alkyl) substituted with 0–2 $R^{12}$;

aryl substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–2 $R^{12}$;

$R^{12}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, 2-(1-morpholino)ethoxy, —$CO_2H$, hydroxamic acid, hydrazide, —C($R^{14}$)=N(O$R^{14}$), cyano, oxime, boronic acid, sulfonamide, formyl, $C_3$–$C_6$ cycloalkoxy, —O$R^{13}$, $C_1$–$C_4$ alkyl substituted with —N$R^{13}R^{14}$, —N$R^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m R^{13}$, —SO$_2$N$R^{13}R^{14}$, or —NHSO$_2R^{14}$; or a 5- or 6-membered heterocyclic ring containing from 1 to 4 heteroatoms independently selected from oxygen, nitrogen or sulfur;

or $R^{12}$ may be a 3- or 1-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —N$R^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$N$R^{13}R^{14}$, —N$R^{13}R^{14}$, $C_2$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl, or —CO$_2$H;

$R^{13}$ is H, $C_1$–$C_6$ alkyl, $C_3$–$C_6$ alkoxyalkyl, $C_2$–$C_4$ alkenyl, phenyl, or benzyl;

$R^{14}$ is OH, H, CF$_3$, $C_1$–$C_4$ alkyl, $C_1$–$C_4$ alkoxy, NH$_2$, $C_2$–$C_4$ alkenyl, phenyl, or benzyl;

$R^{13}$ and $R^{14}$ can alternatively join to form —(CH$_2$)$_4$—, —(CH$_2$)$_5$—, —CH$_2$CH$_2$N($R^{15}$)CH$_2$CH$_2$—, or —CH$_2$CH$_2$OCH$_2$CH$_2$—;

$R^{15}$ is H or CH$_3$;

m is 0, 1 or 2;

W is

—N($R^{22}$)C(=Z)N($R^{23}$)—;

wherein:

Z is O;

$R^{22}$ and $R^{23}$ are independently selected from the following:

hydrogen;

$C_1$–$C_8$ alkyl substituted with 0–3 $R^{31}$;

$C_3$–$C_8$ alkenyl substituted with 0–3 $R^{31}$;

$C_3$–$C_8$ alkynyl substituted with 0–3 $R^{31}$; or $C_3$–$C_6$ cycloalkyl substituted with 0–3 $R^{31}$;

$R^{31}$ is selected from one or more of the following:

keto, halogen, cyano, —CH$_2$N$R^{13}R^{14}$, —N$R^{13}R^{14}$, —CO$_2R^{13}$, —OC(=O)$R^{13}$, —O$R^{13}$, $C_2$–$C_4$ alkoxyalkyl, —S(O)$_m R^{13}$, $C_1$–$C_4$ alkyl, $C_2$–$C_4$ alkenyl, $C_3$–$C_{10}$ cycloalkyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —N$R^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, or —C($R^{14}$)=N(O$R^{14}$); or a $C_5$–$C_{14}$ saturated or partially unsaturated carbocyclic residue substituted with 0–3 $R^{32}$;

aryl substituted with 0–3 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenethyl, phenoxy, $C_3$–$C_6$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —NHSO$_2R^{14}$, benzyloxy, halogen, 2-(1-morpholino)ethoxy, —CO$_2R^{13}$, hydroxamic acid, —CON$R^{13}$N$R^{13}R^{14}$, cyano, boronic acid, sulfonamide, —CHO, $C_3$–$C_6$ cycloalkoxy, —N$R^{13}R^{14}$, —C($R^{14}$)=N(O$R^{14}$), NO$_2$, —O$R^{13}$, —N$R^{40}R^{41}$, —SO$_m R^{13}$, —SO$_m$N$R^{13}R^{14}$, —C(=O)N$R^{13}R^{14}$, —OC(=O)N$R^{13}R^{14}$, —C(=O)$R^{11}$, —OC(=O)$R^{11}$, —OCO$_2R^{13}$, phenyl, —C(=O)N$R^{13}$-($C_1$–$C_4$ alkyl)-N$R^{13}R^{14}$, —C(=O)N$R^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or —(=O)N$R^{13}$C($R^{11}$)$_2$N$R^{13}R^{14}$; —C(=O)N$R_{13}$C($R^{11}$)$_2$N$R^{13}$N$R^{14}$;

—C(=O)N$R^{13}$C($R^{11}$)$_2$N$R^{13}$CO$_2R^{13}$;

—C(=O)N$R^{13}$-($C_1$–$C_4$ alkyl)—N$R^{13}$CO$_2R^{13}$; or

—C(=O)C($R^{11}$)$_2$N$R^{13}R^{14}$;

—C(=O)C($R^{11}$)$_2$N$R^{13}$N$R^{14}$;

—C(=O)C($R^{11}$)$_2$N$R^{13}$CO$_2R^{13}$; —C(=O) -($C_1$–$C_4$ alkyl)—N$R^{13}R^{14}$;

—C(=O)-($C_1$–$C_4$ alkyl)—N$R^{13}$CO$_2R^{13}$; or $C_1$–$C_4$ alkoxy substituted with 0–3 groups selected from: $R^{11}$, $C_3$–$C_6$ cycloalkyl, —CO$_2R^{13}$, —C(=O)N$R^{13}R^{14}$, —N$R^{13}R^{14}$ or OH;

$C_1$–$C_4$ alkyl substituted with 0–3 groups selected from: $R^{11}$, =N$R^{14}$, =NN$R^{13}$C(=O)N$R^{13}R^{14}$ or —N$R^{13}R^{14}$;

$C_2$–$C_4$ alkenyl substituted with 0–3 $R^{11}$;

$C_2$–$C_4$ alkynyl substituted with 0–3 $R^{11}$;

a 5- or 6-membered heterocyclic ring containing from 1 to 4 heteroatoms independently selected from oxygen, nitrogen or sulfur, substituted with 0–2 $R^{12}$;

or $R^{32}$ may be a 3-or 4-carbon chain attached to adjacent carbons on the ring to form a fused 5- or 6-membered ring, said 5-or 6-membered ring being optionally substituted on the aliphatic carbons with halogen, $C_1$–$C_4$ alkyl, $C_1$–$C_4$ alkoxy, hydroxy, or —N$R^{13}R^{14}$; or, when $R^{32}$ is attached to a saturated carbon atom, it may be =O or =S; or when $R^{12}$ is attached to sulfur it may be =O;

$R^{32}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$N$R^{13}R^{14}$, —N$R^{13}R^{14}$, $C_2$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl, —CO$_2$H, or —C($R^{14}$)=N(O$R^{14}$);

$R^{40}$ is selected from: H, $C_1$–$C_3$ alkyl;

$R^{41}$ is selected from:

—C(=O)N$R^{13}R^{14}$;

—C(=O)N$R^{13}$N$R^{13}R^{14}$;

—C(=O)C($R^{11}$)$_2$N$R^{13}R^{14}$;

—C(=O)C($R^{11}$)$_2$N$R^{13}$N$R^{13}R^{14}$;

—C(=O)C($R^{11}$)$_2$N$R^{13}$CO$_2R^{13}$;

—C(=O)H;
—C(=O)R$^{11}$;
—C(=O)-(C$_1$-C$_4$ alkyl)—NR$^{13}$R$^{14}$;
—C(=O)-(C$_1$-C$_4$ alkyl)—NR$^{13}$CO$_2$R$^{13}$; or
1–3 amino acids linked together via amide bonds, and linked to the N atom via the carboxylate terminus;
provided that:
R$^4$, R$^{4A}$, R$^7$, and R$^{7A}$ are not all hydrogen; and
when R$^4$ and R$^{4A}$ are hydrogen, R$^{22}$ is not hydrogen.

29. A composition of claim 1 wherein said compound of Formula (I) is a compound of formula:

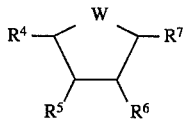

or a pharmaceutically acceptable salt thereof,
wherein:
R$^4$ and R$^7$ are independently selected from the following groups:
hydrogen;
C$_1$-C$_3$ alkyl substituted with 0–1 R$^{11}$;
R$^5$ is —OR$^{20}$;
R$^6$ is hydrogen or —OR$^{21}$;
R$^{20}$ and R$^{21}$ are independently hydrogen or any group that, when administered to a mammalian subject, cleaves to form a free hydroxyl;
R$^{11}$ is selected from one or more of the following:
H; halogen; —OR$^{13}$;
C$_3$-C$_{10}$ cycloalkyl substituted with 0–2 R$^{12}$;
C$_1$-C$_4$ alkyl substituted with 0–2 R$^{12}$;
aryl(C$_1$-C$_3$ alkyl) substituted with 0–2 R$^{12}$;
aryl substituted with 0–2 R$^{12}$; or
a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 R$^{12}$;
R$^{12}$, when a substituent on carbon, is selected from one or more of the following:
benzyloxy, halogen, methyl, C$_1$-C$_4$ alkoxy, CF$_3$, 2-(1-morpholino)ethoxy, —CO$_2$H, hydroxamic acid, hydrazide, —(R$^{14}$)=N(OR$^{14}$), cyano, boronic acid, sulfonamide, formyl, C$_3$-C$_6$ cycloalkoxy, C$_1$-C$_4$ alkyl substituted with —NR$^{13}$R$^{14}$, —NR$^{13}$R$^{14}$, hydroxy, hydroxymethyl; or
R$^{12}$, when a substituent on nitrogen, is methyl;
R$^{13}$ is H, C$_1$-C$_4$ alkyl, C$_2$-C$_4$ alkenyl, or benzyl;
R$^{14}$ is OH, H, CF$_3$, C$_1$-C$_4$ alkyl, C$_1$-C$_4$ alkoxy, NH$_2$, C$_2$-C$_4$ alkenyl, or benzyl;
R$^{13}$ and R$^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;
R$^{15}$ is H or CH$_3$;
W is selected from:
—N(R$^{22}$)C(=Z)N(R$^{23}$)—;
Z is O,
R$^{22}$ and R$^{23}$ are independently selected from the following:
hydrogen;
C$_1$-C$_8$ alkyl substituted with 0–3 R$^{31}$;
C$_2$-C$_6$ alkenyl substituted with 0–3 R$^{31}$; or
C$_2$-C$_4$ alkynyl substituted with 0–3 R$^{31}$;
R$^{31}$ is selected from one or more of the following:
halogen, —OR$^{13}$, C$_1$-C$_4$ alkyl, C$_3$-C$_{10}$ cycloalkyl, —(R$^{14}$)=N(OR$^{14}$), —CO$_2$R$^{13}$, —S(O)$_m$R$^{13}$;
aryl substituted with 0–5 R$^{32}$; or
a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 R$^{32}$;
R$^{32}$, when a substituent on carbon, is selected from one or more of the following:
benzyloxy, halogen, 2-(1-morpholino)ethoxy, —CO$_2$R$^{13}$, hydroxamic acid, —CONR$^{13}$NR$^{13}$R$^{14}$, cyano, boronic acid, sulfonamide, —CHO, C$_3$-C$_6$ cycloalkoxy, —NR$^{13}$R$^{14}$, —C(R$^{14}$)=N(OR$^{14}$), NO$_2$, —OR$^{13}$, —NR$^{40}$R$^{41}$, —SO$_m$R$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —OCO$_2$R$^{13}$,
phenyl, —C(=O)NR$^{13}$—(C$_1$-C$_4$ alkyl)—NR$^{13}$R$^{14}$, —C(=O)N$^{40}$R$^{41}$, C$_1$-C$_4$ haloalkyl, C$_1$-C$_4$ haloalkoxy, C$_2$-C$_4$ haloalkenyl, C$_1$-C$_4$ haloalkynyl, —C(=O)NR$^{13}$R$^{14}$; —C(=O)C(R$^{11}$)$_2$NR$^{13}$R$^{14}$; —C(=O)C(R$^{11}$)$_2$NR$^{13}$NR$^{14}$;
—C(=O)C(R$^{11}$)$_2$NR$^{13}$CO$_2$R$^{13}$; —C(=O)—(C$_1$-C$_4$ alkyl)—NR$^{13}$R$^{14}$; —C(=O)-(C$_1$-C$_4$ alkyl)-NR$^{13}$CO$_2$R$^{13}$; or
C$_1$-C$_4$ alkoxy substituted with 0–3 groups selected from: R$^{11}$, C$_3$-C$_6$ cycloalkyl, —C(=O)NR$^{13}$R$^{14}$, —NR$^{13}$R$^{14}$ or OH;
C$_1$-C$_4$ alkyl substituted with 0–3 groups selected from: R$^{11}$, =NR$^{14}$, =NNR$^{13}$C(=O)NR$^{13}$R$^{14}$ or —NR$^{13}$R$^{14}$;
C$_2$-C$_4$ alkenyl substituted with 0–3 R$^{11}$;
C$_2$-C$_4$ alkynyl substituted with 0–3 R$^{11}$;
a 5- or 6-membered heterocyclic ring containing from 1 to 4 heteroatoms independently selected from oxygen, nitrogen or sulfur;
R$^{32}$, when a substituent on nitrogen, is methyl;
m is 0, 1, or 2;
R$^{40}$ is selected from: H, or C$_1$-C$_3$ alkyl;
R$^{41}$ is selected from:
—C(=O)NR$^{13}$R$^{14}$;
—C(=O)NR$^{13}$NR$^{13}$R$^{14}$;
—C(=O)C(R$^{11}$)$_2$NR$^{13}$R$^{14}$;
—C(=O)C(R$^{11}$)$_2$NR$^{13}$NR$^{13}$R$^{14}$;
—C(=O)C(R$^{11}$)$_2$NR$^{13}$CO$_2$R$^{13}$;
—C(=O)H;
—C(=O)R$^{11}$;
—C(=O)-(C$_1$-C$_4$ alkyl)—NR$^{13}$R$^{14}$;
—C(=O)-(C$_1$-C$_4$ alkyl)—NR$^{13}$CO$_2$R$^{13}$;
1–3 amino acids linked together via amide bonds, and linked to the N atom via the carboxylate terminus;
provided that:
R$^4$ and R$^7$ are not both hydrogen;
when W is —C(=Z)—, R$^4$ and R$^7$ are not hydrogen; and
when R$^4$ is hydrogen, is not hydrogen R$^{22}$.

30. A composition of claim 29 wherein, in said compound of Formula (I):
R$^4$ and R$^7$ are selected from benzyl, fluorobenzyl, pyrrolylmethyl, methoxybenzyl, isobutyl, nitrobenzyl aminobenzyl, thienylmethyl, or hydroxybenzyl;
R$^5$ is —OH;
R$^6$ is hydrogen or —OH;

R$^{13}$ is H, C$_1$–C$_4$ alkyl, C$_2$–C$_4$ alkenyl, or benzyl;

R$^{14}$ is OH, H, CF$_3$, C$_1$–C$_4$ alkyl, C$_1$–C$_4$ alkoxy, NH$_2$, C$_2$–C$_4$ alkenyl, or benzyl;

R$^{13}$ and R$^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

W is selected from:

R$^{22}$ and R$^{23}$ are independently selected from the following:
  hydrogen;
  C$_1$–C$_8$ alkyl substituted with 0–2 R$^{31}$;
  C2–C$_6$ alkenyl substituted with 0–2 R$^{31}$; or
  C$_2$–C$_4$ alkynyl substituted with 0–2 R$^{31}$;

R$^{31}$ is selected from one or more of the following:
  halogen, —OR$^{13}$, C$_1$–C$_4$ alkyl, C$_3$–C$_{10}$ cycloalkyl, —(R$^{14}$)=N(OR$^{14}$), —CO$_2$R$^{13}$, —S(O)$_m$R$^{13}$;
  aryl substituted with 0–5 R$^{32}$; or
  a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, benzimidazolyl, benzotriazolyl, indazolyl, benzoxazolinyl, benzoxazolyl, said heterocyclic ring being substituted with 0–2 R$^{32}$;

R$^{32}$, when a substituent on carbon, is selected from one or more of the following:
  —CONH$_2$, —CO$_2$H, —CHO, —CH$_2$NHOH, —CH$_2$NR$^{13}$R$^{14}$, —NR$^{13}$R$^{14}$, hydroxy, hydroxymethyl, —C(R$^{14}$)=N(OR$^{14}$), halogen, methoxy, methyl, nitro, cyano, allyloxy, —CO$_2$CH$_3$, —NHCHO, —NHCOCH$_3$, —OCO$_2$CH$_3$, —CH=NCH$_2$CH$_2$OH, —OCONHCH$_2$C$_6$H$_5$, —OCONHCH$_3$, oxazolidinyl, —C=CH$_2$OH, —COCH$_3$, hydroxyethyl, C$_1$–C$_3$ alkyl (said alkyl substituted with 0–4 halogen, or OH), tetrazolyl, —OCH$_2$CONH$_2$, —CONHNH$_2$, —CH=NNHCONH$_2$, —CONHOCH$_3$, —CH$_2$CH(OH)CH$_2$OH, adamantamido, hydroxyethoxy, dihydroxyethyl, —C(NH$_2$)=NH, —CONHCH$_3$, —B(OH)$_2$, benzyloxy, —CONHCH$_2$CH$_3$, —CON(CH$_2$CH$_3$)$_2$, methylthio, —SO$_2$CH$_3$, —NHCONH$_2$, —NHCONHCH$_3$, —NHCOCH$_2$N(CH$_3$)$_2$, —NHCOCH$_2$NHCH$_3$, —NHCOCH$_2$NHCO$_2$CH$_2$C$_6$H$_5$, —NHCOCH$_2$NH$_2$, —NHCOCH(CH$_3$)NHCO$_2$CH$_2$C$_6$H$_5$, —NHCOCH(CH$_2$C$_6$H$_5$)NHCO$_2$CH$_2$C$_6$H$_5$, —NHCOCH(CH$_3$)NH$_2$, —NHCOCH(CH$_2$C$_6$H5)NH$_2$, —CO$_2$CH$_2$CH$_3$, —CONHCH$_2$CH$_3$, —CONHCH(CH$_3$)$_2$, —CH$_2$-imidazole, —COC(CH$_3$)$_3$, —CH(OH)CF$_3$, —CO-imidazole, —CO-pyrazolyl, oxadiazolidinonyl, —COCF$_3$, —COCH$_2$CH$_3$, —COCH$_2$CH$_2$CH$_3$, pyrazolyl, —SO$_2$NH$_2$, —C(CH$_2$CH$_3$)=N(OH) or —C(CF$_3$)=N(OH), phenyl, acetoxy, hydroxyamino, —N(CH$_3$)(CHO), cyclopropylmethoxy, —CONR$^{13}$R$^{14}$, —CONHOH, (diethylaminoethyl)aminocarbonyl, (N-ethyl, N-methylaminoethyl)aminocarbonyl, (4-methylpiperazinylethyl)aminocarbonyl, pyrrolidinylethyl)aminocarbonyl, (piperidinylethyl)aminocarbonyl, —NHCOCH$_2$NHCH$_3$, N-(2-(4-morpholino)ethyl)aminocarbonyl, or N-( 2-(N,N-dimethylamino)ethyl)aminocarbonyl; and R$^{32}$ when a substituent on nitrogen, is methyl.

31. A composition of claim 1 wherein said compound of Formula (I) is a compound of the formula:

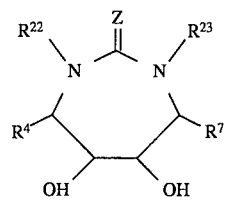

wherein:

Z is O.

R$^4$ and R$^7$ are independently selected from: benzyl, fluorobenzyl, pyrrolylmethyl, methoxybenzyl, isobutyl, nitrobenzyl aminobenzyl, thienylmethyl, or hydroxybenzyl;

R$^{22}$ and R$^{23}$ are independently selected from the group consisting of:
  hydrogen, allyl, methyl, ethyl, propyl, cyclopropylmethyl, n-butyl, i-butyl, CH$_2$CH=C(CH$_3$)$_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, (H$_2$NC(=O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, (CH$_3$C(=NOH))-benzyl, (H$_2$NNHC(=O))-benzyl, (H$_2$NC(=O)NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_2$O)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, (H$_2$NSO$_2$)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl)benzyl, (CF$_3$C(=NOH))-benzyl, (N-methylglycyl)aminobenzyl, ((4-morpholino) ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C-C(=O))benzyl, (N-methyl-N-ethylaminoethyl)aminocarbonylbenzyl, (pyrrolidinylethyl)aminocarbonylbenzyl, or (piperidinylethyl)aminocarbonylbenzyl, (H$_2$NC(=NOH))benzyl, (H$_2$NC(=NOH))fluorobenzyl, benzimidazolylmethyl, benzotriazolylmethyl, indazolylmethyl, benzoxazolinylmethyl, benzisoxazolylmethyl, thienylmethyl, furylmethyl.

32. A composition of claim 1 wherein said compound of Formula (I) is a compound of the formula:

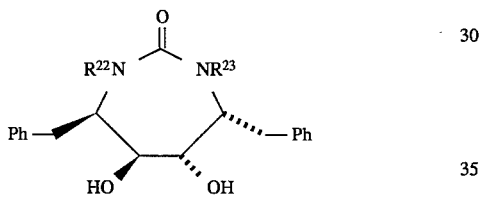

wherein R$^{22}$ and R$^{23}$ are independently selected from the group consisting of:

hydrogen, allyl, methyl, ethyl, propyl, cyclopropylmethyl, n-butyl, i-butyl, CH$_2$CH=C(CH$_3$)$_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, (H$_2$NC(=O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl) ethylbenzyl, (CH$_3$C(=NOH))-benzyl, (H$_2$NNHC (=O))-benzyl, (H$_2$NC(=O) NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_2$O)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, (H$_2$NSO$_2$)-benzyl, dihydroxyethylbenzyl, (MeHNC (=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl)-benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino )benzyl, (imidazolylmethyl)benzyl, ((CH$_3$)$_3$C-C(=O))benzyl, (N-methyl-N-ethylaminoethyl)aminocarbonylbenzyl, (pyrrolidinylethyl)aminocarbonylbenzyl, or (piperidinylethyl)aminocarbonylbenzyl, (H$_2$NC(=NOH))benzyl, (H$_2$NC(=NOH))fluorobenzyl, benzimidazolylmethyl, benzotriazolylmethyl, indazolylmethyl, benzoxazolinylmethyl, benzisoxazolylmethyl, thienylmethyl, furylmethyl.

33. A composition of claim 1 wherein said compound of Formula (I) is a compound of the formula:

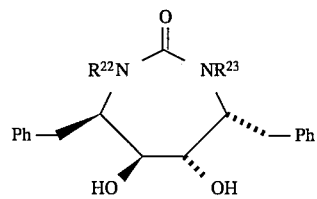

selected from the group consisting of:
the compound wherein R$^{22}$ is allyl and R$^{23}$ is allyl;
the compound wherein R$^{22}$ is propyl and R$^{23}$ is propyl;
the compound wherein R$^{22}$ is cyclopropylmethyl and R$^{23}$ is cyclopropylmethyl;
the compound wherein R$^{22}$ is n-hexyl and R$^{23}$ is n-hexyl;
the compound wherein R$^{22}$ is n-butyl and R$^{23}$ is n-butyl;
the compound wherein R$^{22}$ is CH$_2$CH=C(CH$_3$)$_2$ and R$^{23}$ is CH$_2$CH=C(CH$_3$)$_2$;
the compound wherein R$^{22}$ is CH$_2$CH=C(CH$_3$)$_2$ and R$^{23}$ is H;
the compound wherein R$^{22}$ is i-pentyl and R$^{23}$ is i-pentyl;

the compound wherein $R^{22}$ is 2-methallyl and $R^{23}$ is 2-methallyl;

the compound wherein $R^{22}$ is n-pentyl and $R^{23}$ is n-pentyl;

the compound wherein $R^{22}$ is benzyl and $R^{23}$ is benzyl;

the compound wherein $R^{22}$ is i-hexyl and $R^{23}$ is i-hexyl;

the compound wherein $R^{22}$ is allyl and $R^{23}$ is isoprenyl;

the compound wherein $R^{22}$ is 1-cinnamyl and $R^{23}$ is 1-cinnamyl;

the compound wherein $R^{22}$ is 4-fluorobenzyl and $R^{23}$ is 4-fluorobenzyl;

the compound wherein $R^{22}$ is cyclopropylmethyl and $R^{23}$ is benzyl;

the compound wherein $R^{22}$ is allyl and $R^{23}$ is benzyl;

the compound wherein $R^{22}$ is $CH_2CH=C(CH_3)_2$ and $R^{23}$ is cyclopropylmethyl;

the compound wherein $R^{22}$ is 2-naphthylmethyl and $R^{23}$ is 2-napthylmethyl;

the compound wherein $R^{22}$ is n-butyl and $R^{23}$ is benzyl;

the compound wherein $R^{22}$ is allyl and $R^{23}$ is cyclopropylmethyl;

the compound wherein $R^{22}$ is n-butyl and $R^{23}$ is cyclopropylmethyl;

the compound wherein $R^{22}$ is $CH_2CH=C(CH_3)_2$ and $R^{23}$ is benzyl;

the compound wherein $R^{22}$ is benzyl and $R^{23}$ is ethyl;

the compound wherein $R^{22}$ is benzyl and $R^{23}$ is 4-pyridinylmethyl;

the compound wherein $R^{22}$ is cyclopropylmethyl and $R^{23}$ is 4-pyridinylmethyl;

the compound wherein $R^{22}$ is benzyl and $R^{23}$ is cyclopentylmethyl;

the compound wherein $R^{22}$ is cyclopropylmethyl and $R^{23}$ is cyclopentylmethyl;

the compound whereran $R^{22}$ is benzyl and $R^{23}$ is n-propyl;

the compound wherein $R^{22}$ is cyclopropylmethyl and $R^{23}$ is cinnamyl;

the compound wherein $R^{22}$ is cyclopropylmethyl and $R^{23}$ is 2-naphthylmethyl;

the compound wherein $R^{22}$ is cyclopentylmethyl and $R^{23}$ is 2-naphthylmethyl;

the compound wherein $R^{22}$ is benzyl and $R^{23}$ is 2-naphthylmethyl;

the compound wherein $R^{22}$ is cyclopropylmethyl and $R^{23}$ is 2-pyridinylmethyl;

the compound wherein $R^{22}$ is 3-cyanobenzyl and $R^{23}$ is 3-cyanobenzyl;

the compound wherein $R^{22}$ is allyl and $R^{23}$ is 2-naphthylmethyl;

the compound wherein $R^{22}$ is n-propyl and $R^{23}$ is 2-naphthylmethyl;

the compound wherein $R^{22}$ is n-butyl and $R^{23}$ is 2-naphthylmethyl;

the compound wherein $R^{22}$ is hydrogen and $R^{23}$ is 2-naphthylmethyl;

the compound wherein $R^{22}$ is 4-pyridinylmethyl and $R^{23}$ is 2-naphthylmethyl;

the compound wherein $R^{22}$ is allyl and $R^{23}$ is cyclopentylmethyl;

the compound wherein $R^{22}$ is allyl and $R^{23}$ is 2-quinolinylmethyl;

the compound wherein $R^{22}$ is 3-pyridinylmethyl and $R^{23}$ is cyclopropylmethyl;

the compound wherein $R^{22}$ is 3-pyridinylmethyl and $R^{23}$ is 2-naphthylmethyl;

the compound wherein $R^{22}$ is 3-hydroxybenzyl and $R^{23}$ is 3-hydroxybenzyl;

the compound wherein $R^{22}$ is vinylbenzyl and $R^{23}$ is vinylbenzyl;

the compound wherein $R^{22}$ is 3-allyloxybenzyl and $R^{23}$ is 3-hydroxybenzyl;

the compound wherein $R^{22}$ is 3-pyridinylmethyl and $R^{23}$ is 3-pyridinylmethyl;

the compound wherein $R^{22}$ is 2-naphthylmethyl and $R^{23}$ is 4-fluorobenzyl;

the compound wherein $R^{22}$ is 4-hydroxybenzyl and $R^{23}$ is 4-hydroxybenzyl;

the compound wherein $R^{22}$ is 3-hydroxymethylbenzyl and $R^{23}$ is 3-hydroxymethylbenzyl;

the compound wherein $R^{22}$ is 3-carbomethoxybenzyl and $R^{23}$ is 3-carbomethoxybenzyl;

the compound wherein $R^{22}$ is 4-hydroxymethylbenzyl and $R^{23}$ is 4-hydroxymethylbenzyl;

the compound wherein $R^{22}$ is 3-formylbenzyl and $R^{23}$ is 3-formylbenzyl;

the compound wherein $R^{22}$ is 4-cyanobenzyl and $R^{23}$ is 4-cyanobenzyl;

the compound wherein $R^{22}$ is 4-formylbenzyl and $R^{23}$ is 4-formylbenzyl;

the compound wherein $R^{22}$ is 4-hydroxybenzyl and $R^{23}$ is 2-propyl;

the compound wherein $R^{22}$ is 3-hydroxybenzyl and $R^{23}$ is 2-propyl;

the compound wherein $R^{22}$ is 3-carboxybenzyl and $R^{23}$ is 3-carboxybenzyl;

the compound wherein $R^{22}$ is 3-formaldoximebenzyl and $R^{23}$ is 3-formaldoximebenzyl;

the compound wherein $R^{22}$ is cyclopropylmethyl and $R^{23}$ is 3-hydroxybenzyl;

the compound wherein $R^{22}$ is cyclopropylmethyl and $R^{23}$ is 4-hydroxybenzyl;

the compound wherein $R^{22}$ is cyclobutylmethyl and $R^{23}$ is cyclobutylmethyl;

the compound wherein $R^{22}$ is cyclopentylmethyl and $R^{23}$ is cyclopentylmethyl;

the compound wherein $R^{22}$ is 3n-butyl and $R^{23}$ is $CH_2CH=C(CH_3)_2$;

the compound wherein $R^{22}$ is n-butyl and $R^{23}$ is cyclopentylmethyl;

the compound wherein $R^{22}$ is benzyl and $R^{23}$ is H;

the compound wherein $R^{22}$ is 3-fluorobenzyl and $R^{23}$ is 3-fluorobenzyl;

the compound wherein $R^{22}$ is 3-methoxybenzyl and $R^{23}$ is 3-methoxybenzyl;

the compound wherein $R^{22}$ is 3,4-difluorobenzyl and $R^{23}$ is 3,4-difluorobenzyl;

the compound wherein $R^{22}$ is 4-methylbenzyl and $R^{23}$ is 4-methylbenzyl;

the compound wherein $R^{22}$ is 4-chlorobenzyl and $R^{23}$ is 4-chlorobenzyl;

the compound wherein $R^{22}$ is cyclopropylmethyl and $R^{23}$ is 4-fluorobenzyl;

the compound wherein $R^{22}$ is 3-chlorobenzyl and $R^{23}$ is 3-chlorobenzyl;

the compound wherein $R^{22}$ is 3-nitrobenzyl and $R^{23}$ is 3-nitrobenzyl;

the compound wherein $R^{22}$ is 3-methylbenzyl and $R^{23}$ is 3-methylbenzyl;

the compound wherein $R^{22}$ is 3-bromobenzyl and $R^{23}$ is 3-bromobenzyl;

the compound wherein $R^{22}$ is 4-fluorobenzyl and $R^{23}$ is H;

the compound wherein $R^{22}$ is cyclopropylmethyl and $R^{23}$ is 3-chlorobenzyl;

the compound wherein $R^{22}$ is 3-aminobenzyl and $R^{23}$ is 3-aminobenzyl;

the compound wherein $R^{22}$ is 4-aminobenzyl and $R^{23}$ is 4-aminobenzyl;

the compound wherein $R^{22}$ is 3-nitrobenzyl and $R^{23}$ is H;

the compound wherein $R^{22}$ is 3-(NHCHO)benzyl and $R^{23}$ is 3-(NHCHO)benzyl;

the compound wherein $R^{22}$ is 3-(NHCOCH$_3$)benzyl and $R^{23}$ is 3-(NHCOCH$_3$)benzyl;

the compound wherein $R^{22}$ is 3,4-dihydroxybenzyl and $R^{23}$ is 3,4-dihydroxybenzyl;

the compound wherein $R^{22}$ is 3-formaldoximebenzyl and $R^{23}$ is 3-(N-hydroxy)aminomethylbenzyl;

the compound wherein $R^{22}$ is 3-(N-hydroxy)aminomethylbenzyl and $R^{23}$ is 3-(N-hydroxy)aminomethylbenzyl;

the compound wherein $R^{22}$ is 3-(CH$_3$OC(=O)O—)benzyl and $R^{23}$ is 3-(CH$_3$OC(=O)O—)benzyl;

the compound wherein $R^{22}$ is 3-(1-hydroxyethyl)benzyl and $R^{23}$ is 3-(1-hydroxyethyl)benzyl;

the compound wherein $R^{22}$ is 3-(HOCH$_2$CH$_2$N=CH)benzyl and $R^{23}$ is 3-(HOCH$_2$CH$_2$N=CH)benzyl;

the compound wherein $R^{22}$ is 3-(HOCH$_2$CH$_2$N=CH)benzyl and $R^{23}$ is 3-(2-oxazolidinyl)benzyl;

the compound wherein $R^{22}$ is 3-(C$_6$H$_5$CH$_2$NHC(=O)O)benzyl and $R^{23}$ is 3-(C$_6$HSCH$_2$NHC(=O)O) benzyl;

the compound wherein $R^{22}$ is 3-(CH$_3$NHC(=O)O)benzyl and $R^{23}$ is 3-(CH$_3$NHC(=O)O)benzyl;

the compound wherein $R^{22}$ is 3-(HOCH$_2$CC)benzyl and $R^{23}$ is 3-bromobenzyl;

the compound wherein $R^{22}$ is 3-acetylbenzyl and $R^{23}$ is 3-bromobenzyl;

the compound wherein $R^{22}$ is 3-acetylbenzyl and $R^{23}$ is 3-acetylbenzyl;

the compound wherein $R^{22}$ is 3-(CH$_3$C(=NOH))benzyl and $R^{23}$ is 3-(CH$_3$C(=NOH))benzyl;

the compound wherein $R^{22}$ is 3-(1-hydroxyethyl)benzyl and $R^{23}$ is 3-bromobenzyl;

the compound wherein $R^{22}$ is 3-(chloromethyl)benzyl and $R^{23}$ is 3-(chloromethyl)benzyl;

the compound wherein $R^{22}$ is 3-(5-tetrazolyl)benzyl and $R^{23}$ is cyclopropylmethyl;

the compound wherein $R^{22}$ is 3-cyanobenzyl and $R^{23}$ is 3-formylbenzyl;

the compound wherein $R^{22}$ is 4-acetoxybenzyl and $R^{23}$ is 4-hydroxybenzyl;

the compound wherein $R^{22}$ is 3-aminocarbonylbenzyl and $R^{23}$ is 3-aminocarbonylbenzyl;

the compound wherein $R^{22}$ is 3-(H$_2$NCOCH$_2$O)benzyl and $R^{23}$ is 3-(H$_2$NCOCH$_2$O)benzyl;

the compound wherein $R^{22}$ is 3-hydroxybenzyl and $R^{23}$ is H;

the compound wherein $R^{22}$ is 3-methylbenzyl and $R^{23}$ is 3-hydroxybenzyl;

the compound wherein $R^{22}$ is 2-naphthylmethyl and $R^{23}$ is 3-hydroxybenzyl;

the compound wherein $R^{22}$ is 3-(H$_2$NNHC(=O))-benzyl and $R^{23}$ is 3-(H$_2$NNHC(=O))-benzyl;

the compound wherein $R^{22}$ is 4-(H$_2$NNHC(=O))-benzyl and $R^{23}$ is 4-(H$_2$NNHC(=O))-benzyl;

the compound wherein $R^{22}$ is 4-hydroxymethylbenzyl and $R^{23}$ is 3-hydroxybenzyl;

the compound wherein $R^{22}$ is 3-(H$_2$NC(=O)NHN=CH)-benzyl and $R^{23}$ is 3-(H$_2$NC(=O)NHN=CH)-benzyl;

the compound wherein $R^{22}$ is 3-[(N-methoxy)aminocarbonyl]-benzyl and $R^{23}$ is 3-[(N-methoxy)aminocarbonyl]-benzyl;

the compound wherein $R^{22}$ is 4-[(N-methoxy)aminocarbonyl]-benzyl and $R^{23}$ is 4-[(N-methoxy)aminocarbonyl]-benzyl;

the compound wherein $R^{22}$ is 3-(HOCH$_2$CH(OH)CH$_2$O)benzyl and $R^{23}$ is 3-(HOCH$_2$CH(OH)CH$_2$O)benzyl;

the compound wherein $R^{22}$ is 3-(2-hydroxyethoxy)benzyl and $R^{23}$ is 3-(2-hydroxyethoxy)benzyl;

the compound wherein $R^{22}$ is 3-(1,2-dihydroxyethyl)benzyl and $R^{23}$ is 4-(1,2-dihydroxyethyl)benzyl;

the compound wherein $R^{22}$ is 3-aminocarbonylbenzyl and $R^{23}$ is 3-(H$_2$NC(=NH))benzyl;

the compound wherein $R^{22}$ is 4-hydroxybenzyl and $R^{23}$ is 3-formyl-4-hydroxybenzyl;

the compound wherein $R^{22}$ is 3-carbomethoxybenzyl and $R^{23}$ is 3-(N-methylaminocarbonyl)benzyl;

the compound wherein $R^{22}$ is 3-(N-methylaminocarbonyl)benzyl and $R^{23}$ is 3-(N-methylaminocarbonyl)benzyl;

the compound wherein $R^{22}$ is benzyl and $R^{23}$ is 3-hydroxybenzyl;

the compound wherein $R^{22}$ is 2-naphthylmethyl and $R^{23}$ is 4-hydroxymethylbenzyl;

the compound wherein $R^{22}$ is 3-( 1,2-dihydroxyethyl)benzyl and $R^{23}$ is 3-( 1,2-dihydroxyethyl)benzyl;

the compound wherein $R^{22}$ is 4-(1,2-dihydroxyethyl)benzyl and $R^{23}$ is 4-(1,2-dihydroxyethyl)benzyl;

the compound wherein $R^{22}$ is 3-hydroxymethylbenzyl and $R^{23}$ is 3-(N-methylaminocarbonyl)benzyl;

the compound wherein $R^{22}$ is 4-hydroxymethylbenzyl and $R^{23}$ is hydrogen;

the compound wherein $R^{22}$ is 3-(boronic acid)benzyl and $R^{23}$ is 3-(boronic acid)benzyl;

the compound wherein $R^{22}$ is 3-nitrobenzyl and $R^{23}$ is 3-benzyloxybenzyl;

the compound wherein $R^{22}$ is 3-aminobenzyl and $R^{23}$ is 3-hydroxybenzyl;

the compound wherein $R^{22}$ is 3-(N-ethylaminocarbonyl)benzyl and $R^{23}$ is 3-(N-ethylaminocarbonyl)benzyl;

the compound wherein $R^{22}$ is 3-carbomethoxybenzyl and $R^{23}$ is 3-(N,N-diethylaminocarbonyl)benzyl;

the compound wherein $R^{22}$ is 3-carbomethoxybenzyl and $R^{23}$ is 3-(N-ethylaminocarbonyl)benzyl;

the compound wherein $R^{22}$ is 6-hydroxy1-hexyl and $R^{23}$ is hydrogen;

the compound wherein $R^{22}$ is 6-hydroxy1-hexyl and $R^{23}$ is 6-hydroxy-1-hexyl;

the compound wherein $R^{22}$ is cyclopropylmethyl and $R^{23}$ is 6-hydroxy-1-hexyl;

the compound wherein $R^{22}$ is 5-carboxy-1-pentyl and $R^{23}$ is 5-carboxy-1-pentyl;

the compound wherein $R^{22}$ is 3-iodobenzyl and $R^{23}$ is 3-iodobenzyl;

the compound wherein $R^{22}$ is benzyl and $R^{23}$ is 2-(hydroxymethyl)-cyclopropylmethyl;

the compound wherein $R^{22}$ is 3-(thiomethyl)benzyl and $R^{23}$ is 3-(thiomethyl)benzyl;

the compound wherein $R^{22}$ is 3-(methylsulfonyl)benzyl and $R^{23}$ is 3-(methylsulfonyl)benzyl;

the compound wherein $R^{22}$ is 6-hexenyl and $R^{23}$ is 6-hexenyl;

the compound wherein $R^{22}$ is 6-bromo-5-hydroxy-1-hexyl and $R^{23}$ is 6-bromo-5-hydroxy-1-hexyl;

the compound wherein $R^{22}$ is 5-hydroxy-1-pentyl and $R^{23}$ is 5-hydroxy-1-pentyl;

the compound wherein $R^{22}$ is 3-aminobenzyl and $R^{23}$ is 4-hydroxymethylbenzyl;

the compound wherein $R^{22}$ is 3-($H_2NC(=O)NH$)benzyl and $R^{23}$ is 3-($H_2NC(=O)NH$)benzyl;

the compound wherein $R^{22}$ is 3-(N-methylamino)benzyl and $R^{23}$ is 3-(N-methylamino)benzyl;

the compound wherein $R^{22}$ is cyclopropylmethyl and $R^{23}$ is 3-aminobenzyl;

the compound wherein $R^{22}$ is cyclopropylmethyl and $R^{23}$ is 3-nitrobenzyl;

the compound wherein $R^{22}$ is 3-(N,N-dimethylamino)benzyl and $R^{23}$ is 3-(N,N-dimethylamino)benzyl;

the compound wherein $R^{22}$ is 3-nitrobenzyl and $R^{23}$ is 4-hydroxymethylbenzyl;

the compound wherein $R^{22}$ is 3-aminobenzyl and $R^{23}$ is 3-($CH_3NHC(=O)NH$)benzyl;

the compound wherein $R^{22}$ is 3-($CH_3NHC(=O)NH$)benzyl and $R^{23}$ is 3-($CH_3NHC(=O)NH$)benzyl;

the compound wherein $R^{22}$ is 3-(N-methylamino)benzyl and $R^{23}$ is 4-hydroxymethylbenzyl;

the compound wherein $R^{22}$ is 3-((N,N-dimethylaminoglycyl)amino)benzyl and $R^{23}$ is 3-((N,N-dimethylaminoglycyl)amino)benzyl;

the compound wherein $R^{22}$ is 3-((N-methylaminoglycyl)amino)benzyl and $R^{23}$ is 3-((N-methylaminoglycyl)amino)benzyl;

the compound wherein $R^{22}$ is 3-((N,N-dimethylaminoglycyl)amino)benzyl and $R^{23}$ is 4-hydroxymethylbenzyl;

the compound wherein $R^{22}$ is 3-((N-phenylmethoxycarbonylaminoglycyl)amino)benzyl and $R^{23}$ is 3-((N-phenylmethoxycarbonylaminoglycyl)amino)benzyl;

the compound wherein $R^{22}$ is 3-(glycylamino)benzyl and $R^{23}$ is 3-(glycylamino)benzyl;

the compound wherein $R^{22}$ is 3-(glycylamino)benzyl and $R^{23}$ is 4-hydroxymethylbenzyl;

the compound wherein $R^{22}$ is 3-((N-phenylmethoxycarbonylamino-L-alanyl)amino)benzyl and $R^{23}$ is 3-((N-phenylmethoxycarbonylamino-L-alanyl)amino)benzyl;

the compound wherein $R^{22}$ is 3-((N-phenylmethoxycarbonylamino-L-phenylalanyl)amino)benzyl and $R^{23}$ is 3-((N-phenylmethoxycarbonylamino-L-phenylalanyl)amino)benzyl;

the compound wherein $R^{22}$ is 3-(L-alanyl)amino)benzyl and $R^{23}$ is 3-(L-alanyl)amino)benzyl;

the compound wherein $R^{22}$ is 3-(L-phenylalanyl)amino)benzyl and $R^{23}$ is 3-(L-phenylalanyl)amino)benzyl;

the compound wherein $R^{22}$ is 5-hydroxy-1-pentyl and $R^{23}$ is hydrogen;

the compound wherein $R^{22}$ is 5-hydroxy-1-pentyl and $R^{23}$ is 2-naphthylmethyl;

the compound wherein $R^{22}$ is 5-hydroxy-1-pentyl and $R^{23}$ is benzyl;

the compound wherein $R^{22}$ is 5-hydroxy-1-pentyl and $R^{23}$ is 4-hydroxymethylbenzyl;

the compound wherein $R^{22}$ is 6-hydroxy-1-hexyl and $R^{23}$ is 2-naphthylmethyl;

the compound wherein $R^{22}$ is 5-hydroxy-1-pentyl and $R^{23}$ is 3-hydroxybenzyl;

the compound wherein $R^{22}$ is 5-hydroxy-1-pentyl and $R^{23}$ is (5-methylsulfonyl)-1-pentyl;

the compound wherein $R^{22}$ is 5-hydroxy-1-pentyl and $R^{23}$ is 5-($CH_3S(O)$)-1-pentyl;

the compound wherein $R^{22}$ is 5-hydroxy-1-pentyl and $R^{23}$ is cyclopropylmethyl;

the compound wherein $R^{22}$ is 5-hydroxy-1-pentyl and $R^{23}$ is 5-methoxy-1-pentyl;

the compound wherein $R^{22}$ is 5-hydroxy-1-pentyl and $R^{23}$ is 3-cyanobenzyl;

the compound wherein $R^{22}$ is 5-hydroxy-1-pentyl and $R^{23}$ is 3-carboethoxybenzyl;

the compound wherein $R^{22}$ is 4-hydroxy-1-hexyl and $R^{23}$ is 4-hydroxy-1-hexyl;

the compound wherein $R^{22}$ is 4-hydroxy-1-hexyl and $R^{23}$ is 2-naphthylmethyl;

the compound wherein $R^{22}$ is 4-oxime-1-hexyl and $R^{23}$ is 4-oxime-1-hexyl;

the compound wherein $R^{22}$ is 5-hydroxy-1-pentyl and $R^{23}$ is 3-hydroxymethylbenzyl;

the compound wherein $R^{22}$ is 6-amino-1-hexyl and $R^{23}$ is 4-hydroxymethylbenzyl;

the compound wherein $R^{22}$ is 3-(N,N-diethylaminocarbonyl)benzyl and $R^{23}$ is 3-(N,N-diethylaminocarbonyl)benzyl;

the compound wherein $R^{22}$ is 3-carbomethoxybenzyl and $R^{23}$ is 3-(N,N-diethylaminocarbonyl)benzyl;

the compound wherein $R^{22}$ is 3-carbomethoxybenzyl and $R^{23}$ is 3-(N-ethylaminocarbonyl)benzyl;

the compound wherein $R^{22}$ is 3-hydroxymethylbenzyl and $R^{23}$ is hydrogen;

the compound wherein $R^{22}$ is 3-hydroxymethylbenzyl and $R^{23}$ is 3-(N,N-diethylaminocarbonyl)benzyl;

the compound wherein $R^{22}$ is 3-hydroxymethylbenzyl and $R^{23}$ is 3-(N-ethylaminocarbonyl)benzyl;

the compound wherein $R^{22}$ is 3-(N-propylaminocarbonyl)benzyl and $R^{23}$ is 3-(N-propylaminocarbonyl)benzyl;

the compound wherein $R^{22}$ is 3-($HO_2C$)benzyl and $R^{23}$ is 3-(N-isopropylaminocarbonyl)benzyl;

the compound wherein $R^{22}$ is 3-($HO_2C$)benzyl and $R^{23}$ is 3-(N-propylaminocarbonyl)benzyl;

the compound wherein $R^{22}$ is 3-($HO_2C$)benzyl and $R^{23}$ is benzyl;

the compound wherein $R^{22}$ is 3-($HO_2C$)benzyl and $R^{23}$ is cyclopropylmethyl;

the compound wherein $R^{22}$ is 4-hydroxymethylbenzyl and $R^{23}$ is 3-($HO_2C$)benzyl;

the compound wherein $R^{22}$ is 3-hydroxymethylbenzyl and $R^{23}$ is 3-pyridinylmethyl;

the compound wherein $R^{22}$ is 4-hydroxymethylbenzyl and $R^{23}$ is 3-aminocarbonylbenzyl;

the compound wherein $R^{22}$ is 3-aminobenzyl and $R^{23}$ is 2-naphthylmethyl;

the compound wherein $R^{22}$ is cyclopropylmethyl and $R^{23}$ is 3-aminocarbonylbenzyl;

the compound wherein $R^{22}$ is 3-aminocarbonylbenzyl and $R^{23}$ is hydrogen;

the compound wherein $R^{22}$ is 3-hydroxymethylbenzyl and $R^{23}$ is 3-(N-ethylaminocarbonyl)benzyl;

the compound wherein $R^{22}$ is 3-hydroxymethylbenzyl and $R^{23}$ is 3-(N-methylamino)benzyl;

the compound wherein $R^{22}$ is 3-(N-methylamino)benzyl and $R^{23}$ is 2-naphthylmethyl;

the compound wherein $R^{22}$ is 4-formylbenzyl and $R^{23}$ is 4-hydroxymethylbenzyl;

the compound wherein $R^{22}$ is 3-(1-hydroxy- 1-ethyl)benzyl and $R^{23}$ is 3-(1-hydroxyethyl)benzyl;

the compound wherein $R^{22}$ is 3-pyridinylmethyl and $R^{23}$ is 4-hydroxymethylbenzyl;

the compound wherein $R^{22}$ is 3-(N-imidazolylmethyl)benzyl and $R^{23}$ is 3-(N-imidazolylmethyl)benzyl;

the compound wherein $R^{22}$ is 3-(2,2-dimethyl- 1-propionyl)benzyl and $R^{23}$ is 3-( 2,2-dimethyl-1-propionyl)benzyl;

the compound wherein $R^{22}$ is 3-(2,2,2-trifluoro-1-hydroxyethyl)benzyl and $R^{23}$ is 3-( 2,2,2-trifluoro-1-hydroxyethyl)benzyl;

the compound wherein $R^{22}$ is 3-(2-imidazolyl-C(=O))benzyl and $R^{23}$ is 3-(2-imidazolyl-C(=O))benzyl;

the compound wherein $R^{22}$ is 3-(3-hydroxy- 1-propyn-1-yl)benzyl and $R^{23}$ is 3-( 3-hydroxy-1-propyn-1-yl)benzyl;

the compound wherein $R^{22}$ is 3-(2,2,2-trifluoroacetyl)benzyl and $R^{23}$ is 3-(2,2,2-trifluoroacetyl)benzyl;

the compound wherein $R^{22}$ is 3-propionylbenzyl and $R^{23}$ is 3-propionylbenzyl;

the compound wherein $R^{22}$ is 3-(4-pyrazolyl)benzyl and $R^{23}$ is 3-(4-pyrazolyl)benzyl;

the compound wherein $R^{22}$ is 3-($CH_3CH_2C$(=N-OH))benzyl and $R^{23}$ is 3-($CH_3CH_2C$(=N—OH))benzyl;

the compound wherein $R^{22}$ is 3-sulfonamidobenzyl and $R^{23}$ is 3-sulfonamidobenzyl;

the compound wherein $R^{22}$ is 3-($CF_3CH_2C$(=N-OH))benzyl and $R^{23}$ is 3-($CF_3CH_2C$(=N-OH))benzyl;

the compound wherein $R^{22}$ is 4-fluoromethylbenzyl and $R^{23}$ is 4-fluoromethylbenzyl;

the compound wherein $R^{22}$ is 4-(1-hydroxyethyl)benzyl and $R^{23}$ is 4-(1-hydroxyethyl)benzyl; and the compound wherein $R^{22}$ is 3-(5-methyl- 1,2,3-oxadiazolyl)benzyl and $R^{23}$ is 3-(5-methyl- 1,2,3-oxadiazolyl)-benzyl;

the compound wherein $R^{22}$ is 3-($H_2NC$(=NOH)benzyl and $R^{23}$ is 3-($H_2NC$(=NOH)benzyl;

the compound wherein $R^{22}$ is 3-($H_2NC$(=NOH)- 4-fluorobenzyl and $R^{23}$ is 3-($H_2NC$(=NOH)- 4-fluorobenzyl;

the compound wherein $R^{22}$ is 5-benzotriazolylmethyl and $R^{23}$ is 5-benzotriazolylmethyl;

the compound wherein $R^{22}$ is 5-benzimidazolylmethyl and $R^{23}$ is 5-benzimidazolylmethyl;

the compound wherein $R^{22}$ is 5-benzimidazolylmethyl and $R^{23}$ is 5-benzimidazolylmethyl;

the compound wherein $R^{22}$ is 5-benzotriazolylmethyl and $R^{23}$ is 4-hydroxymethylbenzyl;

the compound wherein $R^{22}$ is 5-benzotriazolylmethyl and $R^{23}$ is 3-(3-pyrazolyl)benzyl;

the compound wherein $R^{22}$ is 5-indazolylmethyl and $R^{23}$ is 5-indazolylmethyl;

the compound wherein $R^{22}$ is 3-chloro- 5-indazolylmethyl and $R^{23}$ is 3-chloro-5-indazolylmethyl;

the compound wherein $R^{22}$ is 3-methylamino- 5-indazolylmethyl and $R^{23}$ is 3-methylamino- 5-indazolylmethyl;

the compound wherein $R^{22}$ is 3-ethylamino- 5-indazolylmethyl and $R^{23}$ is 3-ethylamino-5-indazolylmethyl;

the compound wherein $R^{22}$ is 6-indazolylmethyl and $R^{23}$ is 6-indazolylmethyl;

the compound wherein $R^{22}$ is 3-amino- 5-benzisoxazolylmethyl and $R^{23}$ is 3-amino- 5-benzisoxazolylmethyl. the compound wherein $R^4$ is 4-aminobenzyl, $R^7$ is 2-aminobenzyl, $R^{22}$ and $R^{23}$ are cyclopropylmethyl; the compound wherein $R^4$ and $R^7$ are 4-fluorobenzyl, $R^{22}$ and $R^{23}$ are 3-hydroxybenzyl; the compound wherein $R^4$ and $R^7$ are 4-fluorobenzyl, $R^{22}$ and $R^{23}$ are cyclopropylmethyl; the compound wherein $R^4$ and $R^7$ are 4-fluorobenzyl, $R^{22}$ and $R^{23}$ are 4-hydroxymethylbenzyl; the compound wherein $R^4$ and $R^7$ are 4-fluorobenzyl, $R^{22}$ and $R^{23}$ are 3-aminocarbonylbenzyl; the compound wherein $R^4$ and $R^7$ are 4-fluorobenzyl, $R^{22}$ and $R^{23}$ are 3-acetylbenzyl; the compound wherein $R^4$ and $R^7$ are 4-fluorobenzyl, $R^{22}$ and $R^{23}$ are 3-butyrylbenzyl; the compound wherein $R^4$ and $R^7$ are 4-fluorobenzyl, $R^{22}$ and $R^{23}$ are 3-hydroxymethylbenzyl; the compound wherein $R^4$ and $R^7$ are 4-fluorobenzyl, $R^{22}$ and $R^{23}$ are 3- ($CH_3C$ (=N-OH)benzyl; and the compound wherein $R^4$ and $R^7$ are 3-methoxybenzyl, $R^{22}$ and $R^{23}$ are benzyl. the compound wherein $R^4$ and $R^7$ are 4-fluorobenzyl, $R^{22}$ and $R^{23}$ are 3- ($H_2NC$(=NOH) benzyl; the compound wherein $R^4$ and $R^7$ are 4-fluorobenzyl, $R^{22}$ and $R^{23}$ are 3- ($H_2NC$(=NOH) -4-fluorobenzyl; the compound wherein $R^4$ and $R^7$ are 3-methoxybenzyl, $R^{22}$ and $R^{23}$ are cyclopropylmethyl; the compound wherein $R^4$ and $R^7$ are 3-methoxybenzyl, $R^{22}$ and $R^{23}$ are 4-hydroxymethylbenzyl; the compound wherein $R^4$ and $R^7$ are 3-methoxybenzyl, $R^{22}$ and $R^{23}$ are 3-methoxybenzyl; the compound wherein $R^4$ and $R^7$ are 3-hydroxybenzyl, $R^{22}$ and $R^{23}$ are 3-hydroxybenzyl.. the compound wherein $R^4$ and $R^7$ are 4-methoxybenzyl, $R^{22}$ and $R^{23}$ are cyclopropylmethyl; the compound wherein $R^4$ and $R^7$ are 4-methoxybenzyl, $R^{22}$ and $R^{23}$ are benzyl; the compound wherein $R^4$ and $R^7$ are 4-methoxybenzyl, $R^{22}$ and $R^{23}$ are 2-naphthylmethyl; the compound wherein $R^4$ and $R^7$ are 4-methoxybenzyl, $R^{22}$ and $R^{23}$ are 4-hydroxymethylbenzyl; the compound wherein $R^4$ and $R^7$ are 4-hydroxybenzyl, $R^{22}$ and $R^{23}$ are benzyl; the compound wherein $R^4$ and $R^7$ are 4-methoxybenzyl, $R^{22}$ and $R^{23}$ are allyl; the compound wherein $R^4$ and R[7] are 4-(2- hydroxyethoxy)benzyl, R[22] and R[23] are benzyl; the compound wherein R[4] and R[7] are 4-(2-morpholinylethoxy)benzyl, R[22] and R[23] are benzyl; the compound wherein R[4] and R[7] are 3- (H$_2$NC(=O)CH2O) benzyl, R[22] and R[23] are n-butyl; the compound wherein R[4] and R[7] are 3,4- difluorobenzyl, R[22] and R[23] are 3-hydroxymethylbenzyl; the compound wherein R[4] and R[7] are 3,4- difluorobenzyl, R[22] and R[23] are 4-hydroxymethylbenzyl; the compound wherein R[4] and R[7] are 3,4- difluorobenzyl, R[22] and R[23] are 3-(H$_2$NC(=O))benzyl; the compound wherein R[4] and R[7] are 3,4- difluorobenzyl, R[22] and R[23] are 3-(H$_2$NC(=NOH))benzyl; the compound wherein R[4] and R[7] are 2- naphthylmethyl, R[22] and R[23] are benzyl; the compound wherein R[4] and R[7] are 2- naphthylmethyl, R[22] and R[23] are cyclopropylmethyl; the compound wherein R[4] and R[7]

are 2-thienylmethyl, R[22] and R[23] are cyclopropylmethyl; the compound wherein R[4] and R[7] are 2-thienylmethyl, R[22] and R[23] are 3- (H$_2$NC(=NOH))benzyl; the compound wherein R[4] and R[7] are 4- methylthiobenzyl, R[22] and R[23] are benzyl; the compound wherein R[4] and R[7]

are isopropyl, R[22] and R[23] are n-hexyl

34. A composition of claim 1 wherein said compound of Formula (I) is a compound of the formula:

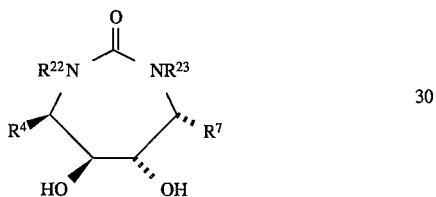

or a pharmaceutically acceptable salt or prodrug form thereof wherein:

R[4] and R[7] are independently selected from: benzyl, fluorobenzyl, pyrrolylmethyl, methoxybenzyl, isobutyl, nitrobenzyl aminobenzyl, hydroxybenzyl, or thienylmethyl; and R[22] and R[23] are independently selected from:

hydrogen, allyl, methyl, ethyl, propyl, cyclopropylmethyl, n-butyl, i-butyl, CH$_2$CH=C(CH$_3$)$_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, (H$_2$NC(=O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl)ethylbenzyl, (CH$_3$C(=NOH))-benzyl, (H$_2$NNHC(=O))-benzyl, (H$_2$NC(=O)NHN=CH)-benzyl, (CH$_{30}$NHC(=O))-benzyl, (HONHC(=O))-benzyl, (CH$_3$NHC(=O))-benzyl, N,N-dimethylaminocarbonylbenzyl, (HOCH$_2$CH (OH)CH$_2$O)-benzyl, hydroxyethoxybenzyl (oxazolidinyl)-benzyl, (hydroxyl)hexyl, hexenyl, (hydroxy)octyl, (hydroxyl)pentyl, (carboxy)pentyl, (carbomethoxy)-pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)-benzyl, (H$_2$NSO$_2$)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl)benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperaz in-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C-C(=O))benzyl, (N-methyl-N-ethylaminoethyl)aminocarbonylbenzyl, (pyrrolidinylethyl)aminocarbonylbenzyl, or (piperidinylethyl)aminocarbonylbenzyl, (H$_2$NC(=NOH))benzyl, (H$_2$NC(=NOH))fluorobenzyl, benzimidazolylmethyl, benzotriazolylmethyl, indazolylmethyl, benzoxazolinylmethyl, benzisoxazolylmethyl, thienylmethyl, furylmethyl.

35. A composition of claim 1 wherein said compound of Formula (I) is a compound of the formula:

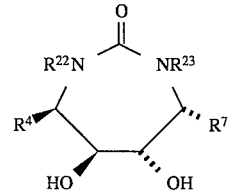

selected from the group consisting of:

the compound wherein R[4] and R[7] are isobutyl, R[22] and R[23] are cyclopropylmethyl;

the compound wherein R[4] and R[7] are isobutyl, R[22] and R[23] are allyl;

the compound wherein R[4] is 4-nitrobenzyl, R[7] is 2-nitrobenzyl, R[22] and R[23] are cyclopropylmethyl;

the compound wherein R⁴ and R⁷ are 4-nitrobenzyl, R²² and R²³ are cyclopropylmethyl;

the compound wherein R⁴ is 4-nitrobenzyl, R⁷ is 2-nitrobenzyl, R²² and R²³ are n-butyl;

the compound wherein R⁴ is 4-aminobenzyl, R⁷ is 2-aminobenzyl, R²² and R²³ are cyclopropylmethyl;

the compound wherein R⁴ and R⁷ are 4-fluorobenzyl, R²² and R²³ are 3-hydroxybenzyl;

the compound wheren R⁴ and R⁷ are 4-fluorobenzyl, R²² and R²³ are cyclopropylmethyl;

the compound wherein R⁴ and R⁷ are 4-fluorobenzyl, R²² and R²³ are 4-hydroxymethylbenzyl;

the compound wherein R⁴ and R⁷ are 4-fluorobenzyl, R²² and R²³ are 3-aminocarbonylbenzyl;

The compound wheien R⁴ and R⁷ are 4-fluorobenzyl, R²² and R²³ are 3-acetylbenzyl;

the compound wherein R⁴ and R⁷ are 4-fluorobenzyl, R²² and R²³ are 3-butyrylbenzyl;

the compound wherein R⁴ and R⁷ are 4-fluorobenzyl, R²² and R²³ are 3-hydroxymethylbenzyl;

the compound wherein R⁴ and R⁷ are 4-fluorobenzyl, R²² and R²³ are 3-(CH₃C(=N-OH)benzyl; and the compound wherein R⁴ and R⁷ are 3-methoxybenzyl, R²² and R²³ are benzyl;

the compound wherein R⁴ and R⁷ are 4-fluorobenzyl, R²² and R²³ are 3-(H₂NC(=NOH)benzyl;

the compound wherein R⁴ and R⁷ are 4-fluorobenzyl, R²² and R²³ are 3-(H₂NC(=NOH)-4-fluorobenzyl;

the compound wherein R⁴ and R⁷ are 3-methoxybenzyl, R²² and R²³ are cyclopropylmethyl;

the compound wherein R⁴ and R⁷ are 3-methoxybenzyl, R²² and R²³ are 4-hydroxymethylbenzyl;

the compound wherein R⁴ and R⁷ are 3-methoxybenzyl, R²² and R²³ are 3-methoxybenzyl;

the compound wherein R⁴ and R⁷ are 3-hydroxybenzyl, R²² and R²³ are 3-hydroxybenzyl;

the compound wherein R⁴ and R⁷ are 3-hydroxybenzyl, R²² and R²³ are cyclorpropylmethy;

the compound wherein R⁴ and R⁷ are 4-methoxybenzyl, R²² and R²³ are benzyl;

the compound wherein R⁴ and R⁷ are 4-methoxybenzyl, R²² and R²³ are 2-naphthylmethyl;

the compound wherein R⁴ and R⁷ are 4-methoxybenzyl, R²² and R²³ are 4-hydroxymethylbenzyl;

the compound wherein R⁴ and R⁷ are 4-hydroxybenzyl, R²² and R²³ are benzyl;

the compound wherein R⁴ and R⁷ are 4-methoxybenzyl, R²² and R²³ are allyl;

the compound wherein R⁴ and R⁷ are 4-(2-hydroxyethoxy) benzyl, R²² and R²³ are benzyl;

the compound wherein R⁴ and R⁷ are 4-(2-morpholinylethoxy)benzyl, R²² and R²³ are benzyl;

the compound wherein R⁴ and R⁷ are 3-(H₂NC(=O)CH₂O)benzyl, R²² and R²³ are n-butyl;

the compound wherein R⁴ and R⁷ are 3,4-difluorobenzyl, R²² and R²³ are 3-hydroxymethylbenzyl;

the compound wherein R⁴ and R⁷ are 3,4-difluorobenzyl, R²² and R²³ are 3-(H₂NC(=O))benzyl;

the compound wherein R⁴ and R⁷ are 2-naphthylmethyl, R²² and R²³ are benzyl;

the compound wherein R⁴ and R⁷ are 2-naphthylmethyl, R²² and R²³ are cyclopropylmethyl;

the compouhd wherein R⁴ and R⁷ are 2-thienylmethyl, R²² and R²³ are cyclopropylmethyl;

the compound wherein R⁴ and R⁷ are 4-methylthiobenzyl, R²² and R²³ are benzyl;

the compound wherein R⁴ and R⁷ are isopropyl, R²² and R²³ are n-hexyl.

36. A composition of claim 1 wherein said compound of Formula (I)is [4R-(4α, 5α, 6β, 7β)]-hexahydro- 5,6-bis(hydroxy)-1,3-bis([(4-hydroxymethyl)phenyl]methyl)-4,7-bis(phenylmethyl)-2H-1,3-diazepin-2-one.

37. A composition of claim 1 wherein said compound of Formula (I) is [4R-(4α, 5α, 6β, 7β)]-hexahydro- 5,6-bis(hydroxy)-1,3-bis([(4-hydroxymethyl)phenyl]methyl)- 4,7-bis(phenylmethyl)-2H-1,3-diazepin-2-one and said vehicle comprises a mixture of fatty acid esters of glycerol and fatty acid esters of polyethylene glycol having the characteristics set forth in Table A.

38. A pharmaceutical kit comprising:

(a) a therapeutically effective amount of compound of the Formula (I):

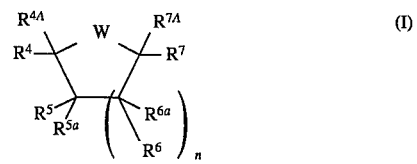

or a pharmaceutically acceptable salt or prodrug form thereof, wherein:

R⁴ and R⁷ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or 0–3 $R^{12}$;
a 5- to 10-membered heterocyclic ring system containing 1 to 4 heteroatoms independently selected from oxygen, nitrogen or sulfur, said heterocyclic ring system being substituted with 0–2 $R^{12}$; or
—OR¹³; —SR¹³; CO₂R¹³;

R⁴ᴬ and R⁷ᴬ are independently selected from the following groups:
hydrogen;
$C_1$–$C_4$ alkyl substituted with 0–6 halogen or 0–3 $C_1$–$C_2$ alkoxy;
benzyl substituted with 0–6 halogen or 0–3 $C_1$–$C_2$ alkoxy; or —OR¹³; —SR¹³; CO₂R¹³;

R⁴ and R⁴ᴬ can alternatively join to form a 5–7 membered carbocyclic ring substituted with 0–2 R¹²;

R⁷ and R⁷ᴬ can alternatively join to form a 5–7 membered carbocyclic ring substituted with 0–2 R¹²;

n is 0;

R⁵ is selected from H; halogen; $C_1$–$C_6$ alkyl substituted with 0–3 R¹¹; —N($^{R20}$)₂; —SR²⁰; or —OR²⁰, —N₃;

R⁶ is independently selected from: hydrogen, halogen, $C_1$–$C_6$ alkyl substituted with 0–3 R¹¹, —N(R²⁰)₂, —SR²⁰, or —OR²¹, —N₃;

R⁵ and R⁶ can alternatively join to form an epoxide or aziridine ring; —OCH₂SCH₂O—; —OS(=O)O—; —OC(=O)O—; —OCH₂O—; —OC(=S)O—; —OC(=O)C(=O)O—; —OC(CH₃)₂O—; —OC((CH₂)₃NH₂)(CH₃)O—;

—OC(OCH$_3$)(CH$_2$CH$_2$CH$_3$)O—; —OS(=O)O—; —NHC(=O)NH—; —OC(=O)NH—; —NHC(=O)O—; —NHCH$_2$O—; —OCH$_2$NH—; —NHC(=S)O—; —OS(=O)NH—; —NHC(=O)C(=O)O—; —OC(=O)C(=O)NH—; —NHC(=O)C(=O)NH—; —OC(CH$_3$)$_2$O—; —NHC(CH$_3$)$_2$O—; —OC(CH$_3$)$_2$NH—$_{13}$ or any group that, when administered to a mammalian subject, cleaves to form a free dihydroxyl or diamino or hydroxyl and amino;

$R^{5a}$ is selected from hydrogen, halogen, $C_1$–$C_6$ alkyl, —N(R$^{20}$)$_2$, —SR$^{20}$, or —OR$^{20}$;

$R^{6a}$ is selected from: hydrogen, halogen, $C_1$–$C_6$ alkyl, —N(R$^{20}$)$_2$, —SR$^{20}$ or —OR$^{21}$;

$R^5$ and $R^{5a}$ can alternatively join to form =O, =S, or a ketal ring;

$R^6$ and $R^{6a}$ can alternatively join to form =O, =S, or a ketal ring;

$R^{20}$ and $R^{21}$ are independently selected from:
 hydrogen;
 $C_1$–$C_6$ alkyl substituted with 0–3 $R^{11}$;
 $C3$–$C_6$ alkoxyalkyl substituted with 0–3 $R^{11}$;
 $C_1$–$C_6$ alkylcarbonyl substituted with 0–3 $R^{11}$;
 $C_1$–$C_6$ alkoxycarbonyl substituted with 0–3 $R^{11}$;
 $C_1$–$C_6$ alkylaminocarbonyl substituted with 0–3 $R^{11}$;
 benzoyl substituted with 0–3 $R^{12}$;
 phenoxycarbonyl substituted with 0–3 $R^{12}$;
 phenylaminocarbonyl substituted with 0–3 $R^{12}$; or
 any group that, when administered to a mammalian subject, cleaves to form a free hydroxyl, amino or sulfhydryl;

$R^{11}$ is selected from one or more of the following:
 H, keto, halogen, cyano, —CH$_2$NR$^{13}$R$^{14}$, —NR$^{13}$R$^{14}$, —CO$_2$R$^{13}$, —OC(=O)R$^{13}$, —OR$^{13}$, $C_2$–$C_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{14}$SO$_2$NR$^{13}$R$^{14}$, —NR$_{14}$SO$_2$R$^{13}$, —SO$_2$NR$^{13}$R$^{14}$, —OP(O)(OR$^{13}$)$_2$, $C_1$-alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —NR$^{13}$R$^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, pyridylcarbonyloxy, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, azido, or —(R$^{14}$)=N(OR$^{14}$);
 1–3 amino acids linked together via amide bonds, said amino acid being linked via the amine or carboxylate terminus;
 $C_3$–$C_{10}$ cycloalkyl substituted with 0–2 $R^{12}$;
 $C_1$–$C_4$ alkyl substitued with 0–2 $R^{12}$
 aryl($C_1$–$C_3$ alkyl)substituted with 0–2 $R^{12}$;
 $C_2$–$C_6$ alkoxyalkyl, substituted with 0–2 $R^{12}$;
 $C_1$–$C_4$ alkylcarbonyloxy substituted with 0–2 $R^{12}$,
 $C_6$–$C_{10}$ arylcarbonyloxy substituted with 0–2 $R^{12}$,
 a $C_5$–$C_{14}$ carbocyclic residue substituted with 0–3 $R^{12}$; or
 a 5-to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:
 H, keto, halogen, cyano, —CH$_2$NH$_2$, —NH$_2$, —NHMe, —CO$_2$H, —OC(=O)($C_1$–$C_3$ alkyl), —OH, $C_2$–$C_6$ alkoxyalkyl, —C(=O)NH$_2$, —OC(=O)NH$_2$, —NHC(=O)NH$_2$, —SO$_2$NH$_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —NH$_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, azido, aryl($C_1$–$C_3$ alkyl), a $C_5$–$C_{14}$ carbocyclic residue; a 5-to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is selected from one or more of the following:
 phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —CO$_2$ H, hydroxamic acid, hydrazide, oronic acid, sulfonamide, formyl, $C_3$–$C_6$ cycloalkoxy, —OR$^{13}$, $C_1$–$C_4$ alkyl substituted with —NR$^{13}$R$^{14}$, —NR$^{13}$R$^{14}$, $C_2$–$C_6$ alkoxyalkyl optionally substituted with —Si(CH$_3$)$_3$,, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_3$ alkylcarbonyl, $C_1$–$C_4$ alkylcarbonylamino, —S(O)$_m$R$^{13}$, —SO$_2$NR$^{13}$R$^{14}$, —NHSO$_2$R$^{14}$, —OCH$_2$CO$_2$R$^{13}$, 2-(1-morpholino)ethoxy, or —C(R$^{14}$)=N(OR$^{14}$); or
 a 5-or 6-membered heterocyclic ring containing from 1 to 4 heteroatoms independently selected from oxygen, nitrogen or sulfur;

or $R^{12}$ may be a 3-or 4-carbon chain attached to adjacent carbons on the ring to form a fused 5-or 6-membered ring, said 5-or 6-membered ring being optionally substituted on the aliphatic carbons with halogen, $C_1$–$C_4$ alkyl, $C_1$–$C_4$ alkoxy, hydroxy, or —NR$^{13}$R$^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:
 phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$NR$^{13}$R$^{14}$, —NR$^{13}$R$^{14}$, $C_2$–$C_6$ alkoxyalkyl, $C_1$–$C_4$ haloalkyl, $C_1$–$C_4$ alkoxycarbonyl, —CO$_2$H, $C_1$–$C_4$ alkylcarbonyloxy, $C_1$–$C_4$ alkylcarbonyl, or —C(R$^{14}$)=N(OR$^{14}$);

$R^{12A}$, when a substituent on carbon, is selected from one or more of the following:
 phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —CO$_2$H, hydroxamic acid, hydrazide, boronic acid, sulfonamide, formyl, $C_3$–$C_6$ cycloalkoxy, —OR$^{13}$, $C_1$–$C_4$ alkyl substituted with —NH$_2$, —NH$_2$, —NHMe, $C_2$–$C_6$ alkoxyalkyl optionally substituted with —Si(CH$_3$)$_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m$Me, —SO$_2$NH$_2$, —NHSO$_2$Me, —OCH$_2$CO$_2$R$^{13b}$, 2-(1-morpholino)ethoxy, —C(=NOH)NH$_2$; or a 5-or 6-membered heterocyclic ring containing from 1 to 4 heteroatoms independently selected from oxygen, nitrogen or sulfur;

or R$^{12A}$ may be a 3-or 4-carbon chain attached to adjacent carbons on the ring to form a fused 5-or 6-membered ring, said 5-or 6-membered ring being optionally substituted on the aliphatic carbons with halogen, $C_1$–$C_4$ alkyl, $C_1$–$C_4$ alkoxy, hydroxy, or —NH$_2$; or, when R$^{12A}$ is attached to a saturated carbon atom or sulfur, it may be =O or =S;

R$^{12A}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$NH$_2$, —NH$_2$, $C_2$–$C_6$ alkoxyalkyl, $C_1$–$C_4$ haloalkyl, $C_1$–$C_4$ alkoxycarbonyl, —CO$_2$H, $C_1$–$C_4$ alkylcarbonyloxy, $C_1$–$C_4$ alkylcarbonyl, —C(=NOH)NH$_2$;

R$^{13}$ is selected from:
H;
phenyl substituted with 0–3 R$^{11A}$;
benzyl substituted with 0–3 R$^{11A}$;
$C_1$–$C_6$ alkyl substituted with 0–3 R$^{11A}$;
$C_2$–$C_4$ alkenyl substituted with 0–3 R$^{11A}$;
$C_1$–$C_6$ alkylcarbonyl substituted with 0–3 R$^{11A}$;
$C_1$–$C_6$ alkoxycarbonyl substituted with 0–3 R$^{11A}$;
$C_1$–$C_6$ alkylaminocarbonyl substituted with 0–3 R$^{11A}$;
$C_3$–$C_6$ alkoxyalkyl substituted with 0–3 R$^{11A}$;
an amine protecting group when R$^{13}$ is bonded to N; or
a hydroxy protecting group when R$^{13}$ is bonded to O;

R$^{14}$ is hydrogen, hydroxy, CF$_3$; $C_1$–$C_6$ alkyl substituted with 0–3 groups selected from OH, $C_1$–$C_4$ alkoxy, halogen, NH$_2$, $C_1$–$C_6$ alkoxy; NH$_2$; —NH($C_1$–$C_4$ alkyl), $C_2$–$C_6$ alkenyl; phenyl, benzyl, an amine protecting group when R$^{14}$ is bonded to N, or a hydroxy protecting group when R$^{14}$ is bonded to O;

R$^{13}$ can alternatively join to form —(CH$_2$)$_4$—, —(CH$_2$)$_5$—, —(CH$_2$)$_2$N, N(R$^{15}$)CH$_2$CH$_2$—, or —CH$_2$CH$_2$OCH$_2$CH$_2$—;

R$^{15}$ is H or CH$_3$;

m is 0, 1 or 2;

W is
—N(R$^{22}$)C(=Z)N(R$^{23}$)—;
wherein:

Z is O;

R$^{22}$ and R$^{23}$ are independently selected from the following:
hydrogen;
$C_1$–$C_8$ alkyl substituted with 0–3 R$^{31}$;
$C_2$–$C_8$ alkenyl substituted with 0–3 R$^{31}$;
$C_2$–$C_8$ alkynyl substituted with 0–3 R$^{31}$;
a $C_3$–$C_{14}$ carbocyclic ring system substituted with 0–5 R$^{31}$ or R$^{32}$;
a 5-to 10-membered heterocyclic ring system containing 1 to 4 to heteroatoms independently selected from oxygen, nitrogen or sulfur, said heterocyclic ring system being substituted with 0–5 R$^{32}$;
—OR$^{22a}$; or —N(R$^{22a}$)(R$^{22b}$);

R$^{22a}$ and R$^{22b}$ are independently selected from the following:
hydrogen;
$C_1$–$C_8$ alkyl substituted with 0–3 R$^{31}$;
$C_2$–$C_8$ alkenyl substituted with 0–3 R$^{31}$;
$C_2$–$C_8$ alkynyl substituted with 0–3 R$^{31}$;
a $C_3$–$C_{14}$ carbocyclic ring system substituted with 0–5 R$^{31}$ or R$^{32}$;
a 5-to 10-membered heterocyclic ring system containing 1 to 4 heteroatoms independently selected from oxygen, nitrogen or sulfur, said heterocyclic ring system being substituted with 0–5 R$^{32}$;

alternatively, R$^{22}$ can join with R$^4$ or R$^{4A}$ to form a 5-or 6-membered fused heterocyclic ring or carbocyclic ring substituted with 0–2 R$^{12}$, said heterocyclic ring containing 1–3 heteroatoms independently selected from N, S, or O; or alternatively, R$^{23}$ can join with R$^7$ or R$^{7A}$ to form a 5-or 6-membered fused heterocyclic ring or carbocyclic ring substituted with 0–2 R$^{12}$, said heterocyclic ring containing 1–3 heteroatoms independently selected from N, S, or O; or alternatively, R$^{22}$ or R$^{23}$ can join with R$^5$ or R$^6$ to form a 0- to 7-membered bridge to form a carbocyclic or heterocyclic ring, said bridge being substituted with 0–2 R$^{12}$ and said bridge containing 0–3 heteroatoms independently selected from N, S, or O (i.e., a 0-membered bridge is formed when R$^{22}$ or R$_{23}$ are taken together with R$^5$ or R$^6$ to form a direct bond); or alternatively R23 can join with R7A to form a direct bond; or alternatively R22 can join with R4A to form a direct bond;

R$^{31}$ is selected from one or more of the following:
keto, halogen, cyano, —CH$_2$NR$^{13}$R$^{14}$, —NR$^{13}$R$^{14}$, —CO$_2$R$^{13}$, —C(=O)R$^{11}$, —OC(=O)R$^{13}$, —OR$^{13}$, $C_2$–$C_6$ alkoxyalkyl, —S(O)m$^{R13}$, —NR$^{13}$C(=S)NR$^{13}$R$^{14}$, —NR$^{14}$SO$_2$NR$^{13}$R$^{14}$, —NR$^{13}$SO$_2$R$^{13}$, —NHC(=NH)NHR$^{13}$, —C(=NH)NHR$^{13}$, —C(=O)NR$^{13}$R$^{14}$, —NR$^{13}$C(=O)R$^{13}$, =NOR$^{13}$, —NR$^{14}$C(=O)OR$^{14}$, —OC(=O)NR$^{13}$R$^{14}$, —NR$^{13}$C(=O)NR$^{13}$R$^{14}$, —SO$_2$NR$^{13}$R$^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —NR$^{13}$R$^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$R$^{13}$, 2-(1-morpholino)ethoxy, azido, —C(R$^{14}$)=N(OR$^{14}$); or 1–3 amino acids, linked together via amide bonds, said amino acid being linked via the amine or carboxylate terminus;

a $C_5$–$C_{14}$ carbocyclic residue substituted with 0–5 R$^{32}$; or a 5-to 10-membered heterocyclic ring system containing 1 to 4 heteroatoms independently selected from oxygen, nitrogen or sulfur, said heterocyclic ring system being substituted with 0–2 R$^{32}$;

R$^{32}$, when a substituent on carbon, is selected from one or more of the following:
phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —NHSO$_2$R$^{14}$, benzyloxy, halogen, 2-(1-morpholino)ethoxy, —CO$_2$R$^{13}$, hydroxamic acid, —CONR$^{13}$NR$^{13}$R$^{14}$, cyano, boronic acid, sulfonamide, —CHO, C$_3$–C$_6$ cycloalkoxy, —NR$^{13}$R$^{14}$, —C(R$^{14}$)=N(OR$^{14}$)NO$_2$, OR$^{13}$,—NR$^{40}$R$^{41}$, —SO$_m$R$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —OCO$_2$R$^{13}$, phenyl, —C(=O)NR$^{13}$(C$_1$–C$_4$ alkyl)-NR$^{13}$R$^{14}$, —C(=O)NR$^{40}$R$^{41}$, C$_1$–C$_4$ haloalkyl, C$_2$–C$_4$ haloalkenyl, C$_1$–C$_4$ haloalkynyl, C$_1$–C$_4$ haloalkenyl, or —C(=O)NR$^{13}$C(R$^{11}$)$_2$NR$^{13}$R$^{14}$; —
—C(=O)NR$^{13}$C(R$^{11}$)$_2$NR$^{13}$NR$^{14}$;
—C(=O)NR$^{13}$C(R$^{11}$)$_2$NR$^{13}$CO$_2$R$^{13}$;
—C(=O)NR$^{13}$-(C$_1$–C$_4$ alkyl)—NR$^{13}$CO$_2$R$^{13}$;
—C(=O)N(R$^{13}$)-(C$_1$–C$_4$ alkyl)-R$^{11}$; or
—C(=O)C(R$^{11}$)$_2$NR$^{13}$R$^{14}$;
—C(=O)C(R$^{11}$)$_2$NR$^{13}$NR$^{14}$;
—C(=O)C(R$^{11}$)$_2$NR$^{13}$CO$_2$R$^{13}$; —C(=O)-(C$_1$–C$_4$ alkyl)—NR$^{13}$R$^{14}$;
—C(=O)-(C$_1$–C$_4$ alkyl)—NR$^{13}$CO$_2$R$^{13}$; or
C$_1$–C$_4$ alkoxy substituted with 0–4 groups selected from: R$^{11}$, C$_{3-C_6}$ cycloalkyl, —CO$_2$R$^{13}$, —C(=O)NR$^{13}$R$^{14}$, —NR$^{13}$R$^{14}$ or OH;

C$_1$–C$_4$ alkyl substituted with 0–4 groups selected from: R$^{11}$ =NR$^{14}$, =NNR$^{13}$C(=O)NR$^{13}$R$^{14}$ or —NR$^{13}$R$^{14}$, =NNR$^{13}$C(=O)OR$^{13}$,;

C$_2$–C$_4$ alkenyl substituted with 0–4 R$^{11}$;
C$_2$–C$_4$ alkynyl substituted with 0–4 R$^{11}$;
a 5-or 6-membered heterocyclic ring containing from 1 to 4 heteroatoms independently selected from oxygen, nitrogen or sulfur, substituted with 0–2 R$^{12}$;

or R$^{32}$ may be a 3-or 4-carbon chain attached to adjacent carbons on the ring to form a fused 5-or 6-membered ring, said 5-or 6-membered ring being optionally substituted on the aliphatic carbons with halogen, C$_1$–C$_4$ alkyl, C$_1$–C$_4$ alkoxy, hydroxy, or —NR$^{13}$R$^{14}$; or, when R$^{32}$ is attached to a saturated carbon atom, it may be =O or =S, =NOH; or when R$^{32}$ is attached to sulfur it may be =O;

R$^{32}$, when a substituent on nitrogen, is selected from one or more of the following:
phenyl, benzyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$NR$^{13}$R$^{14}$, —NR$^{13}$R$^{14}$, C$_2$–C$_6$ alkoxyalkyl, C$_1$–C$_4$ haloalkyl, C$_1$–C$_4$ alkoxycarbonyl, —CO$_2$H, C$_1$–C$_4$ alkylcarbonyloxy, C$_1$–C$_4$ alkylcarbonyl, or —C(R$^{14}$)=N (OR$^{14}$);

R$^{40}$ is selected from: H or C$_1$–C$_3$ alkyl;
R$^{41}$ is selected from:
—C(=O)NR$^{13}$R$^{14}$;
—C(=O)NR$^{13}$NR$^{13}$R$^{14}$;
—C(=O)C(R$^{11}$)$_2$NR$^{13}$R$^{14}$;
—C(=O)C(R$^{11}$)$_2$NR$^{13}$NR$^{13}$R$^{14}$;
—C(=O)C(R$^{11}$)$_2$NR$^{13}$CO$_2$R$^{13}$;
—C(=O)H;
—C(=O)R$^{11}$;
—C(=O)-(C$_1$–C$_4$ alkyl)—NR$^{13}$R$^{14}$;
—C(=O)-(C$_1$–C$_4$ alkyl)—NR$^{13}$CO$_2$R$^{13}$;
1–3 amino acids linked together via amide bonds, and linked to the N atom via the carboxylate terminus;
provided that:
R$^4$, R$^{4A}$, R$^7$ and R$^{7A}$ are not all hydrogen;
when R$^4$, R$^{4A}$ are hydrogen, R$^{22}$ and (b) a vehicle comprising a fatty acid ester of glycerol, a fatty acid ester of polyethylene glycol, or mixture thereof, wherein said vehicle has a hydrophil-lipophil balance of at least about 10.

39. A pharmaceutical kit of claim 38 further comprising conventional kit components.

40. A pharmaceutical dosage form for oral administration comprising a gelatin capsule containing in the hollow interior thereof, a pharmaceutical composition comprising:

(a) a therapeutically effective amount of compound of the Formula (I):

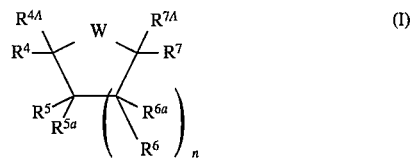

or a pharmaceutically acceptable salt or prodrug form thereof,
wherein:
R$^4$ and R$^7$ are independently selected from the following groups:
hydrogen;
C$_1$–C$_8$ alkyl substituted with 0–3 R$^{11}$;
C$_2$–C$_8$ alkenyl substituted with 0–3 R$^{11}$;
C$_2$–C$_8$ alkynyl substituted with 0–3 R$^{11}$;
a C$_3$–C$^{14}$ carbocyclic ring system substituted with 0–3 R$^{11}$ or 0–3 R$^{12}$;
a 5-to 10-membered heterocyclic ring system containing 1 to 4 heteroatoms independently selected from oxygen, nitrogen or sulfur, said heterocyclic ring system being substituted with 0–2 R$^{12}$; or
—OR$^{13}$; —SR$^{13}$; CO$_2$R$^{13}$;

R$^{4A}$ and R$^{7A}$ are independently selected from the following groups:
hydrogen;
C$_1$–C$_4$ alkyl substituted with 0–6 halogen or 0–3 C$_1$–C$_2$ alkoxy;
benzyl substituted with 0–6 halogen or 0–3 C$_1$–C$_2$ alkoxy; or —OR$^{13}$; —SR$^{13}$; CO$_2$R$^{13}$;

R$^4$ and R$^{4A}$ can alternatively join to form a 5–7 membered carbocyclic ring substituted with 0–2 R$^{12}$;

R$^7$ and R$^{7A}$ can alternatively join to form a 5–membered carbocyclic ring substituted with 0–2 R$^{12}$;

n is 0;

R$^5$ is selected from H; halogen; C$_1$–C$_6$ alkyl substituted with 0–3 R$^{11}$; —N(R$^{20}$)$_2$; —SR$^{20}$; or —OR$^{20}$, —N$_3$;

R$^6$ is independently selected from: hydrogen, halogen, C$_1$–C$_6$ alkyl substituted with 0–3 R$^{11}$, —N(R$^{20}$)$_2$, —SR$^{20}$, or —OR$^{21}$, —N$_3$;

R$^5$ and R$^6$ can alternatively join to form an epoxide or aziridine ring; —OCH$_2$SCH$_2$O—; —OS(=O)O—; —OC(=O)O—; —OCH$_2$O—; —OC(=S)O—; —OC(=O)C(=O)O—; —OC(CH$_3$)$_2$O—; —OC((CH$_2$)$_3$NH$_2$)(CH$_3$)O—; —OC(OCH$_3$)(CH$_2$CH$_2$CH$_3$)O—; —OS(=O)O—; —NHC(=O)NH—; —OC(=O)NH—; —NHC(=O)O—; —NHCH$_2$O—; —OCH$_2$NH—; —NHC(=SO—; —OS(=O)NH—; —NHC(=O)C(=O)O—; —OC(=O)C(=O)NH—; —NHC(=O)C(=O)NH—; —OC(CH$_3$)$_2$O—; —NHC(CH$_3$)$_2$O—; —OC(CH$_3$)$_2$NH— or any group that, when administered to a mammalian subject, cleaves to form a free dihydroxyl or diamino or hydroxyl and amino;

R$^{5a}$ is selected from hydrogen, halogen, C$_1$–C$_6$ alkyl, —N(R$_{20}$)$_2$, —SR$^{20}$, or —OR$^{20}$;

$R^{6a}$ is selected from: hydrogen, halogen, $C_1$–$C_6$ alkyl, —N($R^{20}$)$_2$, —S$R^{20}$ or —O$R^{21}$;

$R^5$ and $R^{5a}$ can alternatively join to form =O, =S, or a ketal ring;

$R^6$ and $R^{6a}$ can alternatively join to form =O, =S, or a ketal ring;

$R^{20}$ and $R^{21}$ are independently selected from:
  hydrogen;
  $C_1$–$C_6$ alkyl substituted with 0–3 $R^{11}$;
  $C_3$–$C_6$ alkoxyalkyl substituted with 0–3 $R^{11}$;
  $C_1$–$C_6$ alkylcarbonyl substituted with 0–3 $R^{11}$;
  $C_1$–$C_6$ alkoxycarbonyl substituted with 0–3 $R^{11}$;
  $C_1$–$C_6$ alkylaminocarbonyl substituted with 0–3 $R^{11}$;
  benzoyl substituted with 0–3 $R^{12}$;
  phenoxycarbonyl substituted with 0–3 $R^{12}$;
  phenylaminocarbonyl substituted with 0–3 $R^{12}$; or
  any group that, when administered to a mammalian subject, cleaves to form a free hydroxyl, amino or sulfhydryl;

$R^{11}$ is selected from one or more of the following:
  H, keto, halogen, cyano, —CH$_2$N$R^{13}R^1$, —N$R^{13}R^{14}$, —CO$_2R^{13}$, —OC(=O)$R^{13}$, —O$R^{13}$, $C_2$–$C_6$ alkoxyalkyl, —S(O)$_m R^{13}$, —NHC(=NH)NH$R^{13}$, —C(=NH)NH$R^{13}$, —C(=O)N$R^{13}R^{14}$, —N$R^{14}$C(=O)$R^{13}$, =NO$R^{14}$, —N$R^{14}$C(=O)O$R^{14}$, —OC(=O)N$R^{13}R^{14}$, —N$R^{13}$C(=O)N$R^{13}R^{14}$, —N$R^{14}$SO$_2$N$R^{13}R^{14}$, —N$R^{14}$SO$_2R^{13}$, —SO$_2$N$R^{13}R^{14}$, —OP(O)(O$R^{13}$)$_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —N$R^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, pyridylcarbonyloxy, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, azido, or —($R^{14}$)=N(O$R^{14}$);

1—3 amino acids linked together via amide bonds, said amino acid being linked via the amine or carboxylate terminus;
  $C_3$–$C_{10}$ cycloalkyl substituted with 0–2 $R^{12}$;
  $C_1$–$C_4$ alkyl substitued with 0–2 $R^{12}$
  aryl($C_1$–$C_3$ alkyl) substituted with 0–2 $R^{12}$;
  $C_2$–$C_6$ alkoxyalkyl, substituted with 0–2 $R^{12}$;
  $C_1$–$C_4$ alkylcarbonyloxy substituted with 0–2 $R^{12}$,
  $C_6$–$C_{10}$ arylcarbonyloxy substituted with 0–2 $R^{12}$,
  a $C_5$–$C_{14}$ carbocyclic residue substituted with 0–3 $R^{12}$; or
  a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:
  H, keto, halogen, cyano, —CH$_2$NH$_2$, —NH$_2$, —NHMe, —CO$_2$H, —OC(=O)($C_1$–$C_3$ alkyl), —OH, $C_2$–$C_6$ alkoxyalkyl, —C(=O)NH$_2$, —OC(=O)NH$_2$, —NHC(=O)NH$_2$, —SO$_2$NH$_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —NH$_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, azido, aryl($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is selected from one or more of the following:
  phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —CO$_2$H, hydroxamic acid, hydrazide, oronic acid, sulfonamide, formyl, $C_3$–$C_6$ cycloalkoxy, —O$R^{13}$, $C_1$–$C_4$ alkyl substituted with —N$R^{13}R^{14}$, —N$R^{13}R^{14}$, $C_2$–$C_6$ alkoxyalkyl optionally substituted with —Si(CH$_3$)$_3$,, Cl—$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m R^{13}$, —SO$_2$N$R^{13}R^{14}$, —NHSO$_2R^{14}$, —OCH$_2$CO$_2R^{13}$, 2-(1-morpholino)ethoxy, or —C($R^{14}$)=N(O$R^{14}$); or
  a 5- or 6-membered heterocyclic ring containing from 1 to 4 heteroatoms independently selected from oxygen, nitrogen or sulfur;
  or $R^{12}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —N$R^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$N$R^{13}R^{14}$, —N$R^{13}R^{14}$, $C_2$–$C_6$ alkoxyalkyl, $C_1$–$C_4$ haloalkyl, $C_1$–$C_4$ alkoxycarbonyl, —CO$_2$H, $C_1$–$C_4$ alkylcarbonyloxy, $C_1$–$C_4$ alkylcarbonyl, or —C($R^{14}$)=N(O$R^{14}$);

$R^{12A}$, when a substituent on carbon, is selected from one or more of the following:
  phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —CO$_2$H, hydroxamic acid, hydrazide, boronic acid, sulfonamide, formyl, $C_3$–$C_6$ cycloalkoxy, —O$R^{13}$, $C_1$–$C_4$ alkyl substituted with —NH$_2$, —NH$_2$, —NHMe, $C_2$–$C_6$ alkoxyalkyl optionally substituted with —Si(CH$_3$)$_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m$Me, —SO$_2$NH$_2$, —NHSO$_2$Me, —OCH$_2$CO$_2R^{13}$, 2-(1-morpholino)ethoxy, —C(=NOH)NH$_2$; or
  a 5- or 6-membered heterocyclic ring containing from 1 to 4 heteroatoms independently selected from oxygen, nitrogen or sulfur;
  or $R^{12A}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NH_2$; or, when $R^{12A}$ is attached to a saturated carbon atom or sulfur, it may be =O or =S;

$R^{12A}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NH_2$, —$NH_2$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(=NOH)NH_2$;

$R^{13}$ is selected from:
H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_1$–$C_6$ alkylcarbonyl substituted with 0–3 $R^{11A}$;
$C_1$–$C_6$ alkoxycarbonyl substituted with 0–3 $R^{11A}$;
$C_1$–$C_6$ alkylaminocarbonyl substituted with 0–3 $R^{11A}$;
$C_3$–$C_6$ alkoxyalkyl substituted with 0–3 $R^{11A}$;
an amine protecting group when $R^{13}$ is bonded to N; or
a hydroxy protecting group when $R^{13}$ is bonded to O;

$R^{14}$ is hydrogen, hydroxy, $CF_3$; $C_1$–$C_6$ alkyl substituted with 0–3 groups selected from OH, $C_1$–$C_4$ alkoxy, halogen, $NH_2$, $C_1$–$C_6$ alkoxy; $NH_2$; —$NH(C_1$–$C_4$ alkyl), $C_2$–$C_6$ alkenyl; phenyl, benzyl, an amine protecting group when $R^{14}$ is bonded to N, or a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

W is
—$N(R^{22})C(=Z)N(R^{23})$—;
wherein:
Z is O;
$R^{22}$ and $R^{23}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system containing 1 to 4 heteroatoms independently selected from oxygen, nitrogen or sulfur, said heterocyclic ring system being substituted with 0–5 $R^{32}$;
—$OR^{22a}$; or —$N(R^{22a})(R^{22b})$;

$R^{22a}$ and $R^{22b}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C^{14}$ carbocyclic ring system substituted with 0–5 $R^{31}$ or $R^{32}$;
a 5- to 10-membered heterocyclic ring system containing 1 to 4 heteroatoms independently selected from oxygen, nitrogen or sulfur, said heterocyclic ring system being substituted with 0–5 $R^{32}$;

alternatively, $R^{22}$ can join with $R^4$ or $R^{44}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$ can join with $R^7$ or $R^{7A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$ or $R^{23}$ can join with $R^5$ or $R^6$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$ or $R^{23}$ are taken together with $R^5$ or $R^6$ to form a direct bond); or alternatively R23 can join with R7A to form a direct bond; or alternatively R22 can join with R4A to form a direct bond;

$R^{31}$ is selected from one or more of the following:
keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$—$NR^{13}C(=S)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})=N(OR^{14})$; or
1–3 amino acids, linked together via amide bonds, said amino acid being linked via the amine or carboxylate terminus;
a $C_5$–$C_{14}$ carbocyclic residue substituted with 0–5 $R^{32}$; or
a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})=N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—$(C_1$–$C_4$ alkyl)-$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or
—$C(=O)NR^{13}C(R^{11})_2NR^{13}R^{14}$;
—$C(=O)NR^{13}C(R^{11})_2NR^{13}NR^{11}$;

—C(=O)NR$^{13}$C(R$^{11}$)$_2$NR$^{13}$CO$_2$R$^{13}$;
—C(=O)NR$^{13}$-(C$_1$-C$_4$ alkyl)—NR$^{13}$CO$_2$R$^{13}$;
—C(=O)N(R$^{13}$)-(C$_1$-C$_4$ alkyl)-R$^{11}$; or
—C(=O)C(R$^{11}$)$_2$NR$^{13}$R$^{11}$;
 —C(=O)C(R$^{11}$)$_2$NR$^{13}$NR$^{11}$;
—C(=O)C(R$^{11}$)$_2$NR$^{13}$CO$_2$R$^{13}$;  —C(=O)(C$_1$-C$_4$ alkyl)—NR$^{13}$R$^{14}$;  —C(=O)-(C$_1$-C$_4$ alkyl)—NR$^{13}$CO$_2$R$^{13}$; or C$_1$-C$_4$ alkoxy substituted with 0–4 groups selected from: R$^{11}$, C$_3$-C$_6$ cycloalkyl, —CO$_2$R$^{13}$, —C(=O)NR$^{13}$R$^{14}$, —NR$^{13}$R$^{14}$ or OH;

C$_1$-C$_4$ alkyl substituted with 0–4 groups selected from: R$^{11}$, =NR$^{14}$, =NNR$^{13}$C(=O)NR$^{13}$R$^{14}$ or —N$^{13}$R$^{14}$, =NNR$^{13}$C(=O)OR$^{13}$;

C$_2$-C$_4$ alkenyl substituted with 0–4 R$^{11}$;
C$_2$-C$_4$ alkynyl substituted with 0–4 R$^{11}$;
a 5- or 6-membered heterocyclic ring containing from 1 to 4 heteroatoms independently selected from oxygen, nitrogen or sulfur, substituted with 0–2 R$^{12}$;

or R$^{32}$ may be a 3- or 4-carbon chain attached to adjacent carbons on the ring to form a fused 5-or 6-membered ring, said 5- or 6-membered ring being optionally substituted on the aliphatic carbons with halogen, C$_1$-C$_4$ alkyl, C$_1$-C$_4$ alkoxy, hydroxy, or —NR$^{13}$R$^{14}$;

or, when R$^{32}$ is attached to a saturated carbon atom, it may be =O or =S, =NOH; or when R$^{32}$ is attached to sulfur it may be =O.

R$^{32}$, when a substituent on nitrogen, is selected from one or more of the following:

phenyl, benzyl, phenethyl, hydroxy, C$_1$-C$_4$ hydroxyalkyl, C$_1$-C$_4$ alkoxy, C$_1$-C$_4$ alkyl, C$_3$-C$_6$ cycloalkyl, C$_3$-C$_6$ cycloalkylmethyl, —CH$_2$NR$^{13}$R$^{14}$, —NR$^{13}$R$^{14}$, C$_2$-C$_6$ alkoxyalkyl, C$_1$-C$_4$ haloalkyl, C$_1$-C$_4$ alkoxycarbonyl, —CO$_2$H, C$_1$-C$_4$ alkylcarbonyloxy, C$_1$-C$_4$ alkylcarbonyl, or —C(R$^{14}$)=N(OR$^{14}$);

C$_1$-C$_6$ alkyl substituted with 0–3 R$^{11}$; hydroxyl;
C$_1$-C$_6$ alkoxy substituted with 0–3 R$^{11}$ or
—NR$^{38}$R$^{39}$;

R$^{38}$ and R$^{39}$ are independently selected from:
hydrogen;
C$_1$-C$_6$ alkyl substituted with 0–3 R$^{11}$ or
an amine protecting groug;]

R$^{40}$ is selected from: H or C$_1$-C$_3$ alkyl;
R$^{41}$ is selected from:
—C(=O)NR$^{13}$R$^{14}$;
—C(=O)NR$^{13}$NR$^{13}$R$^{14}$;
—C(=O)C(R$^{11}$)$_2$NR$^{13}$R$^{14}$;
—C(=O)C(R$^{11}$)$_2$NR$^{13}$NR$^{13}$R$^{14}$;
—C(=O)C(R$^{11}$)$_2$NR$^{13}$CO$_2$R$^{13}$;
—C(=O)H;
—C(=O)R$^{11}$;
—C(=O)-(C$_1$-C$_4$ alkyl)—NR$^{13}$R$^{14}$;
—C(=O)-(C$_1$-C$_4$ alkyl)—NR$^{13}$CO$_2$R$^{13}$;
1–3 amino acids linked together via amide bonds, and linked to the N atom via the carboxylate terminus;

provided that:
R$^4$, R$^{4A}$, R$^7$ and R$^{7A}$ are not all hydrogen;
when R$^4$, R$^{4A}$ are hydrogen, R$^{22}$ is not hydrogen; and
(b) a vehicle comprising a fatty acid ester of glycerol, a fatty acid ester of polyethylene glycol, or mixture thereof, wherein said vehicle has a hydrophil-lipophil balance of at least about 10.

41. A pharmaceutical dosage form of claim 40 wherein said compound of Formula (I)is present in an amount of about 50–250 mg/capsule.

* * * * *